US010364418B2

(12) United States Patent
Marliére et al.

(10) Patent No.: US 10,364,418 B2
(45) Date of Patent: Jul. 30, 2019

(54) 3-HYDROXYISOVALERATE (HIV) SYNTHASE VARIANTS

(71) Applicants: Global Bioenergies, Evry (FR); Scientist of Fortune, S.A., Luxembourg (LU)

(72) Inventors: Philippe Marliére, Luxembourg (LU); Marc Delcourt, Paris (FR); Sabine Mazaleyrat, Le Russey (FR); Jean-Baptiste Barbaroux, Marseilles (FR)

(73) Assignees: Global Bioenergies, Evry (FR); Scientist of Fortune, S.A., Luxembourg (LU)

(*) Notice: Subject to any disclaimer, the term of this patent is extended or adjusted under 35 U.S.C. 154(b) by 95 days.

(21) Appl. No.: 15/108,917

(22) PCT Filed: Dec. 17, 2014

(86) PCT No.: PCT/EP2014/078120
§ 371 (c)(1),
(2) Date: Jun. 29, 2016

(87) PCT Pub. No.: WO2015/101493
PCT Pub. Date: Jul. 9, 2015

(65) Prior Publication Data
US 2016/0326500 A1    Nov. 10, 2016

(30) Foreign Application Priority Data
Dec. 31, 2013   (EP) .................................. 13199884

(51) Int. Cl.
*C12P 7/52* (2006.01)
*C12N 9/88* (2006.01)
*C12N 9/10* (2006.01)
*C12P 7/42* (2006.01)
*C12P 5/02* (2006.01)

(52) U.S. Cl.
CPC ............ *C12N 9/1025* (2013.01); *C12N 9/88* (2013.01); *C12P 5/026* (2013.01); *C12P 7/42* (2013.01); *C12Y 203/0301* (2013.01); *C12Y 401/03004* (2013.01); *Y02E 50/343* (2013.01)

(58) Field of Classification Search
CPC ..................................... C12P 7/52; C12N 9/88
See application file for complete search history.

(56) References Cited

U.S. PATENT DOCUMENTS

| 6,436,692 B1* | 8/2002 | Gong ....................... C12N 9/88 435/232 |
| 7,745,391 B2* | 6/2010 | Mintz ...................... G06F 19/24 514/19.3 |
| 9,017,977 B2* | 4/2015 | Marliere .............. C12N 9/1025 435/146 |
| 9,556,460 B2* | 1/2017 | Marliere .............. C12N 9/1025 |
| 2009/0100536 A1 | 4/2009 | Adams et al. |

FOREIGN PATENT DOCUMENTS

| EP | 1284298 A2 | 2/2003 |
| WO | 2011032934 A1 | 3/2011 |

OTHER PUBLICATIONS

Kattar-Cooley et al. 1990; Avian liver 2-hydroxy-3-methyglutaryl-CoA synthase: Distinct genes encode the cholesterorgenic and ketogenic isozymes. Archives of Biochemistry and Biophysics. 283(2): 523-529, with attached sequence alignment.*
Rokosz et al. 1994; Human cytoplasmic 3-hydroxy-3-nnethyglutaryl-CoA synthase: Expression, purification, and characterization of recombinant wild-type and Cys 129 mutant enzymes. Archives of Biochemistry and Biophysics. 312(1): 1-13), with attached sequence alignment.*
International Search Report from corresponding PCT/EP2014/078120, dated Mar. 27, 2015.
Extended European Search Report from corresponding EP 13199884. 1, dated Apr. 8, 2014.
Crouch et al., "A Mechanistic Rationalisation for the Substrate Specificity of Recombinant Mammalian 4-Hydroxyphenylpyruvate Dioxygenase (4-HPPD)", Tetrahedron, 1997, Elsevier Science Publishers, Amsterdam, NL, vol. 53, No. 20, May 19, 1997, pp. 6993-7010, XP004105682.
Written Opinion of the International Searching Authority from corresponding PCT/EP2014/078120, dated Mar. 27, 2015.
Anonymous: "Hmgcs1—3-hydroxy-3-methylglutaryl coenzyme A synthase—Mus musculus (Mouse) Hmgcsl gene & protein", Oct. 11, 2005 (Oct. 11, 2005), XP055442643, Retrieved from the Internet: URL:http://www.uniprot.org/uniprot/Q3UWQ9 [retrieved Jan. 19, 2018].
EPO Office Action dated Jan. 29, 2018 received in corresponding EP Application 14 828 020.9.

* cited by examiner

*Primary Examiner* — Karen Cochrane Carlson
(74) *Attorney, Agent, or Firm* — Michele M. Wales; Inhouse Patent Counsel, LLC

(57) ABSTRACT

Described are 3-hydroxyisovalerate (HIV) synthase variants having improved activity in converting acetone and a compound which provides an activated acetyl group into 3-hydroxyisovalerate (HIV). Moreover, described are in particular methods for the production of 3-hydroxyisovalerate and methods for the production of isobutene from acetone utilizing the HIV synthase variants of the present invention.

22 Claims, 11 Drawing Sheets

Figure 1:
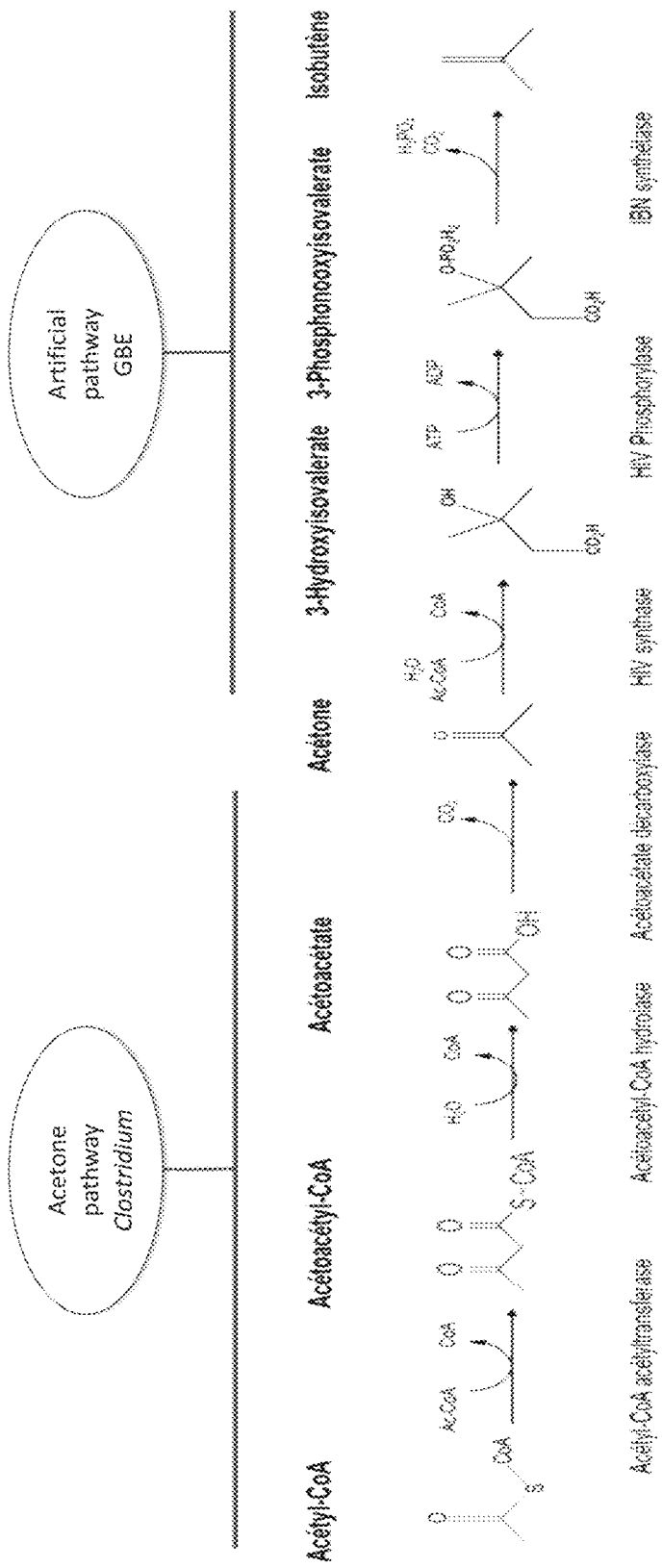

Specification includes a Sequence Listing.

SEQUENCE LISTING

<160> NUMBER OF SEQ ID NOS: 3

<210> SEQ ID NO 1
<211> LENGTH: 520
<212> TYPE: PRT
<213> ORGANISM: Mus musculus

<400> SEQUENCE: 1

Met Pro Gly Ser Leu Pro Leu Asn Ala Glu Ala Cys Trp Pro Lys Asp
1 5 10 15

Val Gly Ile Val Ala Leu Glu Ile Tyr Phe Pro Ser Gln Tyr Val Asp
20 25 30

Gln Ala Glu Leu Glu Lys Tyr Asp Gly Val Asp Ala Gly Lys Tyr Thr
35 40 45

Ile Gly Leu Gly Gln Ala Arg Met Gly Phe Cys Thr Asp Arg Glu Asp
50 55 60

```
Ile Asn Ser Leu Cys Leu Thr Val Val Gln Lys Leu Met Glu Arg His
 65                  70                  75                  80

Ser Leu Ser Tyr Asp Cys Ile Gly Arg Leu Glu Val Gly Thr Glu Thr
                 85                  90                  95

Ile Ile Asp Lys Ser Lys Ser Val Lys Ser Lys Leu Met Gln Leu Phe
            100                 105                 110

Glu Glu Ser Gly Asn Thr Asp Ile Glu Gly Ile Asp Thr Thr Asn Ala
            115                 120                 125

Cys Tyr Gly Gly Thr Ala Ala Val Phe Asn Ala Val Asn Trp Val Glu
            130                 135                 140

Ser Ser Ser Trp Asp Gly Arg Tyr Ala Leu Val Val Ala Gly Asp Ile
145                 150                 155                 160

Ala Ile Tyr Ala Thr Gly Asn Ala Arg Pro Thr Gly Gly Val Gly Ala
                165                 170                 175

Val Ala Leu Leu Ile Gly Pro Asn Ala Pro Leu Ile Phe Asp Arg Gly
            180                 185                 190

Leu Arg Gly Thr His Met Gln His Ala Tyr Asp Phe Tyr Lys Pro Asp
            195                 200                 205

Met Leu Ser Glu Tyr Pro Val Val Asp Gly Lys Leu Ser Ile Gln Cys
210                 215                 220

Tyr Leu Ser Ala Leu Asp Arg Cys Tyr Ser Val Tyr Arg Lys Lys Ile
225                 230                 235                 240

Arg Ala Gln Trp Gln Lys Glu Gly Lys Asp Lys Asp Phe Thr Leu Asn
                245                 250                 255

Asp Phe Gly Phe Met Ile Phe His Ser Pro Tyr Cys Lys Leu Val Gln
            260                 265                 270

Lys Ser Leu Ala Arg Met Phe Leu Asn Asp Phe Leu Asn Asp Gln Asn
            275                 280                 285

Arg Asp Lys Asn Ser Ile Tyr Ser Gly Leu Glu Ala Phe Gly Asp Val
            290                 295                 300

Lys Leu Glu Asp Thr Tyr Phe Asp Arg Asp Val Glu Lys Ala Phe Met
305                 310                 315                 320

Lys Ala Ser Ser Glu Leu Phe Asn Gln Lys Thr Lys Ala Ser Leu Leu
                325                 330                 335

Val Ser Asn Gln Asn Gly Asn Met Tyr Thr Ser Ser Val Tyr Gly Ser
            340                 345                 350

Leu Ala Ser Val Leu Ala Gln Tyr Ser Pro Gln Gln Leu Ala Gly Lys
            355                 360                 365

Arg Val Gly Val Phe Ser Tyr Gly Ser Gly Leu Ala Ala Thr Leu Tyr
            370                 375                 380

Ser Leu Lys Val Thr Gln Asp Ala Thr Pro Gly Ser Ala Leu Asp Lys
385                 390                 395                 400

Ile Thr Ala Ser Leu Cys Asp Leu Lys Ser Arg Leu Asp Ser Arg Thr
                405                 410                 415

Cys Val Ala Pro Asp Val Phe Ala Glu Asn Met Lys Leu Arg Glu Asp
            420                 425                 430

Thr His His Leu Ala Asn Tyr Ile Pro Gln Cys Ser Ile Asp Ser Leu
            435                 440                 445

Phe Glu Gly Thr Trp Tyr Leu Val Arg Val Asp Glu Lys His Arg Arg
            450                 455                 460

Thr Tyr Ala Arg Arg Pro Phe Thr Asn Asp His Ser Leu Asp Glu Gly
465                 470                 475                 480
```

```
Met Gly Leu Val His Ser Asn Thr Ala Thr Glu His Ile Pro Ser Pro
            485                 490                 495

Ala Lys Lys Val Pro Arg Leu Pro Ala Thr Ser Ala Glu Ser Glu Ser
            500                 505                 510

Ala Val Ile Ser Asn Gly Glu His
            515                 520

<210> SEQ ID NO 2
<211> LENGTH: 324
<212> TYPE: PRT
<213> ORGANISM: Artificial Sequence
<220> FEATURE:
<223> OTHER INFORMATION: HIV phosphorylase variant L200E

<400> SEQUENCE: 2

Met His His His His His Thr Tyr Arg Ser Ile Gly Ser Thr Ala
1               5                   10                  15

Tyr Pro Thr Ile Gly Val Val Leu Leu Gly Gly Ile Ala Asn Pro Val
            20                  25                  30

Thr Arg Thr Pro Leu His Thr Ser Ala Gly Ile Ala Tyr Ser Asp Ser
            35                  40                  45

Cys Gly Ser Ile Arg Ser Glu Thr Arg Ile Tyr Ala Asp Glu Ala Thr
    50                  55                  60

His Ile Tyr Phe Asn Gly Thr Glu Ser Thr Asp Asp Asn Arg Ser Val
65                  70                  75                  80

Arg Arg Val Leu Asp Arg Tyr Ser Ser Val Phe Glu Glu Ala Phe Gly
                85                  90                  95

Thr Lys Thr Val Ser Tyr Ser Ser Gln Asn Phe Gly Ile Leu Ser Gly
            100                 105                 110

Ser Ser Asp Ala Gly Ala Ala Ser Ile Gly Ala Ala Ile Leu Gly Leu
            115                 120                 125

Lys Pro Asp Leu Asp Pro His Asp Val Glu Asn Asp Leu Arg Ala Val
            130                 135                 140

Ser Glu Ser Ala Gly Arg Ser Leu Phe Gly Gly Leu Thr Ile Thr Trp
145                 150                 155                 160

Ser Asp Gly Phe His Ala Tyr Thr Glu Lys Ile Leu Asp Pro Glu Ala
                165                 170                 175

Phe Ser Gly Tyr Ser Ile Val Ala Phe Ala Phe Asp Tyr Gln Arg Asn
            180                 185                 190

Pro Ser Asp Val Ile His Gln Asn Ile Val Arg Ser Asp Glu Tyr Pro
            195                 200                 205

Ala Arg Lys Lys His Ala Asp Glu His Ala His Met Ile Lys Glu Tyr
            210                 215                 220

Ala Lys Thr Asn Asp Ile Lys Gly Ile Phe Asp Leu Ala Gln Glu Asp
225                 230                 235                 240

Thr Glu Glu Tyr His Ser Ile Leu Arg Gly Val Gly Val Asn Val Ile
                245                 250                 255

Arg Glu Asn Met Gln Lys Leu Ile Ser Tyr Leu Lys Leu Ile Arg Lys
            260                 265                 270

Asp Tyr Trp Asn Ala Tyr Ile Val Thr Gly Gly Ser Asn Val Tyr Val
            275                 280                 285

Ala Val Glu Ser Glu Asn Ala Asp Arg Leu Phe Ser Ile Glu Asn Thr
            290                 295                 300

Phe Gly Ser Lys Lys Met Leu Arg Ile Val Gly Gly Ala Trp His
305                 310                 315                 320
```

Arg Arg Pro Glu

<210> SEQ ID NO 3
<211> LENGTH: 324
<212> TYPE: PRT
<213> ORGANISM: Artificial Sequence
<220> FEATURE:
<223> OTHER INFORMATION: PIV decarboxylase variant K24R, C118L, Y121R, E159L, M173C, E177C, K282C, E291D, F297L

<400> SEQUENCE: 3

```
Met His His His His His Met Asp Arg Glu Pro Val Thr Val Arg
1               5                   10                  15

Ser Tyr Ala Asn Ile Ala Ile Ile Lys Tyr Trp Gly Lys Lys Arg Glu
            20                  25                  30

Lys Glu Met Val Pro Ala Thr Ser Ser Ile Ser Leu Thr Leu Glu Asn
            35                  40                  45

Met Tyr Thr Glu Thr Thr Leu Ser Ser Leu Pro Thr Asp Ala Thr Ala
    50                  55                  60

Asp Ala Phe Tyr Ile Asn Gly Gln Leu Gln Asn Glu Ala Glu His Val
65                  70                  75                  80

Lys Met Ser Lys Ile Ile Asp Arg Tyr Arg Pro Asp Gly Asp Gly Phe
                85                  90                  95

Val Arg Ile Asp Thr Gln Asn Ser Met Pro Thr Ala Ala Gly Leu Ser
            100                 105                 110

Ser Ser Ser Ser Gly Leu Ser Ala Leu Val Lys Ala Leu Asn Ala Arg
        115                 120                 125

Phe Lys Leu Gly Leu Asn Arg Ser Gln Leu Ala Gln Glu Ala Lys Phe
130                 135                 140

Ala Ser Gly Ser Ser Arg Ser Phe Tyr Gly Pro Leu Gly Ala Trp
145                 150                 155                 160

Asp Lys Asp Ser Gly Leu Ile Tyr Pro Val Glu Thr Gly Leu Lys Leu
                165                 170                 175

Ala Met Ile Cys Leu Val Leu Cys Asp Lys Lys Pro Ile Ser Ser
            180                 185                 190

Arg Asp Gly Met Lys Leu Cys Val Glu Thr Ser Thr Thr Phe Asp Asp
        195                 200                 205

Trp Val Arg Gln Ser Glu Lys Asp Tyr Gln Asp Met Leu Val Tyr Leu
210                 215                 220

Lys Ala Asn Asp Phe Ala Lys Val Gly Glu Leu Thr Glu Lys Asn Ala
225                 230                 235                 240

Leu Ala Met His Ala Thr Thr Lys Thr Ala Ser Pro Ala Phe Ser Tyr
                245                 250                 255

Leu Thr Asp Ala Ser Tyr Glu Ala Met Asp Phe Val Arg Gln Leu Arg
            260                 265                 270

Glu Gln Gly Glu Ala Cys Tyr Phe Thr Met Asp Ala Gly Pro Asn Val
        275                 280                 285

Cys Val Leu Cys Gln Glu Lys Asp Leu Asp His Leu Ser Glu Ile Leu
    290                 295                 300

Gly Gln Arg Tyr Arg Met Ile Val Ser Lys Ser Lys Asp Leu Ser Gln
305                 310                 315                 320

Asp Gly Cys Cys
```

3-HYDROXYISOVALERATE (HIV) SYNTHASE VARIANTS

CROSS-REFERENCE TO RELATED APPLICATIONS

This application is a § 371 National Stage Application of PCT/EP2014/078120, filed Dec. 17, 2014, which claims priority to EP 13199884.1, filed Dec. 31, 2013. All of these documents (PCT/EP2014/078120 and EP 13199884.1) are hereby incorporated by reference in their entirety.

The present invention relates to 3-hydroxyisovalerate (HIV) synthase variants having improved activity in converting acetone and a compound which provides an activated acetyl group into 3-hydroxyisovalerate (HIV). Moreover, the present invention also in particular relates to methods for the production of isobutene from acetone utilizing the HIV synthase variants of the present invention.

A large number of chemical compounds are currently derived from petrochemicals. Isobutene is currently produced at large scale by petrochemically cracking crude oil. Isobutene is a key precursor for numerous chemicals since isobutene, due to the presence of its reactive double bond, can take part in various kinds of chemical reactions resulting in a great variety of products.

For the past two decades, genetic engineering technologies have made possible the modification of the metabolism of microorganisms, and hence their use to produce key substances which they would otherwise produce at a low yield. By enhancing naturally occurring metabolic pathways, these technologies open up new ways to bio-produce numerous compounds of industrial relevance. Several industrial compounds such as amino-acids for animal feed, biodegradable plastics or textile fibres are now routinely produced using genetically modified organisms. There are however no bio-processes using microorganisms in place for the large scale production of the major petrochemically derived molecules, in particular isobutene, since no microorganisms are known as natural producers of isobutene even in small quantities. Given the large amounts of products produced using isobutene as a precursor and the increasing environmental concerns and the limited resources for producing isobutene using chemical processes, there is a need to provide alternative, environmentally-friendly and sustainable processes for the production of isobutene.

Recent work has shown that it is possible to generate isobutene on a bio-based fermentative production from acetone. Acetone can be naturally produced by various organisms, including bacteria from the genus *Clostridium*, *Bacillus* or *Pseudomonas*, such as *Clostridium acetobutylicum*, *Clostridium beijerinckii*, *Clostridium cellulolyticum*, *Bacillus polymyxa* or *Pseudomonas putida*. In the meantime also recombinant organisms, for example genetically modified *E. coli* cells, have been reported which have the capacity to synthesize acetone (Bermejo et al., Appl. Environ. Microbiol. 64 (1998); 1079-1085; Hanai et al., Appl. Environ. Microbiol. 73 (2007), 7814-7818). Recently, artificially created metabolic pathways have been described which make use of acetone as an intermediate in order to produce isobutene. For example, WO 2011/032934 describes an enzymatic method for the production of 3-hydroxy-3-methylbutyric acid (also referred to as beta-hydroxyisovalerate, 3-hydroxyisovalerate (HIV)) from acetone and a compound which provides an activated acetyl group. The produced HIV can then be further converted into isobutene via an enzymatically catalyzed phosphorylation/decarboxylation reaction (WO 2010/001078 and WO 2012/052427) via 3-phosphonoxy-isovalerate (PIV).

WO 2011/032934 describes the above enzymatic method for the production of 3-hydroxyisovalerate (HIV; 3-hydroxy-3-methylbutyric acid; also referred to as beta-hydroxyisovalerate) from acetone involving the enzymatic conversion of acetone and a compound which provides an activated acetyl group into HIV. The conversion makes use of an enzyme which is capable of catalyzing the formation of a covalent bond between the carbon atom of the oxo (i.e., the C=O) group of acetone and the carbon atom ($C^2$) corresponding to the methyl group of the compound which provides the activated acetyl group and this conversion can be achieved by, e.g., employing an enzyme having the activity of a HMG CoA synthase (EC 2.3.3.10) or an enzyme having the activity of a C—C bond cleavage/condensation lyase, such as a HMG CoA lyase (EC 4.1.3.4), or a PksG protein.

The synthesis of isobutene (in the following also referred to as IBN) (summarized in FIG. 1) can be achieved by first enzymatically converting acetone and a compound which provides an activated acetyl group into 3-hydroxyisovalerate (HIV) and then further converting HIV into isobutene. The latter reaction comprises two steps, i.e., the activation of HIV with ATP to form 3-phosphonoxy-isovaleric acid (also referred to as PIV or 3-methyl-3-phosphonoxy-butyric acid) which is, e.g., achieved by an enzymatically catalysed phosphorylation reaction as described in WO 2012/052427, and the subsequent conversion of PIV into isobutene (also referred to as IBN) is, e.g., achieved by an enzymatically catalyzed decarboxylation reaction as described, e.g., in WO 2010/001078 and WO 2012/052427. In the following, whenever reference is made to a "HIV phosphorylase" and a "PIV decarboxylase" (the latter is alternatively also referred to as "IBN synthetase") reference is made to enzymes which are capable of catalyzing the conversion of 3-hydroxyisovalerate (HIV) into 3-phosphonoxy-isovaleric acid (PIV) as defined further below and to enzymes which are capable of catalyzing the conversion of 3-phosphonoxy-isovaleric acid (PIV) into isobutene (IBN) as defined further below, respectively.

However, the turnover rate of the enzymes occurring in nature, such as HMG CoA synthase (EC 2.3.3.10) as described in WO2011/032934, for the above enzymatic production of HIV from acetone involving the enzymatic conversion of acetone and a compound which provides an activated acetyl group into HIV is not yet suitable for industrial applications and hence, there is a need for improvements, i.e., to increase the activity of such enzymes, in particular as regards to a further increase in efficiency of the above processes so as to make them more suitable for industrial purposes.

The present invention addresses this need by providing the embodiments as defined in the claims.

Thus, the present invention provides a variant of a 3-hydroxyisovalerate (HIV) synthase showing an improved activity in converting acetone and a compound which provides an activated acetyl group characterized by the following formula (I):

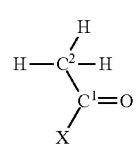

into 3-hydroxyisovalerate over the corresponding HIV synthase from which it is derived, wherein X is selected from the group consisting of S—CH2-CH2-NH—CO—CH2-CH2-NH—CO—CH(OH)—C(CH3)2-CH2-O—PO2H—O—PO2H—C10H13N5O7P (coenzyme A), S—CH2-CH2-NH—CO—CH2-CH2-NH—CO—CH(OH)—C(CH3)2-CH2-O—PO2H-polypeptide (acyl-carrier protein), S—CH2-CH2-NH—CO—CH2-CH2-NH—CO—CH(OH)—C(CH3)2-CH2-OH (pantetheine), S—CH$_2$—CH$_2$—NH—CO—CH$_3$ (N-acetyl-cysteamine), S—CH$_3$ (methane thiol), S—CH2-CH(NH2)-CO2H (cysteine), S—CH2-CH2-CH(NH2)-CO2H (homocysteine), S—CH2-CH(NH—C5H8NO3)-CO—NH—CH2-CO2H (glutathione), S—CH$_2$—CH$_2$—SO$_3$H (coenzyme M) and OH (acetic acid). Preferably, X is coenzyme A.

Acetone is represented by the following formula: CH$_3$—(C=O)—CH$_3$. Moreover, whenever reference is made to a compound which provides an activated acetyl group such a compound is characterized by the following formula (I):

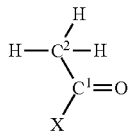

wherein X is selected from the group consisting of S—CH2-CH2-NH—CO—CH2-CH2-NH—CO—CH(OH)—C(CH3)2-CH2-O—PO2H—O—PO2H—C10H13N5O7P (coenzyme A), S—CH2-CH2-NH—CO—CH2-CH2-NH—CO—CH(OH)—C(CH3)2-CH2-O—PO2H-polypeptide (acyl-carrier protein), S—CH2-CH2-NH—CO—CH2-CH2-NH—CO—CH(OH)—C(CH3)2-CH2-OH (pantetheine), S—CH$_2$—CH$_2$—NH—CO—CH$_3$ (N-acetyl-cysteamine), S—CH$_3$ (methane thiol), S—CH2-CH(NH2)-CO2H (cysteine), S—CH2-CH2-CH(NH2)-CO2H (homocysteine), S—CH2-CH(NH—C5H8NO3)-CO—NH—CH2-CO2H (glutathione), S—CH$_2$—CH$_2$—SOaH (coenzyme M) and OH (acetic acid). In a preferred embodiment, whenever reference is made to a compound which provides an activated acetyl group such a compound is characterized by the following formula (I):

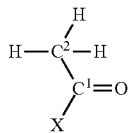

wherein X is S—CH2-CH2-NH—CO—CH2-CH2-NH—CO—CH(OH)—C(CH3)2-CH2-O—PO2H—O—PO2H—C10H13N5O7P (coenzyme A).

Thus, the compound to be converted by an enzyme variant of the present invention is acetone leading to 3-hydroxyisovalerate (HIV). An improved enzyme variant or an enzyme variant capable of catalyzing a reaction with increased activity is defined as an enzyme variant which differs from the wildtype enzyme and which catalyzes the respective conversion of acetone into 3-hydroxyisovalerate (HIV) as defined above so that the specific activity of the enzyme variant is higher than the specific activity of the wildtype enzyme for at least one given concentration of acetone (preferably any acetone concentration higher than 0 M and up to 1 M). A specific activity is defined as the number of moles of substrate converted to moles of product by unit of time by mole of enzyme. Kat (turnover number) is the specific activity at saturating concentration of substrate.

In particular, the present invention provides a corresponding variant of an HIV synthase which is characterized in that it is capable of converting acetone and a compound which provides an activated acetyl group characterized by the following formula (I):

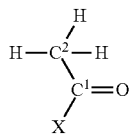

into 3-hydroxyisovalerate (HIV) with a turnover rate of at least $0.93 \times 10^{-2}$ s$^{-1}$ of acetone into HIV, wherein X is selected from the group consisting of S—CH2-CH2-NH—CO—CH2-CH2-NH—CO—CH(OH)—C(CH3)2-CH2-O—PO2H—O—PO2H—C10H13N5O7P (coenzyme A), S—CH2-CH2-NH—CO—CH2-CH2-NH—CO—CH(OH)—C(CH3)2-CH2-O—PO2H-polypeptide (acyl-carrier protein), S—CH2-CH2-NH—CO—CH2-CH2-NH—CO—CH(OH)—C(CH3)2-CH2-OH (pantetheine), S—CH$_2$—CH$_2$—NH—CO—CH$_3$ (N-acetyl-cysteamine), S—CH$_3$ (methane thiol), S—CH2-CH(NH2)-CO2H (cysteine), S—CH2-CH2-CH(NH2)-CO2H (homocysteine), S—CH2-CH(NH—C5H8NO3)-CO—NH—CH2-CO2H (glutathione), S—CH$_2$—CH$_2$—SO$_3$H (coenzyme M) and OH (acetic acid).

The present invention provides enzymes which are capable of converting acetone into 3-hydroxyisovalerate with improved activity, compared to the enzyme represented by SEQ IN NO:1. In the context of the present invention, an "improved activity" means that the activity of the enzyme in question is at least 10%, preferably at least 20%, more preferably at least 30% or 50%, even more preferably at least 70% or 80% and particularly preferred at least 90% or 100% higher than that of the enzyme from which the variant is derived, preferably higher than that the enzyme represented by SEQ ID NO:1. In even more preferred embodiments the improved activity may be at least 150%, at least 200%, at least 300%, at least 750% or at least 1000% higher than that of the corresponding enzyme from which the variant is derived, preferably higher than that of the enzyme represented by SEQ ID NO:1. In a particularly preferred embodiment, the activity is measured by using an assay with purified enzyme and chemically synthesized substrates, as described below. The improved activity of a variant can be measured as a higher 3-hydroxyisovalerate production in a given time under defined conditions, compared with the parent enzyme. This improved activity can result from a higher turnover number, e.g. a higher kcat value. It can also result from a lower Km value. It can also result from a higher kcat/Km value. Finally, it can result from a higher solubility, or stability of the enzyme. The degree of improvement can be measured as the improvement in 3-hydroxyisovalerate production. The degree of improvement can also be measured in terms of kcat improvement, of kcat/Km improvement, or in terms of Km decrease, or in terms of soluble protein production.

In particular, in accordance with the above, the present invention provides enzymes which are capable of converting acetone into 3-hydroxyisovalerate with a turnover rate of at least $0.93 \times 10^{-2}$ s$^{-1}$ of acetone into 3-hydroxyisovalerate.

Such enzymes can be provided by effecting mutations at specific positions in an HMG CoA synthase and the variants obtained by effecting such mutations show an improved activity in catalyzing the conversion of acetone into 3-hydroxyisovalerate. In a preferred embodiment, the enzyme is capable of converting acetone into 3-hydroxyisovalerate with a turnover rate of at least $1.86 \times 10^{-2}$ s$^{-1}$ and more preferably of at least $4.65 \times 10^{-2}$ s$^{-1}$ of acetone into 3-hydroxyisovalerate. In a particularly preferred embodiment the enzyme has a turnover rate of at least $0.93 \times 10^{-1}$ s$^{-1}$ of acetone into 3-hydroxyisovalerate and in a particularly preferred embodiment of at least $1.86 \times 10^{-2}$ s$^{-1}$. In a most preferred embodiment, the enzyme has a turnover rate of at least $2.79 \times 10^{-1}$ s$^{-1}$ and even more preferably of at least 0.93 s$^{-1}$ of acetone into 3-hydroxyisovalerate. The corresponding wild-type enzyme has a turnover rate of about $0.93 \times 10^{-2}$ s$^{-1}$ of acetone into 3-hydroxyisovalerate.

In another embodiment, the present invention provides enzymes which are capable of converting acetone into 3-hydroxyisovalerate with a turnover rate (i.e., a $K_{cat}$-value) which is at least 1.5 times as high compared to the turnover rate of the corresponding wild type enzyme having the amino acid sequence as shown in SEQ ID NO:1. In a preferred embodiment, the enzymes which are capable of converting acetone into 3-hydroxyisovalerate have a turnover rate (i.e., a $K_{cat}$-value) which is at least 2 times, at least 3 times, at least 5 times or even at least 10 times as high compared to the turnover rate of the corresponding wild type enzyme having the amino acid sequence as shown in SEQ ID NO:1. In other preferred embodiments, the enzymes which are capable of converting acetone into 3-hydroxyisovalerate have a turnover rate (i.e., a $K_{cat}$-value) which is at least 20 times or at least 30 times as high compared to the turnover rate of the corresponding wild type enzyme having the amino acid sequence as shown in SEQ ID NO:1. In even more preferred embodiments, the turnover rate is at least 100 times or even at least 500 times as high compared to that of the corresponding wild type enzyme having the amino acid sequence as shown in SEQ ID NO:1.

The turnover rate of an enzyme capable of converting acetone into 3-hydroxyisovalerate may be determined by methods known to the person skilled in the art. In one embodiment, this turnover rate is determined as described in the Examples appended hereto. In a particular embodiment this turnover rate can be measured by incubating the enzyme, preferably a cell lysate containing the overexpressed recombinant protein, in vitro. Alternatively, a purified enzyme can be used.

More specifically, the enzyme whose turnover rate is to be assessed may be determined as outlined in the following: Michaelis-Menten $k_{cat}$ and $K_m$ steady state kinetics constants for the reaction of conversion of acetone into 3-hydroxyisovalerate (HIV) may be determined using the following protocol:

The HIV synthase variant (and the corresponding wild type HIV synthase as a control) is sub-cloned into the commercial Novagen peT-25b+ bacterial expression vector and the plasmid DNA containing the sequence coding for the wild type HIV synthase and variants showing increased HIV synthesis activity, respectively, are transformed into BL21 (DE3) competent cells and plated out onto LB agar petri dishes supplemented with the appropriate antibiotic. Cells are grown overnight at 30° C. and isolated transformants are picked and used to inoculate autoinduction medium (ZYM medium, Studier F. W; Protein Expr. Purif. 41 (2005), 207-234). The cultures are then grown overnight at 30° C. for 20-22 hours in shaking incubator. The cells containing the overexpressed recombinant enzyme are pelleted and stored at −80° C. overnight before the frozen cell pellets are being thawed on ice and resuspended in adequate amounts of Bugbuster (Merck Novagen). The cell suspension is incubated for 10 minutes at room temperature followed by 20 minutes on ice to allow cell lysis to proceed. Cell lysates are clarified by centrifugation and His6 tagged enzymes are purified by affinity chromatography (Macherey Nagel). Protein concentration was determined by direct UV 280 nm measurement on the NanoDrop 1000 sectrophotometer (Thermo Scientific). The amount of the enzyme variant present in the clarified cell lysate is estimated on SDS-PAGE gel against a BSA calibration curve using gel densitometry. Enzymatic reactions are set up in 2 ml glass vials with 40 µg of purified enzyme mixed with HIV production buffer (50 mM Tris, 10 mM MgCl2, 20 mM KCl, 0.5 mM DTT, 4 mM Ac-CoA) supplemented with a range of acetone concentrations (0 to 1200 mM). The vials are sealed and incubated for 2 hours at 37° C. followed by a 5 minutes deactivation at 80° C. to stop the reaction. The enzymatic reaction is clarified by centrifugation and supernatant is transferred to a fresh tube to which isobutene (IBN) production reagents are added (50 mM Tris pH 7.5, 5 mM ATP, 20 mM KCl, 5 µg HIV phosphorylase and 85 µg PIV decarboxylase).

As an "HIV phosphorylase", i.e., an enzyme capable of catalyzing the conversion of the 3-hydroxyisovalerate (HIV) into 3-phosphonoxy-isovaleric acid (PIV), a mevalonate diphosphate decarboxylase (EC 4.1.1.33) isolated from *Thermoplasma acidophilum* may be used (Uniprot entry for the wildtype sequence Q9H1N1-THEAC) having an amino acid substitution at position 200 (L200E) including a N terminal His6-tag wherein the HIV phosphorylase has the amino acid sequence as shown in SEQ ID NO:2. As an "PIV decarboxylase", i.e., an enzyme capable of catalyzing the conversion of PIV into isobutene (IBN), a mevalonate diphosphate decarboxylase (EC 4.1.1.33) isolated from *Streptococcus mitis* strain B6 may be used (Uniprot entry for the wildtype sequence D3HAT7-STRM6) having amino acid substitutions at positions 24, 118, 121, 159, 173, 177, 282, 291, and 297 (K24R C118L Y121R E159L M173C E177C K282C E291D F297L) including a N terminal His6-tag wherein the PIV decarboxylase has the amino acid sequence as shown in SEQ ID NO:3. The HIP phosphorylase and PIV decarboxylase may be produced as follows: the coding sequences of both the above described genes are sub-cloned into peT25b(+) (Merck-Novagen) and the resulting expression vectors are transformed into BL21(DE3) according to standard procedures. Single transformants are used to inoculate 1 liter of ZYM-5052 autodinduction medium (Studier F W, Prot. Exp. Pur. 41, (2005), 207-234). Cells are grown in a shaking incubator for 20-22 hours at 30° C. for the above *S. mitis* MDP and 8 hours at 37° C. followed by a 16 hours incubation at 28° C. for the above *T. acidophilum* MDP. Cells are pelleted and stored at −80° C. until further processed. For the cell lysis, cells pellets are resuspended in 40 ml of Bugbuster reagent (Merck-Novagen) supplemented with 100 µl of lysonase 10 minutes at room temperature followed by a further 20-minutes incubation at 4° C. Cell lysates are clarified by centrifugation (30-40 minutes at 10,000 g) and filtered through at 0.22 µm filter. Purification of the N-term His-tagged proteins of interest from these cell lysates is carried out by IMAC (Immobilized Metal ion Affinity Chromatography) on a 5 ml HisTrap HP column using a ÄKTA Purifier UPC 100 (GE Healthcare) according to the manufacturer's recommendations. The eluted proteins are concentrated and desalted by ultrafiltration using Millipore Amicon Ultra-15 concentrated.

The conversion of 3-hydroxyisovalerate (HIV) into isobutene (IBN) for reactions as well as standards is performed for 24 hours at 37° C. In order to quantify by gas chromatography the amount of isobutene produced 100 μl of headspace gases from each enzymatic reaction is injected (Injection parameters: 250° C.; split=10) in a Brucker GC-450 system equipped with a Flame ionization detector (FID) (250'C; 28 ml·min$^{-1}$ H$_2$; 30 ml·min$^-$ N$_2$; 300 ml·min$^{-1}$ synthetic air)). Compounds present in samples are separated by chromatography using a RTX-1 column (15m×0.32 mm; Restek, France) at 100° C. with a 1 ml·min$^{-1}$ constant flow of carrier gas (nitrogen 5.0, Messer, France) and peak area of isobutene is calculated for samples and standards. In order to quantify absolute amounts of isobutene (IBN) and 3-hydroxyisovalerate (HIV) produced a range of concentrations of HIV (0.25 to 2 mM) is subjected to enzymatic conversion to IBN as applied to samples and a range of concentrations of pure IBN (1 to 100,000 ppm) is used to calibrate the gas chromatograph. Both the calibrations curves are linear in this range of isobutene concentrations and HIV concentrations. The production rates of HIV (moles of HIV/mole enzyme/sec) are plotted as a function of the concentration of acetone and the curve is fitted using Michaelis Menten equation:

$$V = \frac{(Vmax \times [\text{substrate}])}{(Km + [\text{substrate}])}$$

to extract the k$_{cat}$(s$^{-1}$) and the K$_m$ values (mM).

As mentioned, it has recently been shown that it is possible to produce HIV enzymatically from acetone and a compound which provides an activated acetyl group (see WO2011/032934). An enzyme which is capable of converting acetone into HIV is referred herein as an "HIV synthase". An HIV synthase is in particular characterized in that it is capable of catalyzing the formation of a covalent bond between the carbon atom of the oxo (i.e., the C=O group of acetone and the carbon atom (C$^2$) corresponding to the methyl group of the compound which provides the activated acetyl group. The compound which provides the activated acetyl group is characterized by the following formula:

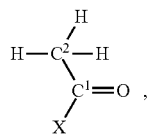

wherein X is selected from the group consisting of S—CH2-CH2-NH—CO—CH2-CH2-NH—CO—CH(OH)—C(CH3)2-CH2-O—PO2H—O—PO2H—C10H13N5O7P (coenzyme A), S—CH2-CH2-NH—CO—CH2-CH2-NH—CO—CH(OH)—C(CH3)2-CH2-O—PO2H-polypeptide (acyl-carrier protein), S—CH2-CH2-NH—CO—CH2-CH2-NH—CO—CH(OH)—C(CH3)2-CH2-OH (pantetheine), S—CH$_2$—CH$_2$—NH—CO—CH$_3$ (N-acetylcysteamine), S—CH$_3$ (methane thiol), S—CH2-CH(NH2)-CO2H (cysteine), S—CH2-CH2-CH(NH2)-CO2H (homocysteine), S—CH2-CH(NH—C5H8NO3)-CO—NH—CH2-CO2H (glutathione), S—CH$_2$—CH$_2$—SO$_3$H (coenzyme M) and OH (acetic acid). In a preferred embodiment, X is S—CH2-CH2-NH—CO—CH2-CH2-NH—CO—CH(OH)—C(CH3)2-CH2-O—PO2H—O—PO2H—C10H13N5O7P (coenzyme A). Enzymes for which it has been described that they can be employed in the conversion of acetone into HIV include enzymes having the activity of a HMG CoA synthase (EC 2.3.3.10) or enzymes having the activity of a C—C bond cleavage/condensation lyase, such as a HMG CoA lyase (EC 4.1.3.4), or PksG proteins. Herein, these enzymes having the capability to produce HIV enzymatically from acetone and a compound which provides an activated acetyl group are collectively referred to as "HIV synthases".

In a preferred embodiment, the HIV synthase, from which the variants of the present invention are derived is an enzyme with the activity of an HMG CoA synthase. The term "HMG CoA synthase" refers to an enzyme which is classified in the EC number 2.3.3.10 and in particular to an enzyme which is able to catalyze the reaction where acetyl-CoA condenses with acetoacetyl-CoA to form 3-hydroxy-3-methylglutaryl-CoA (HMG-CoA). The precise reaction mechanism has been described by Chun et al. (Biochem. 39 (2000), 14670-14681), Sutherlin et al. (J. Bacterio. 184 (2002), 4065-4070) and Wang et al. (J. Biol. Chem. 279 (2004), 40283-40288). This activity can be measured by methods well known in the art. One possible and preferably used assay is described, e.g. in Clinkenbeard et al. (J. Biol. Chem 250 (1975), 3108-3116). In this assay HMG-CoA synthase activity is measured by monitoring the decrease in the absorbance at 303 nm that accompanies the acetyl-CoA-dependent disappearance of the enolate form of acetoacetyl-CoA. Preferably HMG CoA synthase activity is assayed as described in Example 7.

More specifically, the activity to for the condensation of acetyl-CoA with acetoacetyl-CoA to form 3-hydroxy-3-methylglutaryl-CoA (HMG-CoA) can be measured by incubating the enzyme, preferably a cell lysate containing the (overexpressed) recombinant protein, in vitro. Alternatively, a purified enzyme can be used. More specifically, the enzyme whose activity to condense acetyl-CoA with acetoacetyl-CoA to from HMG-CoA is to be assessed may be produced as outlined in the following: The sequence coding for the wild type version or variants of the HIV synthase is subcloned in the pET25b+ expression vector (Novagen) using standard molecular biology techniques. The expression constructs are transformed into BL21(DE3) competent cells (Novagen). Isolated clones are used to inoculate 50 ml of auto-induction medium (Studier F. W, Protein Expr. Purif. 41 (2005), 207-234) supplemented with the appropriate antibiotic and grown overnight at 30° C. for 20-22 hours in a shaking incubator set at 700 rpm. The cells are pelleted and stored at −80° C. for at least overnight.

The enzymatic assay is set up using clarified cell lysate: the frozen cell pellets containing the overexpressed recombinant enzyme are resuspended in a lysis buffer (BugBuster, Merck Novagen). The suspension is incubated for 10 minutes at room temperature followed by 20 minutes on ice. Cell lysates are clarified by centrifugation and His6 tagged enzymes are purified from clarified lysates by affinity chromatography (Macherey Nagel), concentrated by centrifugation on ultrafiltration membranes (Amicon ultra, Millipore) and desalted by size exclusion chromatography (Zeba spin columns, Perbio Science). The amount of the enzyme variant present in the concentrated soluble fraction is estimated on SDS-PAGE gel against a BSA calibration curve.

HMG CoA synthase activity of the purified enzymes is characterized in vitro by methods well known in the art, preferably by using the assay as described, e.g. in Clinkenbeard et al. (J. Biol. Chem 250 (1975), 3108-3116). In this assay HMG-CoA synthase activity is measured by monitoring the decrease in the absorbance at 303 nm that accompanies the acetyl-CoA-dependent disappearance of the enolate form of acetoacetyl-CoA. In order to measure the decrease in the absorbance at 303 nm that accompanies the acetyl-CoA-dependent disappearance of the enolate form of acetoacetyl-CoA, the following three items are prepared individually on ice:

Purified enzymes to be tested are diluted (1.6 mg/ml in 50 mM Tris pH 7.5 buffer)

Reaction buffer (50 mM Tris pH 7.5, 20 mM $MgCl_2$, 0.5 mM DTT, 0.2 mM AcCoA)

Substrate (1 mM AcAcCoA in 50 mM Tris pH 7.5)

Reagents are then mixed together on ice and immediately transferred to a spectrophotometer chamber set at 30° C. with shaking. Decrease in absorbency at 303 nm is monitored for 30 min for assay reactions and appropriate controls in the absence of enzymes or substrates. Enzyme activity (in μmole/mg of enzyme/minute) is calculated from the slope of the curve obtained from the change in Abs(303 nm) in time.

Thus, in the context of the present invention, the term "HMG CoA synthase" or "a protein/enzyme having the activity of a HMG CoA synthase" refers to any enzyme which is classified in the EC number EC 2.3.3.10 (formerly, HMG-CoA synthase has been classified as EC 4.1.3.5 but has been transferred to EC 2.3.3.10), in particular it refers to any enzyme which is able to catalyze the reaction where acetyl-CoA condenses with acetoacetyl-CoA to form 3-hydroxy-3-methylglutaryl-CoA (HMG-CoA) and the term also refers to any enzyme which is derived from such a HMG CoA synthase and which is capable of catalyzing the conversion of acetone and a compound which provides an activated acetyl group as defined above, preferably acetyl CoA, into 3-hydroxy-3-methylbutyrate.

HMG CoA synthase is part of the mevalonate pathway. Two pathways have been identified for the synthesis of isopentenyl pyrophosphate (IPP), i.e. the mevalonate pathway and the glyceraldehyde 3-phosphate-pyruvate pathway. HMG CoA synthase catalyzes the biological Claisen condensation of acetyl-CoA with acetoacetyl-CoA and is a member of a superfamily of acyl-condensing enzymes that includes beta-ketothiolases, fatty acid synthases (beta-ketoacyl carrier protein synthase) and polyketide synthases.

As mentioned above, it has been shown that the HMG CoA synthases can act to produce HIV enzymatically from acetone and a compound which provides an activated acetyl group (WO02011/032934). As will be outlined in more detail below, the present invention now provides improved variants of enzymes which are capable of converting acetone and a compound which provides an activated acetyl group into HIV. The inventors used as a model enzyme the HMG CoA synthase of Mus musculus the amino acid of which is shown in SEQ ID NO:1 and could show that it is possible to provide variants of this enzyme which show increased activity with respect to the enzymatic conversion to produce HIV from acetone and a compound which provides an activated acetyl group. SEQ ID NO:1 shows the 520 amino acid residues long protein of *Mus musculus* registered in UniProt under accession number Q3UWQ9 encoded by gene Hmgcs1. There exists another entry in Uniprot (accession Q8JZK9) for the mouse HMG CoA synthase also encoded by the same Hmgcs1 gene. The corresponding protein differs from the amino acid sequence shown in SEQ ID NO:1 by showing an asparagine at position 107 instead of a lysine.

HMG CoA synthase has been described for various organisms. Also amino acid and nucleic acid sequences encoding HMG CoA synthases from numerous sources are available. Generally, the sequences only share a low degree of overall sequence identity. For example, the enzymes from *Staphylococcus* or *Streptococcus* show only about 20% identity to those of human and avian HMG CoA synthase. In some sources it is reported that the bacterial HMG CoA synthases and their animal counterparts exhibit only about 10% overall sequence identity (Sutherlin et al., J. Bacteriol. 184 (2002), 4065-4070). However, the amino acid residues involved in the acetylation and condensation reactions are conserved among bacterial and eukaryotic HMG CoA synthases (Campobasso et al., J. Biol. Chem. 279 (2004), 44883-44888). The three-dimensional structure of three HMG CoA synthase enzymes has been determined and the amino acids crucial for the enzymatic reaction are in principle well characterized (Campobasso et al., loc. cit.; Chun et al., J. Biol. Chem. 275 (2000), 17946-17953; Nagegowda et al., Biochem. J. 383 (2004), 517-527; Hegardt, Biochem. J. 338 (1999), 569-582). In eukaryotes there exist two forms of the HMG CoA synthase, i.e. a cytosolic and a mitochondrial form. The cytosolic form plays a key role in the production of cholesterol and other isoprenoids and the mitochondrial form is involved in the production of ketone bodies.

In principle any HMG CoA synthase enzyme can be used in the context of the present invention, in particular from prokaryotic or eukaryotic organisms.

Prokaryotic HMG CoA synthases are described, e.g., from *Staphylococcus aureus* (Campobasso et al., loc. cit.; Uniprot accession number Q9FD87), *Staphylococcus epidermidis* (Uniprot accession number Q9FD76), *Staphylococcus haemolyticus* (Uniprot accession number Q9FD82), *Enterococcus faecalis* (Sutherlin et al., loc. cit.; Uniprprot accession number Q9FD71), *Enterococcus faecium* (Uniprot accession number Q9FD66), *Streptococcus pneumonia* (Uniprot accession number Q9FD56), *Streptococcus pyogenes* (Uniprot accession number Q9FD61) and *Methanobacterium thermoautotrophicum* (NCBI accession number AE000857), *Borrelia burgdorferi* (NCBI accession number BB0683).

Eukaryotic HMG CoA synthases are described, e.g., from fungi, such as *Schizosaccharomyces pombe* (accession numbers U32187 and P54874), *Saccharomyces cerevisiae* (accession number P54839), plants, such as *Arabidopsis thaliana* (accession numbers X83882 and P54873), *Pinus sylvestris* (accession number X96386) and animals, such as *Caenorhabditis elegans* (accession number P54871), *Mus musculus* (mitochondrial; accession number P54869 and Hegardt, Biochem. J. 338 (1999), 569-582), *Rattus norvegicus* (mitochondrial: accession number P22791 and Hegardt, Biochem. J. 338 (1999); cytosolic: accession number P17425), 569-582), Chinese hamster (*Cricetulus griseus*: accession number P13704), *Sus scrofa* (mitochondrial; accession number U90884 and Hegardt, Biochem. J. 338 (1999), 569-582), *Homo sapiens* (mitochondrial: accession number P54868 and Hegardt, Biochem. J. 338 (1999), 569-582; cytosolic: accession number Q01581), *Blattella germanica* (cytosolic form 1; accession number P54961), *Blattella germanica* (cytosolic form 2; accession number P54870) and *Gallus gallus* (cytosolic; accession number P23228).

In view of the fact that HMG CoA synthases catalyze a key metabolic step in the mevalonate pathway they are, therefore, present in a very large range of organisms. Alignment studies (pBLAST using BLOSUM62 matrix, threshold=10) return a very large number of sequences, many of them displaying high level identity to SEQ ID NO:1 as in the following Tables 1, 2 and 3.

TABLE 1 pBLAST results filtered on sequences showing >90% sequence identity to
SEQ ID NO: 1 as identified using BLOSUM62 matrix and Threshold = 1.

| Entry name UniprotKb | Accession | Organism | Entry date | Last database update | Entry version | Seq. version | % identity with SEQ ID NO: 1 |
|---|---|---|---|---|---|---|---|
| Q8JZK9 | HMCS1_MOUSE | *Mus musculus* (Mouse) | 15/03/05 | 24/07/13 | 100 | 1 | 99% |
| Q52MA3 | Q52MA3_XENLA | *Xenopus laevis* (African clawed frog) | 24/05/05 | 29/05/13 | 31 | 1 | 99% |
| Q8K0I5 | Q8K0I5_MOUSE | *Mus musculus* (Mouse) | 01/10/02 | 26/06/13 | 52 | 1 | 99% |
| Q3UJ70 | Q3UJ70_MOUSE | *Mus musculus* (Mouse) | 11/10/05 | 26/06/13 | 47 | 1 | 99% |
| Q3UKE7 | Q3UKE7_MOUSE | *Mus musculus* (Mouse) | 11/10/05 | 26/06/13 | 46 | 1 | 99% |
| Q8C5F4 | Q8C5F4_MOUSE | *Mus musculus* (Mouse) | 01/03/03 | 26/06/13 | 60 | 1 | 99% |
| P17425 | HMCS1_RAT | *Rattus norvegicus* (Rat) | 01/08/90 | 24/07/13 | 117 | 1 | 98% |
| Q3UJQ2 | Q3UJQ2_MOUSE | *Mus musculus* (Mouse) | 11/10/05 | 03/04/13 | 40 | 1 | 98% |
| G3HMY0 | G3HMY0_CRIGR | *Cricetulus griseus* (Chinese hamster) (*Cricetulus barabensis griseus*) | 16/11/11 | 01/05/13 | 7 | 1 | 97% |
| P13704 | HMCS1_CRIGR | *Cricetulus griseus* (Chinese hamster) (*Cricetulus barabensis griseus*) | 01/01/90 | 03/04/13 | 81 | 1 | 97% |
| I3M6J1 | I3M6J1_SPETR | *Spermophilus tridecemlineatus* (Thirteen-lined ground squirrel) (*Ictidomys tridecemlineatus*) | 11/07/12 | 26/06/13 | 6 | 1 | 96% |
| G1SJY8 | G1SJY8_RABIT | *Oryctolagus cuniculus* (Rabbit) | 19/10/11 | 03/04/13 | 9 | 1 | 96% |
| F6UT64 | F6UT64_CALJA | *Callithrix jacchus* (White-tufted-ear marmoset) | 27/07/11 | 03/04/13 | 11 | 1 | 95% |
| F6SD16 | F6SD16_HORSE | *Equus caballus* (Horse) | 27/07/11 | 03/04/13 | 12 | 1 | 95% |
| G7P7G3 | G7P7G3_MACFA | *Macaca fascicularis* (Crab-eating macaque) (Cynomolgus monkey) | 25/01/12 | 06/03/13 | 5 | 1 | 95% |
| F7HQ90 | F7HQ90_MACMU | *Macaca mulatta* (Rhesus macaque) | 27/07/11 | 03/04/13 | 15 | 1 | 95% |
| E2QX73 | E2QX73_CANFA | *Canis familiaris* (Dog) (*Canis lupus familiaris*) | 30/11/10 | 29/05/13 | 19 | 1 | 95% |
| G5BCR6 | G5BCR6_HETGA | *Heterocephalus glaber* (Naked mole rat) | 14/12/11 | 06/03/13 | 7 | 1 | 95% |
| H9ETD6 | H9ETD6_MACMU | *Macaca mulatta* (Rhesus macaque) | 16/05/12 | 06/03/13 | 4 | 1 | 95% |
| G1RHH9 | G1RHH9_NOMLE | *Nomascus leucogenys* (Northern white-cheeked gibbon) (*Hylobates leucogenys*) | 19/10/11 | 01/05/13 | 11 | 1 | 95% |
| G1LB44 | G1LB44_AILME | *Ailuropoda melanoleuca* (Giant panda) | 19/10/11 | 03/04/13 | 10 | 1 | 95% |
| M3YSL2 | M3YSL2_MUSPF | *Mustela putorius furo* (European domestic ferret) (*Mustela furo*) | 01/05/13 | 29/05/13 | 2 | 1 | 95% |
| Q4R7E5 | Q4R7E5_MACFA | *Macaca fascicularis* (Crab-eating macaque) (Cynomolgus monkey) | 19/07/05 | 06/03/13 | 26 | 1 | 95% |
| I7GL51 | I7GL51_MACFA | *Macaca fascicularis* (Crab-eating macaque) (Cynomolgus monkey) | 03/10/12 | 06/03/13 | 4 | 1 | 95% |
| H2QQU5 | H2QQU5_PANTR | *Pan troglodytes* (Chimpanzee) | 21/03/12 | 26/06/13 | 8 | 1 | 95% |
| D2HHR0 | D2HHR0_AILME | *Ailuropoda melanoleuca* (Giant panda) | 09/02/10 | 03/04/13 | 15 | 1 | 95% |
| D6RIW1 | D6RIW1_HUMAN | *Homo sapiens* (Human) | 13/07/10 | 03/04/13 | 22 | 1 | 95% |
| M3WG47 | M3WG47_FELCA | *Felis catus* (Cat) (*Felis silvestris catus*) | 01/05/13 | 24/07/13 | 3 | 1 | 94% |
| Q3ZC79 | Q3ZC79_BOVIN | *Bos taurus* (Bovine) | 27/09/05 | 29/05/13 | 52 | 1 | 94% |
| L8IKX6 | L8IKX6_BOSMU | *Bos grunniens mutus* | 03/04/13 | 29/05/13 | 2 | 1 | 94% |
| F6RJG0 | F6RJG0_BOVIN | *Bos taurus* (Bovine) | 16/11/11 | 03/04/13 | 11 | 1 | 94% |
| G3QFP6 | G3QFP6_GORGO | *Gorilla gorilla gorilla* (Lowland *gorilla*) | 16/11/11 | 24/07/13 | 11 | 1 | 94% |
| Q01581 | HMCS1_HUMAN | *Homo sapiens* (Human) | 01/07/93 | 24/07/13 | 147 | 2 | 94% |
| G3TJX8 | G3TJX8_LOXAF | *Loxodonta africana* (African elephant) | 16/11/11 | 03/04/13 | 10 | 1 | 94% |
| Q5R7Z9 | HMCS1_PONAB | *Pongo abelii* (Sumatran orangutan) (*Pongo pygmaeus abelii*) | 15/03/05 | 03/04/13 | 62 | 1 | 94% |

TABLE 1-continued pBLAST results filtered on sequences showing >90% sequence identity to
SEQ ID NO: 1 as identified using BLOSUM62 matrix and Threshold = 1.

| Entry name UniprotKb | Accession | Organism | Entry date | Last database update | Entry version | Seq. version | % identity with SEQ ID NO: 1 |
|---|---|---|---|---|---|---|---|
| H0WZW0 | H0WZW0_OTOGA | *Otolemur garnettii* (Small-eared galago) (Garnett's greater bushbaby) | 22/02/12 | 06/03/13 | 6 | 1 | 94% |
| Q5XJ04 | Q5XJ04_HUMAN | *Homo sapiens* (Human) | 23/11/04 | 26/06/13 | 59 | 1 | 94% |
| H0V9C6 | H0V9C6_CAVPO | *Cavia porcellus* (Guinea pig) | 22/02/12 | 26/06/13 | 9 | 1 | 93% |
| G1NZT3 | G1NZT3_MYOLU | *Myotis lucifugus* (Little brown bat) | 19/10/11 | 03/04/13 | 10 | 1 | 93% |
| K9IUA3 | K9IUA3_DESRO | *Desmodus rotundus* (Vampire bat) | 06/02/13 | 03/04/13 | 3 | 1 | 93% |
| L5LIR5 | L5LIR5_MYODS | *Myotis davidii* (David's myotis) | 06/03/13 | 01/05/13 | 3 | 1 | 92% |
| Q8N995 | Q8N995_HUMAN | *Homo sapiens* (Human) | 01/10/02 | 24/07/13 | 67 | 1 | 92% |
| Q6PTA0 | Q6PTA0_BOVIN | *Bos taurus* (Bovine) | 05/07/04 | 29/05/13 | 46 | 1 | 92% |
| F1SMG8 | F1SMG8_PIG | *Sus scrofa* (Pig) | 03/05/11 | 03/04/13 | 16 | 2 | 91% |
| F7C0S7 | F7C0S7_MONDO | *Monodelphis domestica* (Gray short-tailed opossum) | 27/07/11 | 03/04/13 | 13 | 1 | 91% |

TABLE 2 pBLAST results filtered on sequences showing >80% and ≤90% sequence identity
to SEQ ID NO: 1 as identified using BLOSUM62 matrix and Threshold = 1.

| Entry name UniprotKb | Accession | Organism | Entry date | Last database update | Entry version | Seq. version | % identity with SEQ ID NO: 1 |
|---|---|---|---|---|---|---|---|
| L5KKJ1 | L5KKJ1_PTEAL | *Pteropus alecto* (Black flying fox) | 06/03/2013 | 01/05/2013 | 3 | 1 | 90% |
| G3WBA3 | G3WBA3_SARHA | *Sarcophilus harrisii* (Tasmanian devil) (*Sarcophilus laniarius*) | 16/11/2011 | 06/03/2013 | 9 | 1 | 90% |
| A6N2U5 | A6N2U5_MONDO | *Monodelphis domestica* (Gray short-tailed opossum) | 24/07/2007 | 03/04/2013 | 24 | 1 | 89% |
| F7G1A5 | F7G1A5_ORNAN | *Ornithorhynchus anatinus* Duckbill platypus) | 27/07/2011 | 01/05/2013 | 13 | 2 | 88% |
| K7GJZ6 | K7GJZ6_PELSI | *Pelodiscus sinensis* (Chinese softshell turtle) (*Trionyx sinensis*) | 09/01/2013 | 26/06/2013 | 4 | 1 | 88% |
| G9K4I4 | G9K4I4_MUSPF | *Mustela putorius furo* (European domestic ferret) (*Mustela furo*) | 22/02/2012 | 01/05/2013 | 5 | 1 | 88% |
| K9KEK2 | K9KEK2_HORSE | *Equus caballus* (Horse) | 06/03/2013 | 01/05/2013 | 2 | 1 | 87% |
| L8Y8J1 | L8Y8J1_TUPCH | *Tupaia chinensis* (Chinese tree shrew) | 03/04/2013 | 29/05/2013 | 3 | 1 | 86% |
| K7GJZ5 | K7GJZ5_PELSI | *Pelodiscus sinensis* (Chinese softshell turtle) (*Trionyx sinensis*) | 09/01/2013 | 26/06/2013 | 4 | 1 | 85% |
| M7BX40 | M7BX40_CHEMY | *Chelonia mydas* (Green sea-turtle) (*Chelonia agassizi*) | 29/05/2013 | 24/07/2013 | 3 | 1 | 85% |
| R7VQQ3 | R7VQQ3_COLLI | *Columba livia* (Domestic pigeon) | 24/07/2013 | 24/07/2013 | 1 | 1 | 84% |
| F1N9T0 | F1N9T0_CHICK | *Gallus gallus* (Chicken) | 03/05/2011 | 26/06/2013 | 14 | 1 | 84% |
| H0YVN4 | H0YVN4_TAEGU | *Taeniopygia guttata* (Zebra finch) (*Poephila guttata*) | 22/02/2012 | 26/06/2013 | 10 | 1 | 84% |
| P23228 | HMCS1_CHICK | *Gallus gallus* (Chicken) | 01/11/1991 | 26/06/2013 | 95 | 1 | 84% |
| G1KKI9 | G1KKI9_ANOCA | *Anolis carolinensis* (Green anole) (American chameleon) | 19/10/2011 | 26/06/2013 | 11 | 2 | 84% |
| R0JGG2 | R0JGG2_ANAPL | *Anas platyrhynchos* (Domestic duck) (*Anas boschas*) | 26/06/2013 | 26/06/2013 | 1 | 1 | 84% |
| H3ADS1 | H3ADS1_LATCH | *Latimeria chalumnae* (West Indian ocean coelacanth) | 18/04/2012 | 26/06/2013 | 8 | 2 | 84% |
| E9QFB1 | E9QFB1_DANRE | *Danio rerio* (Zebrafish) (*Brachydanio rerio*) | 05/04/2011 | 06/03/2013 | 14 | 1 | 84% |
| E9QHP9 | E9QHP9_DANRE | *Danio rerio* (Zebrafish) (*Brachydanio rerio*) | 05/04/2011 | 06/03/2013 | 14 | 1 | 83% |
| G3UU66 | G3UU66_MELGA | *Meleagris gallopavo* (Common turkey) | 16/11/2011 | 26/06/2013 | 10 | 1 | 81% |

TABLE 3 pBLAST results filtered on sequences showing ≥60% and ≤80% sequence identity to SEQ ID NO: 1 as identified using BLOSUM62 matrix and Threshold = 1.

| Entry name UniprotKb | Accession | Organism | Entry date | Last database update | Entry version | Seq. version | % identity with SEQ ID NO: 1 |
|---|---|---|---|---|---|---|---|
| Q7ZYN7 | Q7ZYN7_XENLA | *Xenopus laevis* (African clawed frog) | 01/06/2003 | 06/03/2013 | 41 | 1 | 79% |
| Q6AX99 | Q6AX99_XENLA | *Xenopus laevis* (African clawed frog) | 13/09/2004 | 26/06/2013 | 43 | 1 | 79% |
| B0JZH5 | B0JZH5_XENTR | *Xenopus tropicalis* (Western clawed frog) (*Silurana tropicalis*) | 18/03/2008 | 24/07/2013 | 39 | 1 | 79% |
| L5KFZ1 | L5KFZ1_PTEAL | *Pteropus alecto* (Black flying fox) | 06/03/2013 | 01/05/2013 | 3 | 1 | 79% |
| F1R6H4 | F1R6H4_DANRE | *Danio rerio* (Zebrafish) (*Brachydanio rerio*) | 03/05/2011 | 03/04/2013 | 15 | 1 | 78% |
| Q7ZWE2 | Q7ZWE2_DANRE | *Danio rerio* (Zebrafish) (*Brachydanio rerio*) | 01/06/2003 | 03/04/2013 | 62 | 1 | 78% |
| F1QKU4 | F1QKU4_DANRE | *Danio rerio* (Zebrafish) (*Brachydanio rerio*) | 03/05/2011 | 06/03/2013 | 15 | 1 | 78% |
| G3UQK0 | G3UQK0_MELGA | *Meleagris gallopavo* (Common turkey) | 16/11/2011 | 26/06/2013 | 10 | 1 | 78% |
| I3K0G3 | I3K0G3_ORENI | *Oreochromis niloticus* (Nile tilapia) (*Tilapia nilotica*) | 11/07/2012 | 29/05/2013 | 7 | 1 | 77% |
| H3ADS0 | H3ADS0_LATCH | *Latimeria chalumnae* (West Indian ocean coelacanth) | 18/04/2012 | 26/06/2013 | 8 | 1 | 77% |
| H2MC81 | H2MC81_ORYLA | *Oryzias latipes* (Medaka fish) (Japanese ricefish) | 21/03/2012 | 26/06/2013 | 7 | 1 | 75% |
| G3Q3W0 | G3Q3W0_GASAC | *Gasterosteus aculeatus* (Three-spined stickleback) | 16/11/2011 | 03/04/2013 | 10 | 1 | 74% |
| M3ZV74 | M3ZV74_XIPMA | *Xiphophorus maculatus* (Southern platyfish) (*Platypoecilus maculatus*) | 01/05/2013 | 29/05/2013 | 2 | 1 | 74% |
| H2TS59 | H2TS59_TAKRU | *Takifugu rubripes* (Japanese pufferfish) (*Fugu rubripes*) | 21/03/2012 | 26/06/2013 | 6 | 1 | 74% |
| H2TS58 | H2TS58_TAKRU | *Takifugu rubripes* (Japanese pufferfish) (*Fugu rubripes*) | 21/03/2012 | 26/06/2013 | 7 | 1 | 73% |
| M7BR31 | M7BR31_CHEMY | *Chelonia mydas* (Green sea-turtle) (*Chelonia agassizi*) | 29/05/2013 | 24/07/2013 | 3 | 1 | 72% |
| G2YB33 | G2YB33_BOTF4 | *Botryotinia fuckeliana* (strain T4) (Noble rot fungus) (*Botrytis cinerea*) | 16/11/2011 | 24/07/2013 | 7 | 1 | 72% |
| K4FU21 | K4FU21_CALMI | *Callorhynchus milli* (Elephant fish) (Australian ghost shark) | 09/01/2013 | 03/04/2013 | 3 | 1 | 71% |
| Q4T144 | Q4T144_TETNG | *Tetraodon nigroviridis* (Spotted green pufferfish) (*Chelonodon nigroviridis*) | 19/07/2005 | 03/04/2013 | 37 | 1 | 71% |
| H9GFS9 | H9GFS9_ANOCA | *Anolis carolinensis* (Green anole) (American chameleon) | 16/05/2012 | 26/06/2013 | 6 | 2 | 71% |
| J9K9G7 | J9K9G7_ACYPI | *Acyrthosiphon pisum* (Pea aphid) | 31/10/2012 | 29/05/2013 | 5 | 1 | 71% |
| E1C9C4 | E1C9C4_CHICK | *Gallus gallus* (Chicken) | 02/11/2010 | 24/07/2013 | 17 | 2 | 70% |
| G3WS60 | G3WS60_SARHA | *Sarcophilus harrisii* (Tasmanian devil) (*Sarcophilus laniarius*) | 16/11/2011 | 06/03/2013 | 8 | 1 | 70% |
| D2DGZ4 | D2DGZ4_9CUCU | *Ips confusus* | 09/02/2010 | 06/03/2013 | 8 | 1 | 70% |
| D5GFX4 | D5GFX4_TUBMM | *Tuber melanosporum* (strain Mel28) (Perigord black truffle) | 15/06/2010 | 06/03/2013 | 13 | 1 | 70% |
| L5KJA2 | L5KJA2_PTEAL | *Pteropus alecto* (Black flying fox) | 06/03/2013 | 01/05/2013 | 3 | 1 | 70% |
| Q9M6A5 | Q9M6A5_SEDJA | *Sedirea japonica* (Orchid) (*Aerides japonica*) | 01/10/2000 | 06/03/2013 | 33 | 1 | 70% |
| Q5DU91 | Q5DU91_BOVIN | *Bos taurus* (Bovine) | 29/03/2005 | 03/04/2013 | 31 | 1 | 70% |
| H3CHP0 | H3CHP0_TETNG | *Tetraodon nigroviridis* (Spotted green pufferfish) (*Chelonodon nigroviridis*) | 18/04/2012 | 06/03/2013 | 5 | 1 | 69% |
| G3WS59 | G3WS59_SARHA | *Sarcophilus harrisii* (Tasmanian devil) (*Sarcophilus laniarius*) | 16/11/2011 | 03/04/2013 | 14 | 1 | 69% |
| H1A3Q9 | H1A3Q9_TAEGU | *Taeniopygia guttata* (Zebra finch) (*Poephila guttata*) | 22/02/2012 | 26/06/2013 | 10 | 1 | 69% |
| G1MZD6 | G1MZD6_MELGA | *Meleagris gallopavo* (Common turkey) | 19/10/2011 | 26/06/2013 | 11 | 1 | 69% |
| D7T1S7 | D7T1S7_VITVI | *Vitis vinifera* (Grape) | 10/08/2010 | 03/04/2013 | 12 | 1 | 69% |
| D7TMZ6 | D7TMZ6_VITVI | *Vitis vinifera* (Grape) | 10/08/2010 | 03/04/2013 | 13 | 1 | 69% |
| A4GKH7 | A4GKH7_CYAPA | *Cyanophora paradoxa* | 17/04/2007 | 03/04/2013 | 20 | 1 | 68% |
| G3R459 | G3R459_GORGO | *Gorilla gorilla gorilla* (Lowland gorilla) | 16/11/2011 | 24/07/2013 | 14 | 1 | 67% |
| G1R086 | G1R086_NOMLE | *Nomascus leucogenys* (Northern white-cheeked gibbon) (*Hylobates leucogenys*) | 19/10/2011 | 03/04/2013 | 10 | 1 | 67% |

TABLE 3-continued pBLAST results filtered on sequences showing ≥60% and ≤80% sequence identity
to SEQ ID NO: 1 as identified using BLOSUM62 matrix and Threshold = 1.

| Entry name UniprotKb | Accession | Organism | Entry date | Last database update | Entry version | Seq. version | % identity with SEQ ID NO: 1 |
|---|---|---|---|---|---|---|---|
| P54868 | HMCS2_HUMAN | Homo sapiens (Human) | 01/10/1996 | 24/07/2013 | 130 | 1 | 67% |
| H2PZT1 | H2PZT1_PANTR | Pan troglodytes (Chimpanzee) | 21/03/2012 | 26/06/2013 | 8 | 1 | 67% |
| H2N659 | H2N659_PONAB | Pongo abelii (Sumatran orangutan) (Pongo pygmaeus abelii) | 21/03/2012 | 06/03/2013 | 8 | 1 | 67% |
| G7NX69 | G7NX69_MACFA | Macaca fascicularis (Crab-eating macaque) (Cynomolgus monkey) | 25/01/2012 | 06/03/2013 | 5 | 1 | 67% |
| F7DRJ3 | F7DRJ3_MACMU | Macaca mulatta (Rhesus macaque) | 27/07/2011 | 06/03/2013 | 13 | 1 | 67% |
| I2CVM8 | I2CVM8_MACMU | Macaca mulatta (Rhesus macaque) | 11/07/2012 | 06/03/2013 | 4 | 1 | 67% |
| H3HZF8 | H3HZF8_STRPU | Strongylocentrotus purpuratus (Purple sea urchin) | 18/04/2012 | 03/04/2013 | 10 | 1 | 67% |
| K7V445 | K7V445_MAIZE | Zea mays (Maize) | 06/02/2013 | 24/07/2013 | 5 | 1 | 67% |
| H0WH94 | H0WH94_OTOGA | Otolemur garnettii (Small-eared galago) (Garnett's greater bushbaby) | 22/02/2012 | 03/04/2013 | 9 | 1 | 66% |
| G3HP76 | G3HP76_CRIGR | Cricetulus griseus (Chinese hamster) (Cricetulus barabensis griseus) | 16/11/2011 | 01/05/2013 | 9 | 1 | 66% |
| Q8N7N8 | Q8N7N8_MOUSE | Mus musculus (Mouse) | 01/10/2002 | 24/07/2013 | 53 | 1 | 66% |
| Q68G44 | Q68G44_RAT | Rattus norvegicus (Rat) | 11/10/2004 | 24/07/2013 | 61 | 1 | 66% |
| P54869 | HMCS2_MOUSE | Mus musculus (Mouse) | 01/10/1996 | 24/07/2013 | 112 | 2 | 66% |
| G5BV18 | G5BV18_HETGA | Heterocephalus glaber (Naked mole rat) | 14/12/2011 | 06/03/2013 | 7 | 1 | 66% |
| G1SPL7 | G1SPL7_RABIT | Oryctolagus cuniculus (Rabbit) | 19/10/2011 | 03/04/2013 | 10 | 1 | 66% |
| L5LWQ0 | L5LWQ0_MYODS | Myotis davidii (David's myotis) | 06/03/2013 | 01/05/2013 | 3 | 1 | 66% |
| L8INN7 | L8INN7_BOSMU | Bos grunniens mutus | 03/04/2013 | 29/05/2013 | 2 | 1 | 66% |
| F7CBP9 | F7CBP9_HORSE | Equus caballus (Horse) | 27/07/2011 | 06/03/2013 | 12 | 1 | 66% |
| Q2KIE6 | HMCS2_BOVIN | Bos taurus (Bovine) | 30/05/2006 | 24/07/2013 | 56 | 1 | 66% |
| L8Y9N6 | L8Y9N6_TUPCH | Tupaia chinensis (Chinese tree shrew) | 03/04/2013 | 29/05/2013 | 3 | 1 | 66% |
| D4P8J3 | D4P8J3_CAPHI | Capra hircus (Goat) | 18/05/2010 | 06/03/2013 | 6 | 1 | 66% |
| O02734 | HMCS2_PIG | Sus scrofa (Pig) | 15/12/1998 | 24/07/2013 | 92 | 1 | 66% |
| K2RZ92 | K2RZ92_MACPH | Macrophomina phaseolina (strain MS6) (Charcoal rot fungus) | 28/11/2012 | 06/03/2013 | 3 | 1 | 66% |
| B7FFG2 | B7FFG2_MEDTR | Medicago truncatula (Barrel medic) (Medicago tribuloides) | 10/02/2009 | 06/03/2013 | 12 | 1 | 66% |
| H6TNP8 | H6TNP8_ELAGV | Elaeis guineensis var. tenera (Oil palm) | 18/04/2012 | 03/04/2013 | 5 | 1 | 66% |
| F6GTT8 | F6GTT8_VITVI | Vitis vinifera (Grape) | 27/07/2011 | 03/04/2013 | 9 | 1 | 66% |
| F1QML1 | F1QML1_DANRE | Danio rerio (Zebrafish) (Brachydanio rerio) | 03/05/2011 | 03/04/2013 | 15 | 1 | 66% |
| P22791 | HMCS2_RAT | Rattus norvegicus (Rat) | 01/08/1991 | 24/07/2013 | 111 | 1 | 65% |
| H0V7K3 | H0V7K3_CAVPO | Cavia porcellus (Guinea pig) | 22/02/2012 | 26/06/2013 | 9 | 1 | 65% |
| M3WF61 | M3WF61_FELCA | Felis catus (Cat) (Felis silvestris catus) | 01/05/2013 | 24/07/2013 | 3 | 1 | 65% |
| I3LZF8 | I3LZF8_SPETR | Spermophilus tridecemlineatus (Thirteen-lined ground squirrel) (Ictidomys tridecemlineatus) | 11/07/2012 | 26/06/2013 | 6 | 1 | 65% |
| G9K4I5 | G9K4I5_MUSPF | Mustela putorius furo (European domestic ferret) (Mustela furo) | 22/02/2012 | 01/05/2013 | 8 | 1 | 65% |
| M3XQT6 | M3XQT6_MUSPF | Mustela putorius furo (European domestic ferret) (Mustela furo) | 01/05/2013 | 29/05/2013 | 2 | 1 | 65% |
| E2RAD0 | E2RAD0_CANFA | Canis familiaris (Dog) (Canis lupus familiaris) | 30/11/2010 | 29/05/2013 | 22 | 1 | 65% |
| F7DRS4 | F7DRS4_ORNAN | Ornithorhynchus anatinus (Duckbill platypus) | 27/07/2011 | 03/04/2013 | 10 | 1 | 65% |
| L7MF12 | L7MF12_9ACAR | Rhipicephalus pulchellus | 06/03/2013 | 01/05/2013 | 2 | 1 | 65% |
| K1PE75 | K1PE75_CRAGI | Crassostrea gigas (Pacific oyster) (Crassostrea angulata) | 28/11/2012 | 03/04/2013 | 4 | 1 | 65% |
| R4RTW8 | R4RTW8_NEOVI | Neovison vison (American mink) (Mustela vison) | 24/07/2013 | 24/07/2013 | 1 | 1 | 65% |
| F7E131 | F7E131_MACMU | Macaca mulatta (Rhesus macaque) | 27/07/2011 | 06/03/2013 | 9 | 1 | 65% |
| K7E2K1 | K7E2K1_MONDO | Monodelphis domestica (Gray short-tailed opossum) | 09/01/2013 | 03/04/2013 | 3 | 1 | 65% |
| D2HZW4 | D2HZW4_AILME | Ailuropoda melanoleuca (Giant panda) | 09/02/2010 | 06/03/2013 | 15 | 1 | 64% |
| G1MH25 | G1MH25_AILME | Ailuropoda melanoleuca (Giant panda) | 19/10/2011 | 06/03/2013 | 11 | 1 | 64% |

TABLE 3-continued pBLAST results filtered on sequences showing ≥60% and ≤80% sequence identity
to SEQ ID NO: 1 as identified using BLOSUM62 matrix and Threshold = 1.

| Entry name UniprotKb | Accession | Organism | Entry date | Last database update | Entry version | Seq. version | % identity with SEQ ID NO: 1 |
|---|---|---|---|---|---|---|---|
| F6ZK24 | F6ZK24_CALJA | *Callithrix jacchus* (White-tufted-ear marmoset) | 27/07/2011 | 03/04/2013 | 9 | 1 | 64% |
| P54961 | HMCS1_BLAGE | *Blattella germanica* (German cockroach) (*Blatta germanica*) | 01/10/1996 | 03/04/2013 | 70 | 1 | 64% |
| B3MFN4 | B3MFN4_DROAN | *Drosophila ananassae* (Fruit fly) | 02/09/2008 | 26/06/2013 | 30 | 1 | 64% |
| K7J490 | K7J490_NASVI | *Nasonia vitripennis* (Parasitic wasp) | 09/01/2013 | 01/05/2013 | 5 | 1 | 64% |
| B4KRT0 | B4KRT0_DROMO | *Drosophila mojavensis* (Fruit fly) | 23/09/2008 | 26/06/2013 | 27 | 1 | 64% |
| B4HSW8 | B4HSW8_DROSE | *Drosophiia sechellia* (Fruit fly) | 23/09/230008 | 26/06/2013 | 27 | 1 | 64% |
| B3NPJ8 | B3NPJ8_DROER | *Drosophiia erecta* (Fruit fly) | 02/09/2008 | 26/06/2013 | 28 | 1 | 64% |
| B4P683 | B4P683_DROYA | *Drosophila yakuba* (Fruit fly) | 23/09/2008 | 26/06/2013 | 27 | 1 | 64% |
| Q7K4Q9 | Q7K4Q9_DROME | *Drosophila melanogaster* (Fruit fly) | 03/10/2006 | 24/07/2013 | 71 | 1 | 64% |
| B4GAB9 | B4GAB9_DROPE | *Drosophila persimilis* (Fruit fly) | 23/09/2008 | 26/06/2013 | 29 | 1 | 64% |
| Q291S8 | Q291S8_DROPS | *Drosophila pseudoobscura pseudoobscura* (Fruit fly) | 04/04/2006 | 29/05/2013 | 45 | 1 | 64% |
| Q3YMU3 | Q3YMU3_DROSI | *Drosophila simulans* (Fruit fly) | 27/09/2005 | 29/05/2013 | 29 | 1 | 64% |
| Q7Q6H2 | Q7Q6H2_ANOGA | *Anopheles gambiae* (African malaria mosquito) | 15/12/2003 | 29/05/2013 | 62 | 3 | 64% |
| J9NSN6 | J9NSN6_CANFA | *Canis familiaris* (Dog) (*Canis lupus familiaris*) | 31/10/2012 | 06/03/2013 | 4 | 1 | 64% |
| B7PDN8 | B7PDN8_IXOSC | *Ixodes scapularis* (Black-legged tick) (Deer tick) | 10/02/2009 | 29/05/2013 | 29 | 1 | 64% |
| B4MFP6 | B4MFP6_DROVI | *Drosophila virilis* (Fruit fly) | 23/09/2008 | 26/06/2013 | 32 | 1 | 63% |
| B4J8F1 | B4J8F1_DROGR | *Drosophila grimshawi* (Fruit fly) (*Idiomyia grimshawi*) | 23/09/2008 | 26/06/2013 | 31 | 1 | 63% |
| C3ZJ14 | C3ZJ14_BRAFL | *Branchiostoma floridae* (Florida lancelet) (Amphioxus) | 28/07/2009 | 03/04/2013 | 23 | 1 | 63% |
| Q17AU0 | Q17AU0_AEDAE | *Aedes aegypti* (Yellowfever mosquito) (*Culex aegypti*) | 25/07/2006 | 29/05/2013 | 47 | 1 | 63% |
| B0W3P9 | B0W3P9_CULQU | *Culex quinquefasciatus* (Southern house mosquito) (*Culex pungens*) | 08/04/2008 | 29/05/2013 | 30 | 1 | 63% |
| B5ANQ1 | B5ANQ1_MESAU | *Mesocricetus auratus* (Golden hamster) | 23/09/2008 | 06/03/2013 | 7 | 1 | 63% |
| C6TE02 | C6TE02_SOYBN | *Glycine max* (Soybean) (*Glycine hispida*) | 22/09/2009 | 03/04/2013 | 11 | 1 | 63% |
| Q5BWB2 | Q5BWB2_SCHJA | *Schistosoma japonicum* (Blood fluke) | 12/04/2005 | 03/04/2013 | 30 | 2 | 63% |
| J7MBN5 | J7MBN5_9NEOP | *Nasutitermes takasagoensis* | 31/10/2012 | 06/03/2013 | 4 | 2 | 62% |
| D6WTE1 | D6WTE1_TRICA | *Tribolium castaneum* (Red flour beetle) | 10/08/2010 | 01/05/2013 | 19 | 1 | 62% |
| F4X3B5 | F4X3B5_ACREC | *Acromyrmex echinatior* (Panamanian leafcutter ant) (*Acromyrmex octospinosus echinatior*) | 28/06/2011 | 03/04/2013 | 9 | 1 | 62% |
| D3TNU7 | D3TNU7_GLOMM | *Glossina morsitans morsitans* (Savannah tsetse fly) | 20/04/2010 | 03/04/2013 | 9 | 1 | 62% |
| B4MPF2 | B4MPF2_DROWI | *Drosophila willistoni* (Fruit fly) | 23/09/2008 | 26/06/2013 | 31 | 1 | 62% |
| H9K5V0 | H9K5V0_APIME | *Apis mellifera* (Honeybee) | 16/05/2012 | 03/04/2013 | 8 | 1 | 62% |
| B8Y0J3 | B8Y0J3_LINUS | *Linum usitatissimum* (Flax) (*Linum humile*) | 03/03/2009 | 06/03/2013 | 11 | 1 | 62% |
| H9I3F6 | H9I3F6_ATTCE | *Atta cephalotes* (Leafcutter ant) | 16/05/2012 | 06/03/2013 | 6 | 1 | 61% |
| I1VX00 | I1VX00_BOMTE | *Bombus terrestris* (Buff-tailed bumblebee) (*Apis terrestris*) | 11/07/2012 | 03/04/2013 | 5 | 1 | 61% |
| E9JB54 | E9JB54_SOLIN | *Solenopsis invicta* (Red imported fire ant) (*Solenopsis wagneri*) | 05/04/2011 | 03/04/2013 | 9 | 1 | 61% |
| E2C8M0 | E2C8M0_HARSA | *Harpegnathos saltator* (Jerdon's jumping ant) | 30/11/2010 | 03/04/2013 | 11 | 1 | 61% |
| A5A798 | A5A798_BOMMO | *Bombyx mori* (Silk moth) | 12/06/2007 | 24/07/2013 | 35 | 1 | 61% |
| B7Z784 | B7Z784_HUMAN | *Homo sapiens* (Human) | 03/03/2009 | 03/04/2013 | 16 | 1 | 61% |
| B7Z7M8 | B7Z7M8_HUMAN | *Homo sapiens* (Human) | 03/03/2009 | 29/05/2013 | 18 | 1 | 61% |
| H2RIA5 | H2RIA5_PANTR | *Pan troglodytes* (Chimpanzee) | 21/03/2012 | 26/06/2013 | 8 | 1 | 60% |
| F6ZJI7 | F6ZJI7_CALJA | *Callithrix jacchus* (White-tufted-ear marmoset) | 27/07/2011 | 03/04/2013 | 12 | 1 | 60% |
| E2AV93 | E2AV93_CAMFO | *Camponotus floridanus* (Florida carpenter ant) | 30/11/2010 | 03/04/2013 | 11 | 1 | 60% |

As mentioned above and as outlined in more detail below, the present invention relates to improved variants of enzymes which are capable of converting acetone and a compound which provides an activated acetyl group into HIV wherein, as a model enzyme, the HMG CoA synthase of *Mus musculus* shown in SEQ IDS NO:1 has been used. As outlined in more detail further below, it has been shown that it is possible to provide variants of this enzyme which show increased activity with respect to the enzymatic conversion to produce HIV from acetone and a compound which provides an activated acetyl group. An improved enzyme variant or an enzyme variant capable of catalyzing a reaction with increased activity is defined as an enzyme variant which differs from the wildtype enzyme and which catalyzes the respective production of HIV so that the specific activity of the enzyme variant is higher than that of the specific variant of the wildtype enzyme.

HIV production activity of SEQ ID NO:1 as described by kinetic parameters Kcat, Km and the Kcat/Km ratio are provided in Table 4. Enzyme parameters can be measured by techniques and methods known in the art and a precise protocol is given in Example 5.

TABLE 4

Kinetic data for HIV production from acetone by wild type enzyme of *Mus musculus*

| Enzyme | Kcat ($s^{-1}$) | Km (mM) | Kcat/Km ($10^{-3}$ $s^{-1}$/mM) |
|---|---|---|---|
| Wild type enzyme | $0.93 \times 10^{-2}$ | 158 | 0.0059 |

Mutagenesis studies on wildtype HMG-CoA synthases (Chun et al. (Biochem. 39 (2000), 14670-14681); Sutherlin et al. (J. Bacterio. 184 (2002), 4065-4070); Wang et al. (J. Biol. Chem. 279 (2004), 40283-40288) and Nagegowda et al. (Biochem J. 383 (2004, 517-527) have been performed. These studies, inter alia, identified key catalytic amino acids at highly conserved positions which are presented in Table 5. In particular, C129 serves as the acetyl group receiver/donor and the intermediate reaction configuration involves the acetylated form of the enzyme at position 129.

TABLE 5

Key conserved amino acids. Numbering along sequence is done using SEQ ID NO: 1 as reference starting from Met 1.

| Position along sequence | Conserved amino acid |
|---|---|
| 95 | E |
| 129 | C |
| 159 | D |
| 203 | D |

As mentioned above, it has been shown that HMG CoA syntheses can act to produce HIV enzymatically from acetone and a compound which provides an activated acetyl group. The present invention provides improved variants of such "HIV synthase" enzymes defined above which are capable of converting acetone and a compound which provides an activated acetyl group into HIV. The inventors used as a model enzyme the HMG CoA synthase of *Mus musculus* shown in SEQ IDS NO:1 and could show that it is possible to provide variants of this enzyme which show increased activity with respect to the enzymatic conversion to produce HIV from acetone and a compound which provides an activated acetyl group.

In one preferred embodiment the variants of the present invention are characterized by the feature that they are derived from an HIV synthase defined above, more preferably a HMG CoA synthase having the amino acid sequence shown in SEQ ID NO:1 or a highly related sequence (at least 60% identical) and in which mutations are effected at one or more of the indicated positions and by the feature that they show the ability to convert acetone and a compound which provides an activated acetyl group as defined above into HIV and that they can do this with an improved activity. In a preferred embodiment the variant according to the present invention is derived from a sequence which shows at least 80% sequence identity to SEQ ID NO:1 and in which one or more substitutions and/or deletions and/or insertions at the positions indicated herein below have been effected.

However, the teaching of the present invention is not restricted to variants of the HMG CoA synthase enzyme of *Mus musculus* shown in SEQ ID NO: 1 which had been used as a model enzyme but can be extended to HMG CoA synthases from other organisms, in particular to enzymes which are structurally related to SEQ ID NO:1 such as, e.g., truncated variants of the enzyme. Thus, the present invention also relates to variants of HIV syntheses, in particular to other HMG CoA syntheses, which are structurally related to the *Mus musculus* sequence (SEQ ID NO: 1) and which show one or more substitutions and/or deletions and/or insertions at positions corresponding to any of the positions as indicated herein-below. The term "structurally related" refers to HIV syntheses, in particular to HMG CoA synthases, which show a sequence identity of at least n % to the sequence shown in SEQ ID NO: 1 with n being an integer between 60 and 100, preferably 60, 65, 70, 75, 80, 85, 90, 91, 92, 93, 94, 95, 96, 97, 98 or 99.

Thus, in one embodiment the variant of an HIV synthase, in particular of a HMG CoA synthase, according to the present invention has or preferably is derived from a sequence which is at least n % identical to SEQ ID NO:1 with n being an integer between 60 and 100, preferably 60, 65, 70, 75, 80, 85, 90, 91, 92, 93, 94, 95, 96, 97, 98 or 99, and it has (a) substitution(s) and/or (a) deletion and/or (an) insertion(s) at a position as indicated below. When the sequences which are compared do not have the same length, the degree of identity either refers to the percentage of amino acid residues in the shorter sequence which are identical to amino acid residues in the longer sequence or to the percentage of amino acid residues in the longer sequence which are identical to amino acid residues in the shorter sequence. Preferably, it refers to the percentage of amino acid residues in the shorter sequence which are identical to amino acid residues in the longer sequence. The degree of sequence identity can be determined according to methods well known in the art using preferably suitable computer algorithms such as CLUSTAL.

When using the Clustal analysis method to determine whether a particular sequence is, for instance, at least 60% identical to a reference sequence default settings may be used or the settings are preferably as follows: Matrix: blosum 30; Open gap penalty: 10.0; Extend gap penalty: 0.05; Delay divergent: 40; Gap separation distance: 8 for comparisons of amino acid sequences. For nucleotide sequence comparisons, the Extend gap penalty is preferably set to 5.0.

In a preferred embodiment ClustalW2 is used for the comparison of amino acid sequences. In the case of pairwise comparisons/alignments, the following settings are preferably chosen: Protein weight matrix: BLOSUM 62; gap open: 10; gap extension: 0.1. In the case of multiple comparisons/ alignments, the following settings are preferably chosen: Protein weight matrix: BLOSUM 62; gap open: 10; gap extension: 0.2; gap distance: 5; no end gap.

Preferably, the degree of identity is calculated over the complete length of the sequence.

Amino acid residues located at a position corresponding to a position as indicated herein-below in the amino acid sequence shown in SEQ ID NO:1 can be identified by the skilled person by methods known in the art. For example, such amino acid residues can be identified by aligning the sequence in question with the sequence shown in SEQ ID NO:1 and by identifying the positions which correspond to the above indicated positions of SEQ ID NO:1. The alignment can be done with means and methods known to the skilled person, e.g. by using a known computer algorithm such as the Lipman-Pearson method (Science 227 (1985), 1435) or the CLUSTAL algorithm. It is preferred that in such an alignment maximum homology is assigned to conserved amino acid residues present in the amino acid sequences.

In a preferred embodiment ClustalW2 is used for the comparison of amino acid sequences. In the case of pairwise comparisons/alignments, the following settings are preferably chosen: Protein weight matrix: BLOSUM 62; gap open: 10; gap extension: 0.1. In the case of multiple comparisons/alignments, the following settings are preferably chosen: Protein weight matrix: BLOSUM 62; gap open: 10; gap extension: 0.2; gap distance: 5; no end gap.

When the amino acid sequences of HIV synthases are aligned by means of such a method, regardless of Insertions or deletions that occur in the amino acid sequences, the positions of the corresponding amino acid residues can be determined in each of the HIV synthases.

In the context of the present invention, "substituted with another amino acid residue" means that the respective amino acid residues at the indicated position can be substituted with any other possible amino acid residues, e.g. naturally occurring amino acids or non-naturally occurring amino acids (Brustad and Arnold, Curr. Opin. Chem. Biol. 15 (2011), 201-210), preferably with an amino acid residues selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. Preferred substitutions for certain positions are indicated further below. Moreover, the term "substituted" or "substitution" also means that the respective amino acid residue at the indicated position is modified.

Such modifications include naturally occurring modifications and non-naturally occurring modifications. Naturally occurring modifications include but are not limited to eukaryotic post-translational modification, such as attachment of functional groups (e.g. acetate, phosphate, hydroxyl, lipids (myristoylation of glycine residues) and carbohydrates (e.g. glycosylation of arginine, asparagines etc.). Naturally occurring modifications also encompass the change in the chemical structure by citrullination, carbamoylation and disulphide bond formation between cysteine residues; attachment of co-factors (FMN or FAD that can be covalently attached) or the attachment of peptides (e.g. ubiquitination or sumoylation).

Non-naturally occurring modifications include, e.g., in vitro modifications such as biotinylation of lysine residue or the inclusion of non-canonical amino acids (see Liu and Schultz, Annu. Rev. Biochem. 79 (2010), 413-44 and Wang et al., Chem. Bio. 2009 Mar. 27; 16 (3), 323-336; doi: 101016/jchembiol.2009.03.001).

In the context of the present invention, "deleted" or "deletion" means that the amino acid at the corresponding position is deleted.

In the context of the present invention, "inserted" or "insertion" means that at the respective position one or two, preferably one amino acid residue is inserted, preferably in front of the indicated position.

In accordance with the foregoing, the present invention relates to a variant of an HIV synthase, wherein the HIV variant is characterized in that it shows one or more substitutions, deletions and/or insertions in comparison to the corresponding sequence from which it is derived and wherein these substitutions, deletions and/or insertions occur at one or more of the positions corresponding to positions 7, 13, 22, 24, 33, 38, 41, 43, 54, 74, 75, 81, 165, 167, 171, 201, 221, 222, 226, 246, 259, 296, 325, 338, 345, 363, 394, 396, 457, 462, 473, 475, 480, 481, 486, 490, 491, 500, 514, 516, 519 and 520 in the amino acid sequence shown in SEQ ID NO:1.

In a preferred embodiment, the variant according to the invention is characterized in that it contains at least two deletions, substitutions and/or insertions wherein the deletion/insertion/substitution is at position 100 in the amino acid sequence shown in SEQ ID NO:1 or at a position corresponding to this position and another deletion/insertion/substitution is at position 201 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 7, 13, 22, 24, 33, 38, 74, 75, 480, 41, 54, 43, 81, 165, 167, 171, 201, 221, 222, 226, 246, 259, 270, 296, 325, 338, 345, 363, 394, 396, 457, 462, 473, 475, 481, 486, 490, 491, 500, 514, 516, 519 and 520 in the amino acid sequence shown in SEQ ID NO:1.

In a preferred embodiment, the variant according to the invention is characterized in that it contains at least two deletions, substitutions and/or insertions wherein the deletion/insertion/substitution is at position 270 in the amino acid sequence shown in SEQ ID NO:1 or at a position corresponding to this position and another deletion/insertion/substitution is at position 201 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 7, 13, 22, 24, 33, 38, 74, 75, 480, 41, 43, 54, 81, 100, 165, 167, 171, 201, 221, 222, 226, 246, 259, 296, 325, 338, 345, 363, 394, 396, 457, 462, 473, 475, 481, 486, 490, 491, 500, 514, 516, 519 and 520 in the amino acid sequence shown in SEQ ID NO:1.

In a preferred embodiment, the variant according to the invention is characterized in that it contains at least two deletions, substitutions and/or insertions wherein the deletion/insertion/substitution is at position 22 in the amino acid sequence shown in SEQ ID NO:1 or at a position corresponding to this position and another deletion/insertion/substitution is at position 201 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 7, 13, 24, 33, 38, 74, 75, 480, 41, 43, 54, 81, 100, 165, 167, 171, 221, 222, 226, 246, 259, 270, 296, 325, 338, 345, 363, 394, 396, 457, 462, 473, 475, 481, 486, 490, 491, 500, 514, 516, 519 and 520 in the amino acid sequence shown in SEQ ID NO:1.

In a preferred embodiment, the variant according to the invention is characterized in that it contains at least two deletions, substitutions and/or insertions wherein the deletion/insertion/substitution is at position 22 in the amino acid sequence shown in SEQ ID NO:1 or at a position corresponding to this position and another deletion/insertion/substitution is at position 462 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 7, 13, 24, 33, 38, 54, 74, 75, 480, 41, 43, 81, 100, 165, 167, 171, 201, 221, 222, 226, 246, 259, 270, 296, 325, 338, 345, 363, 394, 396, 457, 473, 475, 481, 486, 490, 491, 500, 514, 516, 519 and 520 in the amino acid sequence shown in SEQ ID NO:1.

In a preferred embodiment, the variant according to the invention is characterized in that it contains at least two deletions, substitutions and/or Insertions wherein the deletion/insertion/substitution is at position 22 in the amino acid sequence shown in SEQ ID NO:1 or at a position corresponding to this position and another deletion/insertion/substitution is at position 519 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or Insertions occur at one or more of the positions corresponding to positions 7, 13, 24, 33, 38, 74, 75, 480, 41, 43, 54, 81, 100, 165, 167, 171, 201, 221, 222, 226, 246, 259, 270, 296, 325, 338, 345, 363, 394, 396, 457, 462, 473, 475, 481, 486, 490, 491, 500, 514, 516, and 520 in the amino acid sequence shown in SEQ ID NO:1.

In a preferred embodiment, the variant according to the invention is characterized in that it contains at least two deletions, substitutions and/or insertions wherein the deletion/insertion/substitution is at position 201 in the amino acid sequence shown in SEQ ID NO:1 or at a position corresponding to this position and another deletion/insertion/substitution is at position 519 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 7, 13, 24, 33, 38, 54, 74, 75, 480, 22, 41, 43, 81, 100, 165, 167, 171, 221, 222, 226, 246, 259, 270, 296, 325, 338, 345, 363, 394, 396, 457, 462, 473, 475, 481, 486, 490, 491, 500, 514, 516, and 520 in the amino acid sequence shown in SEQ ID NO:1.

In a preferred embodiment, the variant according to the invention is characterized in that it contains at least two deletions, substitutions and/or insertions wherein the deletion/insertion/substitution is at position 201 in the amino acid sequence shown in SEQ ID NO:1 or at a position corresponding to this position and another deletion/insertion/substitution is at position 462 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 7, 13, 24, 33, 38, 54, 74, 75, 480, 22, 41, 43, 81, 100, 165, 167, 171, 221, 222, 226, 246, 259, 270, 296, 325, 338, 345, 363, 394, 396, 457, 473, 475, 481, 486, 490, 491, 500, 514, 516, 519 and 520 in the amino acid sequence shown in SEQ ID NO:1.

In a preferred embodiment, the variant according to the invention is characterized in that it contains at least two deletions, substitutions and/or insertions wherein the deletion/insertion/substitution is at position 462 in the amino acid sequence shown in SEQ ID NO:1 or at a position corresponding to this position and another deletion/insertion/substitution is at position 519 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 7, 13, 24, 33, 38, 54, 74, 75, 480, 22, 41, 43, 81, 100, 165, 167, 171, 201, 221, 222, 226, 246, 259, 270, 296, 325, 338, 345, 363, 394, 396, 457, 473, 475, 481, 486, 490, 491, 500, 514, 516, and 520 in the amino acid sequence shown in SEQ ID NO:1.

In a preferred embodiment, the variant according to the invention is characterized in that it contains at least three deletions, substitutions and/or insertions wherein the deletion/insertion/substitution is at position 22 in the amino acid sequence shown in SEQ ID NO:1 or at a position corresponding to this position and another deletion/insertion/substitution is at position 201 in the amino acid sequence shown in SEQ ID NO:1 or at a position corresponding to this position and another deletion/insertion/substitution is at position 462 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 7, 13, 24, 33, 38, 54, 74, 75, 480, 41, 43, 81, 100, 165, 167, 171, 221, 222, 226, 246, 259, 270, 296, 325, 338, 345, 363, 394, 396, 457, 473, 475, 481, 486, 490, 491, 500, 514, 516, 519 and 520 in the amino acid sequence shown in SEQ ID NO:1.

In a preferred embodiment, the variant according to the invention is characterized in that it contains at least three deletions, substitutions and/or Insertions wherein the deletion/insertion/substitution is at position 22 in the amino acid sequence shown in SEQ ID NO:1 or at a position corresponding to this position and another deletion/insertion/substitution is at position 201 in the amino acid sequence shown in SEQ ID NO:1 or at a position corresponding to this position and another deletion/insertion/substitution is at position 519 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 7, 13, 24, 33, 38, 54, 74, 75, 480, 41, 43, 81, 100, 165, 167, 171, 221, 222, 226, 246, 259, 270, 296, 325, 338, 345, 363, 394, 396, 457, 462, 473, 475, 481, 486, 490, 491, 500, 514, 516, and 520 In the amino acid sequence shown in SEQ ID NO:1.

In a preferred embodiment, the variant according to the invention is characterized in that it contains at least three deletions, substitutions and/or insertions wherein the deletion/insertion/substitution is at position 22 in the amino acid sequence shown in SEQ ID NO:1 or at a position corresponding to this position and another deletion/insertion/substitution is at position 462 in the amino acid sequence shown in SEQ ID NO:1 or at a position corresponding to this position and another deletion/insertion/substitution is at position 519 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 7, 13, 24, 33, 38, 54, 74, 75, 480, 41, 43, 81, 100, 165, 167, 171, 201, 221, 222, 226, 246, 259, 270, 296, 325, 338, 345, 363, 394, 396, 457, 473, 475, 481, 486, 490, 491, 500, 514, 516, and 520 in the amino acid sequence shown in SEQ ID NO:1.

In a preferred embodiment, the variant according to the invention is characterized in that it contains at least three deletions, substitutions and/or insertions wherein the deletion/insertion/substitution is at position 201 in the amino acid sequence shown in SEQ ID NO:1 or at a position corresponding to this position and another deletion/insertion/substitution is at position 462 in the amino acid sequence shown in SEQ ID NO:1 or at a position corresponding to this position and another deletion/insertion/substitution is at position 519 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 7, 13, 24, 33, 38, 74, 75, 480, 22, 41, 43, 54, 81, 100, 165, 167, 171, 221, 222, 226, 246, 259, 270, 296, 325, 338, 345, 363, 394, 396, 457, 473, 475, 481, 486, 490, 491, 500, 514, 516, and 520 in the amino acid sequence shown in SEQ ID NO:1.

In a preferred embodiment, the variant according to the invention is characterized in that it contains at least four deletions, substitutions and/or insertions wherein the deletion/insertion/substitution is at position 22 in the amino acid sequence shown in SEQ ID NO:1 or at a position corresponding to this position and another deletion/insertion/substitution is at position 201 in the amino acid sequence shown in SEQ ID NO:1 or at a position corresponding to this position and another deletion/insertion/substitution is at position 462 in the amino acid sequence shown in SEQ ID NO:1 or at a position corresponding to this position and another deletion/insertion/substitution is at position 519 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 7, 13, 24, 33, 38, 54, 74, 75, 480, 41, 43, 81, 100, 165, 167, 171, 221, 222, 226, 246, 259, 270, 296, 325, 338, 345, 363, 394, 396, 457, 473, 475, 481, 486, 490, 491, 500, 514, 516, and 520 in the amino acid sequence shown in SEQ ID NO:1.

In even more preferred embodiments, the variant according to the invention showing an improved activity in converting acetone into 3-hydroxyisovalerate (HIV) is characterized in that it has multiple mutations. As it is exemplified in the examples further below, variants have been found bearing multiple mutations which exhibit an increase in the reaction rate of the conversion of acetone into 3-hydroxyisovalerate (HIV). These variants bearing multiple mutations are summarized in the following Accordingly, in a very preferred embodiment, the variant according to the invention is characterized in that it comprises deletions, substitutions and/or insertions wherein the deletions/insertions/substitutions are at positions 22, 165, 201, 221, 222, 259, 296, 462, 481, 500 and 516 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M T165P A201T S221L I222Q G259D S296Q H462Y M481S V500S 8516N.

In another preferred embodiment, the variant according to the invention is characterized in that it comprises deletions, substitutions and/or insertions wherein the deletions/insertions/substitutions are at positions 22, 165, 201, 221, 222, 259, 296, 462, 473 and 490 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M T165P A201T S221L I222Q G259D S296Q H462Y N473G T490N.

In another preferred embodiment, the variant according to the invention is characterized in that it comprises deletions, substitutions and/or insertions wherein the deletions/insertions/substitutions are at positions 22, 165, 201, 221, 222, 259, 296, 462 and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M T165P A201T S221L I222Q G259D S296Q H462Y V500S.

In another preferred embodiment, the variant according to the invention is characterized in that it comprises deletions, substitutions and/or insertions wherein the deletions/insertions/substitutions are at positions 22, 165, 201, 221, 222, 259, 296, 462, 473, 481, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M T165P A201T S221L I222Q G259D S296Q H462Y N473G M481S V500S.

In another preferred embodiment, the variant according to the invention is characterized in that it comprises deletions, substitutions and/or insertions wherein the deletions/insertions/substitutions are at positions 22, 165, 201, 221, 222, 259, 296, 462, 473 and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M T165P A201T S221L I222Q G259D S296Q H462Y N473G V500S.

In another preferred embodiment, the variant according to the Invention is characterized in that it comprises deletions, substitutions and/or insertions wherein the deletions/insertions/substitutions are at positions 22, 43, 165, 201, 221, 222, 259, 462, 481 and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M D43V T165P A201T S221L I222Q G259D H462Y M481S V500S.

In another preferred embodiment, the variant according to the invention is characterized in that it comprises deletions, substitutions and/or insertions wherein the deletions/insertions/substitutions are at positions 22, 43, 81, 165, 201, 221, 222, 259, 296, 462, 500 and 514 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M D43V S81R T165P A201T S221L I222Q G259D S296Q H462Y V500S V514S.

In another preferred embodiment, the variant according to the invention is characterized in that it comprises deletions, substitutions and/or insertions wherein the deletions/insertions/substitutions are at positions 22, 43, 165, 201, 221, 222, 259, 296, 394, 457, 462, 481, 500 and 514 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M D43V T165P A201T S221L I222Q G259D S296Q P394S R457C H462Y M481S V500S V514S.

In another preferred embodiment, the variant according to the invention is characterized in that it comprises deletions, substitutions and/or insertions wherein the deletions/insertions/substitutions are at positions 22, 165, 201, 221, 222, 259, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M T165P A201T S221L I222Q G259D H462Y.

In another preferred embodiment, the variant according to the invention is characterized in that it comprises deletions, substitutions and/or insertions wherein the deletions/insertions/substitutions are at positions 22, 165, 201, 221, 222, 259, 296, 396, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M T165P A201T S221L I222Q G259D S296Q S396N H462Y.

In another preferred embodiment, the variant according to the invention is characterized in that it comprises deletions, substitutions and/or insertions wherein the deletions/insertions/substitutions are at positions 22, 165, 201, 221, 222, 259, 296, 396, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M T165P A201T S221L I222Q G259D S296Q S396N H462Y.

In another preferred embodiment, the variant according to the invention is characterized in that it comprises deletions, substitutions and/or insertions wherein the deletions/insertions/substitutions are at positions 22, 201, 221, 222, 259, 296, 345, 363, 462, 473, 481, 500, and 514 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T S221L I222Q G259D S296Q Y345F Q363R H462Y N473G M481S V500S V514S.

In another preferred embodiment, the variant according to the invention is characterized in that it comprises deletions, substitutions and/or insertions wherein the deletions/insertions/substitutions are at positions 22, 43, 165, 201, 221, 222, 259, 296, 462, 481, and 514 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M D43V T165P A201T S221L I222Q G259D S296Q H462Y M481S V514S.

In another preferred embodiment, the variant according to the invention is characterized in that it comprises deletions, substitutions and/or Insertions wherein the deletions/insertions/substitutions are at positions 22, 201, 221, 222, 259, 296, 462, 473, and 481 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T S221L I222Q G259D S296Q H462Y N473G M481S.

In another preferred embodiment, the variant according to the invention is characterized in that it comprises deletions, substitutions and/or insertions wherein the deletions/insertions/substitutions are at positions 22, 201, 221, 222, 259, 296, 462, and 486 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T S221L I222Q G259D S296Q H462Y S486R.

In another preferred embodiment, the variant according to the invention is characterized in that it comprises deletions, substitutions and/or insertions wherein the deletions/insertions/substitutions are at positions 22, 201, 221, 222, 259, 462, 473, 481, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T S221L I222Q G259D H462Y N473G M481S V500S.

In another preferred embodiment, the variant according to the invention is characterized in that it comprises deletions, substitutions and/or insertions wherein the deletions/insertions/substitutions are at positions 22, 201, 221, 222, 259, 296, 462, 473, 481, 500, and 514 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T S221L I222Q G259D S296Q H462Y N473G M481S V500S V514S.

In another preferred embodiment, the variant according to the invention is characterized in that it comprises deletions, substitutions and/or insertions wherein the deletions/insertions/substitutions are at positions 22, 201, 221, 222, 259, 296, 462, 473, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T S221L I222Q G259D S296Q H462Y N473G V500S.

In another preferred embodiment, the variant according to the invention is characterized in that it comprises deletions, substitutions and/or insertions wherein the deletions/insertions/substitutions are at positions 22, 75, 165, 201, 221, 222, 296, 462, 473, 475, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165P A201T S221L I222K S296Q H462Y N473D H475R V500S.

In another preferred embodiment, the variant according to the invention is characterized in that it comprises deletions, substitutions and/or insertions wherein the deletions/insertions/substitutions are at positions 22, 75, 165, 201, 221, 222, 259, 296, 462, and 475 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165Q A201T S221L I222Q G259D S296Q H462Y H475R.

In another preferred embodiment, the variant according to the invention is characterized in that it comprises deletions, substitutions and/or insertions wherein the deletions/insertions/substitutions are at positions 22, 75, 165, 201, 221, 222, 259, 296, 462, 473, and 481 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165P A201T S221L I222K G259D S296Q H462Y N473G M481S.

In another preferred embodiment, the variant according to the invention is characterized in that it comprises deletions, substitutions and/or insertions wherein the deletions/insertions/substitutions are at positions 22, 75, 165, 201, 221, 222, 259, 296, 462, 473, and 481 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165P A201T S221L I222K G259D S296Q H462Y N473G M481S.

In another preferred embodiment, the variant according to the invention is characterized in that it comprises deletions, substitutions and/or insertions wherein the deletions/insertions/substitutions are at positions 22, 201, 221, 259, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T S221L G259D H462Y.

In another preferred embodiment, the variant according to the invention is characterized in that it comprises deletions, substitutions and/or insertions wherein the deletions/insertions/substitutions are at positions 22, 165, 201, 221, 222, 226, 246, 259, 296, 462, 473, 475, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M T165Q A201T S221L I222K L226M K246R G259D S296Q H462Y N473D H475R V500S.

In another preferred embodiment, the variant according to the invention is characterized in that it comprises deletions, substitutions and/or insertions wherein the deletions/insertions/substitutions are at positions 22, 201, 221, 222, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T S221L I222Q H462Y.

In another preferred embodiment, the variant according to the invention is characterized in that it comprises deletions, substitutions and/or insertions wherein the deletions/insertions/substitutions are at positions 22, 201, 221, 222, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T S221L I222K H462Y.

In another preferred embodiment, the variant according to the invention is characterized in that it comprises deletions, substitutions and/or insertions wherein the deletions/insertions/substitutions are at positions 22, 201, 221, 222, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T S221L I222H H462Y.

In another preferred embodiment, the variant according to the invention is characterized in that it comprises deletions, substitutions and/or insertions wherein the deletions/insertions/substitutions are at positions 22, 201, 221, 462, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T S221L H462Y V500S.

In another preferred embodiment, the variant according to the invention is characterized in that it comprises deletions, substitutions and/or insertions wherein the deletions/insertions/substitutions are at positions 22, 201, 221, 296, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T S221L S296Q H462Y.

In another preferred embodiment, the variant according to the invention is characterized in that it comprises deletions, substitutions and/or insertions wherein the deletions/insertions/substitutions are at positions 22, 201, 221, 462, and 491 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T S221L H462Y E491A.

In another preferred embodiment, the variant according to the invention is characterized in that it comprises deletions, substitutions and/or insertions wherein the deletions/insertions/substitutions are at positions 22, 201, 221, 462, and 475 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T S221L H462Y H475R.

In another preferred embodiment, the variant according to the invention is characterized in that it comprises deletions, substitutions and/or insertions wherein the deletions/insertions/substitutions are at positions 22, 201, 221, 226, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T S221L L226M H462Y.

In another preferred embodiment, the variant according to the invention is characterized in that it comprises deletions, substitutions and/or insertions wherein the deletions/insertions/substitutions are at positions 22, 201, 221, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T S221L H462Y.

In another preferred embodiment, the variant according to the invention is characterized in that it comprises deletions, substitutions and/or insertions wherein the deletions/insertions/substitutions are at positions 22, 201, 270, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T L270I H462Y.

In another preferred embodiment, the variant according to the invention is characterized in that it comprises deletions, substitutions and/or insertions wherein the deletions/insertions/substitutions are at positions 22, 201, 270, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T L270M H462Y.

In another preferred embodiment, the variant according to the invention is characterized in that it comprises deletions, substitutions and/or insertions wherein the deletions/insertions/substitutions are at positions 22, 100, 201, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K100L A201T H462Y.

In another preferred embodiment, the variant according to the invention is characterized in that it comprises deletions, substitutions and/or insertions wherein the deletions/insertions/substitutions are at positions 22, 201, 246, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T K246R H462Y.

In another preferred embodiment, the variant according to the invention is characterized in that it comprises deletions, substitutions and/or insertions wherein the deletions/insertions/substitutions are at positions 22, 201, 462, and 520 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T H462Y H520S.

In another preferred embodiment, the variant according to the invention is characterized in that it comprises deletions, substitutions and/or insertions wherein the deletions/insertions/substitutions are at positions 22, 201, 462, and 519 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T H462Y E519D.

In another preferred embodiment, the variant according to the invention is characterized in that it comprises deletions, substitutions and/or insertions wherein the deletions/insertions/substitutions are at positions 22, 201, 325, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T E325A H462Y.

In another preferred embodiment, the variant according to the invention is characterized in that it comprises deletions, substitutions and/or insertions wherein the deletions/insertions/substitutions are at positions 22, 41, 201, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M G41S A201T H462Y.

In another preferred embodiment, the variant according to the invention Is characterized in that it comprises deletions, substitutions and/or insertions wherein the deletions/insertions/substitutions are at positions 22 and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M H462Y.

In another preferred embodiment, the variant according to the invention is characterized in that it comprises deletions, substitutions and/or insertions wherein the deletions/insertions/substitutions are at positions 22, 462, and 519 In the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M H462Y E519D.

In another preferred embodiment, the variant according to the invention is characterized in that it comprises deletions, substitutions and/or insertions wherein the deletions/insertions/substitutions are at positions 22, 201, and 519 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T E519D.

In another preferred embodiment, the variant according to the invention is characterized in that it comprises deletions, substitutions and/or insertions wherein the deletions/insertions/substitutions are at positions 22, 201, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T H462Y.

In another preferred embodiment, the variant according to the invention is characterized in that it comprises deletions, substitutions and/or insertions wherein the deletions/insertions/substitutions are at positions 22, and 201 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T.

In another preferred embodiment, the variant according to the invention is characterized in that it comprises deletions, substitutions and/or insertions wherein the deletions/insertions/substitutions are at positions 201, 462, and 519 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

A201T H462Y E519D.

In another preferred embodiment, the variant according to the invention is characterized in that it comprises deletions, substitutions and/or insertions wherein the deletions/insertions/substitutions are at positions 22, and 519 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M E519D.

In another preferred embodiment, the variant according to the invention is characterized in that it comprises deletions, substitutions and/or insertions wherein the deletions/insertions/substitutions are at positions 462, and 519 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

H462Y E519D.

In another preferred embodiment, the variant according to the invention is characterized in that it comprises deletions, substitutions and/or insertions wherein the deletions/insertions/substitutions are at positions 201, and 462 in the amino acid sequence shown in SEQ ID NO:1 or at positions corresponding to these positions.

Preferably, such a variant has the following substitutions in the amino acid sequence shown in SEQ ID NO:1 or at positions corresponding to these positions:

A201T H462Y.

In another preferred embodiment, the variant according to the invention is characterized in that it comprises deletions, substitutions and/or insertions wherein the deletions/insertions/substitutions are at positions 201 and 519 in the amino acid sequence shown in SEQ ID NO:1 or at positions corresponding to these positions.

Preferably, such a variant has the following substitutions in the amino acid sequence shown in SEQ ID NO:1 or at positions corresponding to these positions:

A201T E519D.

In another preferred embodiment, the variant according to the invention is characterized in that it comprises deletions, substitutions and/or insertions wherein the deletions/insertions/substitutions are at positions 22, 201, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T H462Y.

In another preferred embodiment, the variant according to the invention is characterized in that it comprises deletions, substitutions and/or insertions wherein the deletions/insertions/substitutions are at positions 22, 201, 221, 259, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T S221L G259D H462Y.

In another preferred embodiment, the variant according to the invention is characterized in that it comprises deletions, substitutions and/or insertions wherein the deletions/insertions/substitutions are at positions 22, 165, 201, 221, 222, 259, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M T165P A201T S221L I222Q G259D H462Y.

In another preferred embodiment, the variant according to the invention is characterized in that it comprises deletions, substitutions and/or insertions wherein the deletions/insertions/substitutions are at positions 22, 75, 165, 201, 221, 222, 259, 296, 462, 473, and 481 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165P A201T S221L I222K G259D S296Q H462Y N473G M481S.

In another preferred embodiment, the variant according to the invention is characterized in that it comprises deletions, substitutions and/or insertions wherein the deletions/insertions/substitutions are at positions 22, 75, 165, 201, 221, 222, 259, 296, 462, 473, and 481 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165P A201T S221L I222K G259D S296Q H462Y N473G M481S.

In another preferred embodiment, the variant according to the invention is characterized in that it comprises deletions, substitutions and/or insertions wherein the deletions/insertions/substitutions are at positions 22, 201, 221, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T S221L H462Y.

In another preferred embodiment, the variant according to the invention is characterized in that it comprises deletions, substitutions and/or insertions wherein the deletions/insertions/substitutions are at positions 22, 165, 201, 221, 222, 226, 246, 259, 296, 462, 473, 475, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M T165Q A201T S221L I222K L226M K246R G259D S296Q H462Y N473D H475R V500S.

In another preferred embodiment, the variant according to the invention is characterized in that it comprises deletions, substitutions and/or insertions wherein the deletions/insertions/substitutions are at positions 22, 165, 201, 221, 222, 226, 246, 259, 296, 462, 473, 475, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M T165Q A201T S221L I222K L226M K246R G259D S296Q H462Y N473D H475R V500S.

In another preferred embodiment, the variant according to the invention is characterized in that it comprises deletions, substitutions and/or insertions wherein the deletions/insertions/substitutions are at positions 22, 75, 165, 201, 221, 222, 259, 296, 462, and 475 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165Q A201T S221L I222Q G259D S296Q H462Y H475R.

In another preferred embodiment, the variant according to the invention is characterized in that it comprises deletions, substitutions and/or insertions wherein the deletions/insertions/substitutions are at positions 22, 201, 221, 222, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T S221L I222K H462Y.

In another preferred embodiment, the variant according to the invention is characterized in that it comprises deletions, substitutions and/or insertions wherein the deletions/insertions/substitutions are at positions 22, 75, 165, 201, 221, 222, 296, 462, 473, 475, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165P A201T S221L I222K S296Q H462Y N473D H475R V500S.

In another preferred embodiment, the variant according to the invention is characterized in that it comprises deletions, substitutions and/or insertions wherein the deletions/insertions/substitutions are at positions 165, 222, 296, 481, 500, and 516 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

T165P I222Q S296Q M481S V500S S516N.

In another preferred embodiment, the variant according to the invention is characterized in that it comprises deletions, substitutions and/or insertions wherein the deletions/insertions/substitutions are at positions 165, 222, 296, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

T165P I222Q S296Q V500S.

In another preferred embodiment, the variant according to the invention is characterized in that it comprises deletions, substitutions and/or insertions wherein the deletions/insertions/substitutions are at positions 165, 222, 296, 473, 481, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

T165P I222Q S296Q N473G M481S V500S.

In another preferred embodiment, the variant according to the invention is characterized in that it comprises deletions, substitutions and/or insertions wherein the deletions/insertions/substitutions are at positions 22, 75, 165, 201, 221, 222, 259, 296, 462, and 475 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165Q A201T S221L I222Q G259D S296Q H462Y H475R.

In another preferred embodiment, the variant according to the invention is characterized in that it comprises deletions, substitutions and/or insertions wherein the deletions/insertions/substitutions are at positions 22, 24, 75, 100, 165, 201, 221, 222, 226, 246, 259, 270, 462, 473, 480, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M I24M K75N K100L T165P A201T S221L I222Q L226M K246R G259D L270I H462Y N473D G480C V500S.

In another preferred embodiment, the variant according to the invention is characterized in that it comprises deletions, substitutions and/or insertions wherein the deletions/insertions/substitutions are at positions 165, 222, 296, 473, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

T165P I222Q S296Q N473G V500S.

In another preferred embodiment, the variant according to the Invention is characterized in that it comprises deletions, substitutions and/or insertions wherein the deletions/insertions/substitutions are at positions 43, 165, 222, 481, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

D43V T165P I222Q M481S V500S.

In another preferred embodiment, the variant according to the invention is characterized in that it comprises deletions, substitutions and/or insertions wherein the deletions/insertions/substitutions are at positions 22, 75, 165, 201, 221, 222, 226, 259, 270, 296, 462, 473, 480, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165Q A201T S221L I222Q L226M G259D L270M S296Q H462Y N473D G480C V500S.

In another preferred embodiment, the variant according to the invention is characterized in that it comprises deletions, substitutions and/or insertions wherein the deletions/insertions/substitutions are at positions 22, 24, 165, 201, 221, 222, 226, 259, 270, 296, 462, and 475 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M I24M T165P A201T S221L I222K L226M G259D L270M S296Q H462Y H475R.

In another preferred embodiment, the variant according to the invention is characterized in that it comprises deletions, substitutions and/or insertions wherein the deletions/insertions/substitutions are at positions 22, 75, 165, 201, 221, 222, 259, 296, 462, 473, and 481 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165P A201T S221L I222K G259D S296Q H462Y N473G M481S.

In another preferred embodiment, the variant according to the invention is characterized in that it comprises deletions, substitutions and/or insertions wherein the deletions/insertions/substitutions are at positions 43, 165, 222, 296, 394, 457, 481, 500, and 514 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

D43V T165P I222Q S296Q P394S R457C M481S V500S V514S.

In another preferred embodiment, the variant according to the invention is characterized in that it comprises deletions, substitutions and/or insertions wherein the deletions/insertions/substitutions are at positions 22, 75, 165, 201, 221, 222, 226, 246, 259, 462, 473, and 480 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165P A201T S221L I222H L226M K246R G259D H462Y N473D G480C.

In another preferred embodiment, the variant according to the invention is characterized in that it comprises deletions, substitutions and/or insertions wherein the deletions/insertions/substitutions are at positions 165, 222, 296, and 396 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

T165P I222Q S296Q S396N.

In another preferred embodiment, the variant according to the invention is characterized in that it comprises deletions, substitutions and/or insertions wherein the deletions/insertions/substitutions are at positions 22, 75, 201, 221, 222, 259, 296, 462, 473, 480, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N A201T S221L I222H G259D S296Q H462Y N473G G480C V500S.

In another preferred embodiment, the variant according to the invention is characterized in that it comprises deletions, substitutions and/or insertions wherein the deletions/insertions/substitutions are at positions 22, 75, 165, 201, 221, 222, 296, 462, 473, 475, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165P A201T S221L I222K S296Q H462Y N473D H475R V500S.

In another preferred embodiment, the variant according to the invention is characterized in that it comprises deletions, substitutions and/or insertions wherein the deletions/insertions/substitutions are at positions 222, 296, 345, 363, 473, 481, 500, and 514 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

I222Q S296Q Y345F Q363R N473G M481S V500S V514S.

In another preferred embodiment, the variant according to the invention is characterized in that it comprises deletions, substitutions and/or insertions wherein the deletions/insertions/substitutions are at positions 43, 165, 222, 296, 481, and 514 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

D43V T165P I222Q S296Q M481S V514S.

In another preferred embodiment, the variant according to the invention is characterized in that it comprises deletions, substitutions and/or insertions wherein the deletions/insertions/substitutions are at positions 222, 296, 473, and 481 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

I222Q S296Q N473G M481S.

In another preferred embodiment, the variant according to the invention is characterized in that it comprises deletions, substitutions and/or insertions wherein the deletions/insertions/substitutions are at positions 222, 296, and 486 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

I222Q S296Q S486R.

In another preferred embodiment, the variant according to the invention is characterized in that it comprises deletions, substitutions and/or insertions wherein the deletions/insertions/substitutions are at positions 22, 24, 75, 165, 201, 221, 222, 226, 246, 259, 296, 462, 473, 480, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M I24M K75N T165Q A201T S221L I222Q L226M K246R G259D S296Q H462Y N473D G480C V500S.

In another preferred embodiment, the variant according to the invention is characterized in that it comprises deletions, substitutions and/or insertions wherein the deletions/insertions/substitutions are at positions 22, 165, 201, 221, 222, 226, 246, 259, 296, 462, 473, 475, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M T165Q A201T S221L I222K L226M K246R G259D S296Q H462Y N473D H475R V500S.

In another preferred embodiment, the variant according to the invention is characterized in that it comprises deletions, substitutions and/or insertions wherein the deletions/insertions/substitutions are at positions 22, 201, 24, 75, 165, 221, 222, 226, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T I24M K75N T165P S221L I222K L226M H462Y.

In another preferred embodiment, the variant according to the invention is characterized in that it comprises deletions, substitutions and/or insertions wherein the deletions/insertions/substitutions are at positions 222, 473, 481, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

I222Q N473G M481S V500S.

In another preferred embodiment, the variant according to the invention is characterized in that it comprises deletions, substitutions and/or insertions wherein the deletions/insertions/substitutions are at positions 222, 296, 473, 481, 500, and 514 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

I222Q S296Q N473G M481S V500S V514S.

In another preferred embodiment, the variant according to the invention is characterized in that it comprises deletions, substitutions and/or insertions wherein the deletions/insertions/substitutions are at positions 22, 24, 75, 165, 201, 221, 222, 226, 246, 259, 270, 296, 462, 473, 480, 481, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M I24M K75N T165Q A201T S221L I222Q L226M K246R G259D L270I S296Q H462Y N473D G480C M481S V500S.

In another preferred embodiment, the variant according to the invention is characterized in that it comprises deletions, substitutions and/or insertions wherein the deletions/insertions/substitutions are at positions 222, 296, 473, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

I222Q S296Q N473G V500S.

In another preferred embodiment, the variant according to the invention is characterized in that it comprises deletions, substitutions and/or insertions wherein the deletions/insertions/substitutions are at positions 22, 75, 165, 201, 221, 462, 222, 296, 480, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165Q A201T S221L H462Y I222K S296Q G480C V500S.

In another preferred embodiment, the variant according to the invention is characterized in that it comprises deletions, substitutions and/or insertions wherein the deletions/insertions/substitutions are at positions 22, 75, 165, 201, 221, 222, 246, 259, 462, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165P A201T S221L I222K K246R G259D H462Y V500S.

In another preferred embodiment, the variant according to the invention is characterized in that it comprises deletions, substitutions and/or insertions wherein the deletions/insertions/substitutions are at positions 22, 24, 165, 201, 221, 222, 226, 259, 462, 475, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M I24M T165Q A201T S221L I222K L226M G259D H462Y H475R V500S.

In another preferred embodiment, the variant according to the invention is characterized in that it comprises deletions, substitutions and/or insertions wherein the deletions/Insertions/substitutions are at positions 22, 24, 75, 201, 221, 222, 226, 259, 462, 473, and 481 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M I24M K75N A201T S221L I222Q L226M G259D H462Y N473D M481S.

In another preferred embodiment, the variant according to the invention is characterized in that it comprises deletions, substitutions and/or insertions wherein the deletions/insertions/substitutions are at positions 22, 24, 75, 100, 165, 201, 221, 222, 246, 259, 296, 462, 473, 481, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M I24M K75N K100L T165P A201T S221L I222K K246R G259D S296Q H462Y N473G M481S V500S.

In another preferred embodiment, the variant according to the invention is characterized in that it comprises deletions, substitutions and/or insertions wherein the deletions/insertions/substitutions are at positions 22, 75, 201, 221, 222, 226, 462, 473, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N A201T S221L I222Q L226M H462Y N473D V500S.

In another preferred embodiment, the variant according to the invention is characterized in that it comprises deletions, substitutions and/or insertions wherein the deletions/insertions/substitutions are at positions 22, 165, 201, 221, 222, 226, 259, 270, 462, 473, 475, and 480 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M T165P A201T S221L I222Q L226M G259D L270I H462Y N473G H475R G480C.

In another preferred embodiment, the variant according to the invention is characterized in that it comprises deletions, substitutions and/or insertions wherein the deletions/insertions/substitutions are at positions 7, 13, 22, 75, 165, 201, 221, 222, 259, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L7I W13L L22M K75N T165P A201T S221L I222Q G259D H462Y.

In another preferred embodiment, the variant according to the invention is characterized in that it comprises deletions, substitutions and/or insertions wherein the deletions/insertions/substitutions are at positions 22, 24, 75, 165, 201, 221, 222, 259, 462, and 480 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M I24M K75N T165Q A201T S221L I222H G259D H462Y G480C.

In another preferred embodiment, the variant according to the invention is characterized in that it comprises deletions, substitutions and/or insertions wherein the deletions/insertions/substitutions are at positions 22, 24, 75, 201, 221, 222, 246, 296, 462, 473, and 475 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M I24M K75N A201T S221L I222Q K246R S296Q H462Y N473G H475R.

In another preferred embodiment, the variant according to the invention is characterized in that it comprises deletions, substitutions and/or insertions wherein the deletions/insertions/substitutions are at positions 22, 201, 221, 462, 165, 222, 259, 296, 473, and 480 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T S221L H462Y T165Q I222H G259D S296Q N473G G480C.

In another preferred embodiment, the variant according to the invention is characterized in that it comprises deletions, substitutions and/or insertions wherein the deletions/insertions/substitutions are at positions 22, 24, 75, 165, 201, 221, 222, 226, 246, 259, 462, 475, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M I24M K75N T165P A201T S221L I222K L226M K246R G259D H462Y H475R V500S.

In another preferred embodiment, the variant according to the invention is characterized in that it comprises deletions, substitutions and/or insertions wherein the deletions/insertions/substitutions are at positions 22, 24, 75, 165, 201, 221, 222, 246, 296, 462, 473, 480, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M I24M K75N T165Q A201T S221L I222H K246R S296Q H462Y N473G G480C V500S.

In another preferred embodiment, the variant according to the invention is characterized in that it comprises deletions, substitutions and/or insertions wherein the deletions/insertions/substitutions are at positions 22, 75, 165, 201, 221, 462, 222, 296, 475, 480, and 481 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165Q A201T S221L H462Y I222Q S296Q H475R G480C M481S.

In another preferred embodiment, the variant according to the invention is characterized in that it comprises deletions, substitutions and/or insertions wherein the deletions/insertions/substitutions are at positions 22, 75, 165, 201, 221, 222, 259, 270, 296, 462, 475, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165P A201T S221L I222Q G259D L270I S296Q H462Y H475R V500S.

In another preferred embodiment, the variant according to the invention is characterized in that it comprises deletions, substitutions and/or insertions wherein the deletions/insertions/substitutions are at positions 22, 24, 75, 100, 165, 201, 221, 222, 226, 246, 259, 270, 296, 462, 473, and 475 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M I24M K75N K100L T165P A201T S221L I222H L226M K246R G259D L270M S296Q H462Y N473D H475R.

In another preferred embodiment, the variant according to the invention is characterized in that it comprises deletions, substitutions and/or insertions wherein the deletions/insertions/substitutions are at positions 22, 24, 75, 201, 221, 222, 259, 270, 296, 462, and 475 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M I24M K75N A201T S221L I222H G259D L270I S296Q H462Y H475R.

In another preferred embodiment, the variant according to the invention is characterized in that it comprises deletions, substitutions and/or insertions wherein the deletions/insertions/substitutions are at positions 22, 24, 75, 100, 165, 201, 221, 222, 226, 246, 259, 270, 462, 473, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M I24M K75N K100L T165P A201T S221L I222K L226M K246R G259D L270M H462Y N473D V500S.

In another preferred embodiment, the variant according to the invention is characterized in that it comprises deletions, substitutions and/or insertions wherein the deletions/insertions/substitutions are at positions 22, 24, 75, 165, 201, 221, 226, 246, 259, 270, 296, 462, 475, 500, and 514 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M I24M K75N T165Q A201T S221L L226M K246R G259D L270I S296Q H462Y H475R V500S V514S.

In another preferred embodiment, the variant according to the invention is characterized in that it comprises deletions, substitutions and/or insertions wherein the deletions/insertions/substitutions are at positions 22, 75, 165, 201, 221, 222, 259, 296, 462, and 475 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165Q A201T S221L I222Q G259D S296Q H462Y H475R.

In another preferred embodiment, the variant according to the invention is characterized in that it comprises deletions, substitutions and/or insertions wherein the deletions/insertions/substitutions are at positions 22, 24, 75, 165, 201, 221, 222, 226, 259, 462, and 473 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M I24M K75N T165Q A201T S221L I222K L226M G259D H462Y N473G.

In another preferred embodiment, the variant according to the invention is characterized in that it comprises deletions, substitutions and/or insertions wherein the deletions/insertions/substitutions are at positions 22, 75, 165, 201, 221, 222, 296, 462, 473, 475, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165P A201T S221L I222K S296Q H462Y N473D H475R V500S.

In another preferred embodiment, the variant according to the invention is characterized in that it comprises deletions, substitutions and/or insertions wherein the deletions/Insertions/substitutions are at positions 22, 24, 75, 165, 201, 221, 222, 226, 246, 259, 270, 296, 462, 473, and 480 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M I24M K75N T165Q A201T S221L I222Q L226M K246R G259D L270M S296Q H462Y N473D G480C.

In another preferred embodiment, the variant according to the invention is characterized in that it comprises deletions, substitutions and/or insertions wherein the deletions/insertions/substitutions are at positions 22, 75, 201, 221, 259, 296, 462, 473, and 480 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N A201T S221L G259D S296Q H462Y N473G G480C.

In another preferred embodiment, the variant according to the invention is characterized in that it comprises deletions, substitutions and/or insertions wherein the deletions/insertions/substitutions are at positions 22, 75, 165, 201, 221, 222, 259, 296, 462, 473, and 481 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165P A201T S221L I222K G259D S296Q H462Y N473G M481S.

In another preferred embodiment, the variant according to the Invention is characterized in that it comprises deletions, substitutions and/or insertions wherein the deletions/insertions/substitutions are at positions 22, 24, 75, 165, 201, 221, 222, 226, 246, 270, 296, 462, 473, 480, 481, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M I24M K75N T165P A201T S221L I222K L226M K246R L270M S296Q H462Y N473G G480C M481S V500S.

In another preferred embodiment, the variant according to the invention is characterized in that it comprises deletions, substitutions and/or insertions wherein the deletions/insertions/substitutions are at positions 22, 75, 165, 201, 221, 222, 246, 259, 270, 296, 462, 473, 480, and 481 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165Q A201T S221L I222H K246R G259D L270I S296Q H462Y N473G G480C M481S.

In another preferred embodiment, the variant according to the invention is characterized in that it comprises deletions, substitutions and/or insertions wherein the deletions/insertions/substitutions are at positions 22, 24, 75, 165, 201, 221, 222, 246, 259, 462, 473, 480, 500, and 519 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M I24M K75N T165Q A201T S221L I222R K246R G259D H462Y N473D G480C V500S E519D.

In another preferred embodiment, the variant according to the invention is characterized in that it comprises deletions, substitutions and/or insertions wherein the deletions/insertions/substitutions are at positions 22, 75, 165, 201, 221, 222, 226, 246, 259, 462, 473, and 480 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165P A201T S221L I222H L226M K246R G259D H462Y N473D G480C.

In another preferred embodiment, the variant according to the invention is characterized in that it comprises deletions, substitutions and/or insertions wherein the deletions/insertions/substitutions are at positions 22, 165, 201, 221, 222, 226, 246, 259, 296, 462, 473, 475, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M T165Q A201T S221L I222K L226M K246R G259D S296Q H462Y N473D H475R V500S.

In another preferred embodiment, the variant according to the invention is characterized in that it comprises deletions, substitutions and/or insertions wherein the deletions/insertions/substitutions are at positions 22, 24, 75, 165, 201, 221, 222, 226, 296, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M I24M K75N T165P A201T S221L I222K L226M S296Q H462Y.

In another preferred embodiment, the variant according to the invention is characterized in that it comprises deletions, substitutions and/or insertions wherein the deletions/insertions/substitutions are at positions 22, 24, 75, 100, 165, 201, 221, 222, 246, 259, 270, 462, 473, 480, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M I24M K75N K100L T165P A201T S221L I222H K246R G259D L270M H462Y N473G G480C V500S.

In another preferred embodiment, the variant according to the invention is characterized in that it comprises deletions, substitutions and/or insertions wherein the deletions/insertions/substitutions are at positions 22, 75, 165, 201, 221, and 462 in the amino acid sequence shown in SEQ ID NO:1 or at positions corresponding to these positions. Preferably, such a variant has the following substitutions in the amino acid sequence shown in SEQ ID NO:1 or at positions corresponding to this position:

L22M K75N T165Q A201T S221L H462Y.

In another preferred embodiment, the variant according to the invention is characterized in that it comprises deletions, substitutions and/or insertions wherein the deletions/insertions/substitutions are at positions 22, 24, 75, 165, 201, 221, 222, 246, 259, 270, 462, 473, and 514 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M I24M K75N T165Q A201T S221L I222Q K246R G259D L270M H462Y N473G V514S.

In another preferred embodiment, the variant according to the invention is characterized in that it comprises deletions, substitutions and/or insertions wherein the deletions/insertions/substitutions are at positions 22, 24, 75, 100, 165, 201, 221, 222, 246, 259, 270, 296, 462, 473, and 481 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M I24M K75N K100L T165P A201T S221L I222K K246R G259D L270M S296Q H462Y N473G M481S.

In another preferred embodiment, the variant according to the invention is characterized in that it comprises deletions, substitutions and/or insertions wherein the deletions/insertions/substitutions are at positions 22, 75, 165, 201, 221, 226, 259, 270, 462, 473, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165Q A201T S221L L226M G259D L270I H462Y N473D V500S.

In another preferred embodiment, the variant according to the invention is characterized in that it comprises deletions, substitutions and/or insertions wherein the deletions/insertions/substitutions are at positions 22, 75, 201, 221, 222, 226, 246, 296, 462, 480, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N A201T S221L I222Q L226M K246R S296Q H462Y G480C V500S.

In another preferred embodiment, the variant according to the invention is characterized in that it comprises deletions, substitutions and/or insertions wherein the deletions/insertions/substitutions are at positions 22, 24, 201, 221, 222, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M I24M A201T S221L I222Q H462Y.

In another preferred embodiment, the variant according to the invention is characterized in that it comprises deletions, substitutions and/or insertions wherein the deletions/insertions/substitutions are at positions 22, 24, 75, 165, 201, 221, 222, 226, 270, 462, and 475 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M I24M K75N T165Q A201T S221L I222H L226M L270M H462Y H475R.

In another preferred embodiment, the variant according to the invention is characterized in that it comprises deletions, substitutions and/or insertions wherein the deletions/insertions/substitutions are at positions 22, 24, 75, 165, 201, 221, 222, 226, 246, 259, 270, 296, 462, 475, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M I24M K75N T165Q A201T S221L I222Q L226M K246R G259D L270M S296Q H462Y H475R V500S.

In another preferred embodiment, the variant according to the invention is characterized in that it comprises deletions, substitutions and/or insertions wherein the deletions/insertions/substitutions are at positions 22, 24, 75, 165, 201, 221, 226, 246, 259, 296, 462, 480, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M I24M K75N T165Q A201T S221L L226M K246R G259D S296Q H462Y G480C V500S.

In another preferred embodiment, the variant according to the invention is characterized in that it comprises deletions, substitutions and/or Insertions wherein the deletions/insertions/substitutions are at positions 22, 75, 165, 201, 221, 222, 226, 246, 259, 270, 462, 473, and 475 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165P A201T S221L I222K L226M K246R G259D L270M H462Y N473D H475R.

In another preferred embodiment, the variant according to the invention is characterized in that it comprises deletions, substitutions and/or insertions wherein the deletions/insertions/substitutions are at positions 22, 24, 75, 201, 221, 222, 270, 296, 462, and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M I24M K75N A201T S221L I222H L270M S296Q H462Y V500S.

In another preferred embodiment, the variant according to the invention is characterized in that it comprises deletions, substitutions and/or insertions wherein the deletions/insertions/substitutions are at positions 7, 13, 22, 75, 165, 201, 221, 222, 259, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L71 W13R L22M K75N T165P A201T S221L I222K G259D H462Y.

In another preferred embodiment, the variant according to the Invention is characterized in that it comprises deletions, substitutions and/or insertions wherein the deletions/insertions/substitutions are at positions 7, 13, 22, 75, 165, 201, 221, 222, 259, 338 and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L71 W13R L22M K75N T165P A201T S221L I222K G259D S338P H462Y.

In another preferred embodiment, the variant according to the invention is characterized in that it comprises deletions, substitutions and/or insertions wherein the deletions/insertions/substitutions are at positions 7, 13, 22, 75, 165, 171, 201, 221, 222, 259, 325 and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L71 W13R L22M K75N T165P T171A A201T S221L I222K G259D E325L H462Y.

In another preferred embodiment, the variant according to the Invention is characterized in that it comprises deletions, substitutions and/or insertions wherein the deletions/insertions/substitutions are at positions 7, 13, 22, 75, 165, 171, 201, 221, 222, 259, 325 and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L71 W13R L22M K75N T165P T171G A201T S221L I222K G259D E325V H462Y.

In another preferred embodiment, the variant according to the invention is characterized in that it comprises deletions, substitutions and/or insertions wherein the deletions/insertions/substitutions are at positions 7, 13, 22, 54, 75, 165, 201, 221, 222, 259, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L71 W13R L22M A54G K75N T165P A201T S221L I222K G259D H462Y.

In another preferred embodiment, the variant according to the invention is characterized in that it comprises deletions, substitutions and/or insertions wherein the deletions/insertions/substitutions are at positions 7, 13, 22, 75, 165, 171, 201, 221, 222, 259, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L71 W13R L22M K75N T165P T171A A201T S221L I222K G259D H462Y.

In another preferred embodiment, the variant according to the invention is characterized in that it comprises deletions, substitutions and/or insertions wherein the deletions/insertions/substitutions are at positions 7, 13, 22, 33, 75, 165, 201, 221, 222, 259, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L71 W13R L22M Q33E K75N T165P A201T S221L I222K G259D S338P H462Y.

In another preferred embodiment, the variant according to the invention is characterized in that it comprises deletions, substitutions and/or insertions wherein the deletions/insertions/substitutions are at positions 7, 13, 22, 75, 165, 171, 201, 221, 222, 259, 338 and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L71 W13R L22M K75N T165P T171A A201T S221L I222K G259D S338P H462Y.

In another preferred embodiment, the variant according to the invention is characterized in that it comprises deletions, substitutions and/or insertions wherein the deletions/insertions/substitutions are at positions 7, 13, 22, 75, 165, 167, 171, 201, 221, 222, 259, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L71 W13R L22M K75N T165P N167A T171A A201T S221L I222K G259D H462Y.

In a further embodiment, the present invention relates to a variant of an HIV synthase showing an improved activity in converting acetone and a compound which provides an activated acetyl group characterized by the following formula (I):

into 3-hydroxyisovalerate (HIV) over the corresponding HIV synthase from which it is derived, wherein the HIV synthase is characterized in that it shows one or more substitutions, deletions and/or insertions in comparison to the corresponding sequence from which it is derived and wherein these substitutions, deletions and/or insertions occur at one or more of the positions corresponding to positions 7, 13, 22, 24, 33, 38, 41, 43, 54, 74, 75, 81, 165, 167, 171, 201, 221, 222, 226, 246, 259, 296, 325, 338, 345, 363, 394, 396, 457, 462, 473, 475, 480, 481, 486, 490, 491, 500, 514, 516, 519 and 520 296 in the amino acid shown in SEQ ID NO:1, wherein X is selected from the group consisting of S—CH2-CH2-NH—CO—CH2-CH2-NH—CO—CH(OH)—C(CH3)2-CH2-O—PO2H—O—PO2H—C10H13N5O7P (coenzyme A), S—CH2-CH2-NH—CO—CH2-CH2-NH—CO—CH(OH)—C(CH3)2-CH2-O—PO2H-polypeptide (acyl-carrier protein), S—CH2-CH2-NH—CO—CH2-CH2-NH—CO—CH(OH)—C(CH3)2-CH2-OH (pantetheine), S—$CH_2$—$CH_2$—NH—CO—$CH_3$ (N-acetyl-cysteamine), S—$CH_3$ (methane thiol), S—CH2-CH(NH2)-CO2H (cysteine), S—CH2-CH2-CH(NH2)-CO2H (homocysteine), S—CH2-CH(NH—C5H8NO3)-CO—NH—CH2-CO2H (glutathione), S—$CH_2$—$CH_2$—$SO_3H$ (coenzyme M) and OH (acetic acid). Preferably, X is coenzyme A.

In a preferred embodiment, the HMG CoA synthase from which the variant is derived is an HMG CoA synthase which shows the amino acid sequence shown in SEQ ID NO:1 or an amino acid sequence having at least 60% sequence identity to SEQ ID NO:1.

Accordingly, in one embodiment, the present invention relates to an HIV synthase variant having an amino acid sequence as shown in SEQ ID NO:1 or an amino acid sequence having at least 60% sequence identity to SEQ ID NO:1, in which one or more amino acid residues at a position selected from the group consisting of positions 7, 13, 22, 24, 33, 38, 41, 43, 54, 74, 75, 81, 165, 167, 171, 201, 221, 222, 226, 246, 259, 296, 325, 338, 345, 363, 394, 396, 457, 462, 473, 475, 480, 481, 486, 490, 491, 500, 514, 516, 519 and 520 in the amino acid sequence shown in SEQ ID NO:1 or at a position corresponding to any of these positions, are substituted with another amino acid residue or deleted or wherein an insertion has been effected at one or more of these positions and wherein said HIV synthase has an improved activity in converting acetone and a compound which provides an activated acetyl group characterized by the following formula (I):

into 3-hydroxyisovalerate (HIV) over the corresponding HIV synthase from which it is derived, wherein X is selected from the group consisting of S—CH2-CH2-NH—CO—CH2-CH2-NH—CO—CH(OH)—C(CH3)2-CH2-O—PO2H—O—PO2H—C10H13N5O7P (coenzyme A), S—CH2-CH2-NH—CO—CH2-CH2-NH—CO—CH(OH)—C(CH3)2-CH2-O—PO2H-polypeptide (acyl-carrier protein), S—CH2-CH2-NH—CO—CH2-CH2-NH—CO—CH(OH)—C(CH3)2-CH2-OH (pantetheine), S—$CH_2$—$CH_2$—NH—CO—$CH_3$ (N-acetyl-cysteamine), S—$CH_3$ (methane thiol), S—CH2-CH(NH2)-CO2H (cysteine), S—CH2-CH2-CH(NH2)-CO2H (homocysteine), S—CH2-CH(NH—C5H8NO3)-CO—NH—CH2-CO2H (glutathione), S—$CH_2$—$CH_2$—$SO_3H$ (coenzyme M) and OH (acetic acid). Preferably, X is coenzyme A.

The variants of an HIV synthase of the present invention are preferably characterized in that they show an increased activity in converting acetone into 3-hydroxyisovalerate when compared to the HIV synthase from which they are derived. Thus, in the case where the variant is derived from the HMG CoA synthase of *Mus musculus* the amino acid of which is shown in SEQ ID NO:1, the variant shows an increased activity in converting acetone when compared to the HMG CoA synthase having the amino acid sequence of SEQ ID NO:1. When the variant is derived from an HIV synthase which is structurally related to the HMG CoA synthase of *Mus musculus* as defined herein above, the variant shows an increased activity in converting acetone into 3-hydroxyisovalerate when compared to the corresponding starting sequence into which the corresponding mutations have been Introduced. In a particularly preferred embodiment such variants show also an increased activity in converting acetone into 3-hydroxyisovalerate when compared to the HMG CoA synthase of *Mus musculus* shown in SEQ ID NO: 1.

The activity of converting acetone into 3-hydroxyisovalerate (HIV) may be determined by methods known to the person skilled in the art. In one embodiment, this activity is determined as described in the Examples appended hereto. In a particular embodiment this activity can be measured by incubating the enzyme, preferably a cell lysate containing the overexpressed recombinant protein, in vitro. Alternatively, a purified enzyme can be used. More specifically, the enzyme whose activity is to be assessed may be produced as outlined in the following: The sequence coding for the wild type version or variants of the HIV synthase is subcloned in the pET25b+ expression vector (Novagen) using standard molecular biology techniques. The expression constructs are transformed into BL21(DE3) competent cells (Novagen). Isolated clones are used to inoculate 50 ml of auto-induction medium (Studier F. W, Protein Expr. Purif. 41 (2005), 207-234) supplemented with the appropriate antibiotic and grown overnight at 30° C. for 20-22 hours in a shaking incubator set at 700 rpm. The cells are pelleted and stored at −80° C. for at least overnight.

The enzymatic assay is set up using clarified cell lysate: the frozen cell pellets containing the overexpressed recombinant enzyme are resuspended in a lysis buffer (BugBuster, Merck Novagen). The cell suspension is incubated for 10 minutes at room temperature followed by 20 minutes on ice. Cell lysates are clarified by centrifugation and His6 tagged enzymes were purified from clarified lysates by affinity chromatography (Macherey Nagel). The purified enzymes are concentrated by centrifugation using ultrafiltration membranes (Amicon ultra, Millipore) and desalted by size exclusion chromatography (Zeba spin columns, Perbio Science). The amount of the enzyme variant present in the concentrated soluble fraction is estimated on SDS-PAGE gel against a BSA calibration curve using gel densitometry.

Purified enzymes are characterized in vitro in a coupled, multi-step enzymatic conversion of acetone and acetyl-CoA into IBN (IBN) via 3-hydroxyisovalerate (HIV) and 3-phosphonoxy-isovaleric acid (PIV) using the HIV synthase variants and controls to be assessed and purified HIV phosphorylase and PIV decarboxylase enzymes prepared. The nature of the "HIV phosphorylase" and the "PIV decarboxylase" used as well as their production and purification is described above. 40 μg of pure enzyme preparations are incubated in HIV/IBN production buffer (50 mM Tris, 10 mM MgCl2, 20 mM KCl, 0.5 mM DTT, 700 mM acetone, 4 mM acetyl-CoA, 5 mM ATP, 0.5 mM DTT, 5 μg HIV phosphorylase and 85 μg PIV decarboxylase) in 2 ml crimp top glass vials. Glass vials are sealed using crimp caps and incubated for 8 hours at 37° C. to allow enzymatic conversion of substrates into isobutene (IBN). Enzymatic reactions is finally stopped by heat shock denaturation of enzymes at 80° c. for 5 minutes.

Control reactions are set up using bacterial clones containing either the empty expression vector peT25b+ or the expression vector expressing the wild type enzyme.

IBN quantification (and directly proportional the activity of the HIV synthase): The isobutene (IBN) produced spontaneously volatilizes and can be quantified by gas chromatography (GC) analysis of reactions head space. Downstream enzymes (i.e. the HIV phosphorylase and PIV decarboxylase) being in excess, the quantity of isobutene (IBN) produced is directly proportional with the quantity of HIV produced and, therefore, correlates with HIV synthase activity and, accordingly, provides an indirect readout for the reaction of the conversion of acetone into 3-hydroxyisovalerate (HIV). The amount of isobutene produced is quantified by gas chromatography analysis. For the GC headspace analysis, 100 μl of headspace gases from each enzymatic reaction are injected (Injection parameters: 250° C.; split=10) in a Brucker GC-450 system equipped with a Flame ionization detector (FID) (250° C.; 28 $ml\cdot min^{-1}$ $H_2$; 30 $ml\cdot min^{-}$ N2; 300 $ml\cdot min^{-1}$ synthetic air)). Compounds present in samples are separated by chromatography using a RTX-1 column (15m x 0.32 mm; Restek, France) at 100° C. with a 1 $ml\cdot min^{-1}$ constant flow of carrier gaz (nitrogen 5.0, Messer, France). Upon injection, peak area of isobutene is calculated for samples and standards.

Alternatively to the above assay utilizing purified enzymes, the activity of the HIV synthase variant to be tested may also be assessed in a whole cell assay, i.e., in a cell suspension. This assay utilizes a bacterial strain transformed with an expression vector (Merck-Novagen peT25b (+)) containing the coding sequences in an expressible manner for the expression of the three enzymes involved in the metabolic pathway converting acetone into isobutene, i.e., a HIV synthase variant of the present invention capable of converting acetone into 3-hydroxyisovalerate, a HIV phosphorylase capable of converting 3-hydroxyisovalerate into PIV (3-phosphonoxy-isovaleric acid) and PIV decarboxylase capable of converting PIV Into isobutene). The nature of the "HIV phosphorylase" and the "PIV decarboxylase" used as well as their production and purification is described above. The sequences coding for the HIV synthase variants and, as a control, the wild-type HIV synthase, are cloned in the expression vector containing the HIV phosphorylase and PIV decarboxylase coding sequences using standard molecular biology techniques. The expression construct is transformed into BL21(D3) competent cells (Novagen) and the cells are plated and grown 24 hours at 30° C. on LB plates supplemented with the appropriate antibiotic. Isolated clones are used to inoculate 1 ml of LB culture medium and grown at 30° C. for 20 hours in a shaking incubator set at 700 rpm (58% humidity). These starter cultures are used to inoculate 1 ml of auto-induction medium (Studier F. W, Protein Expr. Purif. 41 (2005), 207-234) supplemented with the appropriate antibiotic and grown overnight at 30° C. for 24 hours in a shaking incubator set at 700 rpm. The cells are pelleted and the cell pellets containing the three overexpressed recombinant enzymes are resuspended in 500 μl of minimal medium supplemented with acetone and glucose (Potassium phosphate 200 mM, Citric acid 4 mM Ammonium chloride 20 mM, NTA mix 1×, glucose 45 g/l and acetone 500 mM; composition of NTA mix is: 10 mM $C_6HgNO_6Na_3$, 3 mM $CaCl_2$, 3 mM $Cl_3Fe$, 1 mM $Cl_2Mn$, 0.3 mM $Cl_2Zn$, 0.4 mM $BH_3O_3$, 0.3 mM $Cl_3Cr$, 0.3 mM $Cl_2Co$, 0.3 mM $Cl_2Cu$, 0.3 mM $Cl_2Ni$, 0.3 mM $Na_2MoO_4$, 0.3 mM $Na_2O_3Se$.). The enzymatic assay, i.e., the whole cell assay in cell suspension is incubated in sealed container at 37° C. for 2, 4, 6, 16, 20 and 24 hours in a shaking incubator. Isobutene (IBN) quantification is quantified by GC as described above.

In the context of the present invention an "increased activity" means that the activity of the HIV synthase variant in question is increased at least by a factor of 1.1, preferably at least by a factor of 2 and even more preferably at least by a factor of 24 or at least by a factor 100, 1000, 10000 or 10000 when compared to the enzyme from which it is derived, preferably when compared to the HMG CoA synthase of *Mus musculus* the amino acid of which is shown in SEQ ID NO:1.

According to one embodiment, the HIV synthase variant of the present invention has an amino acid sequence as shown in SEQ ID NO:1 in which (1) an amino acid residue at position 7 in the amino acid sequence shown in SEQ ID NO:1 or at a position corresponding to this position, is deleted or substituted with isoleucine or glycine; and/or (2) an amino acid residue at position 13 in the amino acid sequence shown in SEQ ID NO:1 or at a position corresponding to this position, is deleted or substituted with arginine or leucine; and/or (3) an amino acid residue at position 22 in the amino acid sequence shown in SEQ ID NO:1 or at a position corresponding to this position, is deleted or substituted with methionine; and/or (4) an amino acid residue at position 24 in the amino acid sequence shown in SEQ ID NO:1 or at a position corresponding to this position, is deleted or substituted with methionine; and/or (5) an amino acid residue at position 38 In the amino acid sequence shown in SEQ ID NO:1 or at a position corresponding to this position, is deleted or substituted with glycine; and/or (6) an amino acid residue at position 33 in the amino acid sequence shown in SEQ ID NO:1 or at a position corresponding to this position, is deleted or substituted with glutamic acid; and/or (7) an amino acid residue at position 41 in the amino acid sequence shown in SEQ ID NO:1 or at a position corresponding to this position, is deleted or substituted with serine; and/or (8) an amino acid residue at position 43 in the amino acid sequence shown in SEQ ID NO:1 or at a position corresponding to this position, is deleted or substituted with valine; and/or (9) an amino acid residue at position 54 in the amino acid sequence shown in SEQ ID NO:1 or at a position corresponding to this position, is deleted or substituted with glycine; and/or

(10) an amino acid residue at position 74 in the amino acid sequence shown in SEQ ID NO:1 or at a position corresponding to this position, is deleted or substituted with glutamic acid; and/or

(11) an amino acid residue at position 75 in the amino acid sequence shown in SEQ ID NO:1 or at a position corresponding to this position, is deleted or substituted with asparagine; and/or

(12) an amino acid residue at position 81 in the amino acid sequence shown in SEQ ID NO:1 or at a position corresponding to this position, is deleted or substituted with arginine; and/or

(13) an amino acid residue at position 165 in the amino acid sequence shown in SEQ ID NO:1 or at a position corresponding to this position, is deleted or substituted with proline and glutamine; and/or

(14) an amino acid residue at position 167 in the amino acid sequence shown in SEQ ID NO:1 or at a position corresponding to this position, is deleted or substituted with alanine; and/or

(15) an amino acid residue at position 171 in the amino acid sequence shown in SEQ ID NO:1 or at a position corresponding to this position, is deleted or substituted with alanine or glycine; and/or

(16) an amino acid residue at position 201 in the amino acid sequence shown in SEQ ID NO:1 or at a position corresponding to this position, is deleted or substituted with threonine; and/or

(17) an amino acid residue at position 221 in the amino acid sequence shown in SEQ ID NO:1 or at a position corresponding to this position, is deleted or substituted with leucine, valine, Isoleucine or threonine; and/or

(18) an amino acid residue at position 222 in the amino acid sequence shown in SEQ ID NO:1 or at a position corresponding to this position, is deleted or substituted with arginine, glutamine, lysine or histidine; and/or

(19) an amino acid residue at position 226 in the amino acid sequence shown in SEQ ID NO:1 or at a position corresponding to this position, is deleted or substituted with methionine; and/or

(20) an amino acid residue at position 246 in the amino acid sequence shown in SEQ ID NO:1 or at a position corresponding to this position, is deleted or substituted with arginine; and/or

(21) an amino acid residue at position 259 in the amino acid sequence shown in SEQ ID NO:1 or at a position corresponding to this position, is deleted or substituted with aspartic acid; and/or

(22) an amino acid residue at position 296 in the amino acid sequence shown in SEQ ID NO:1 or at a position corresponding to this position, is deleted or substituted with glutamine; and/or

(23) an amino acid residue at position 325 in the amino acid sequence shown in SEQ ID NO:1 or at a position corresponding to this position, is deleted or substituted with alanine, leucine or valine; and/or

(24) an amino acid residue at position 338 in the amino acid sequence shown in SEQ ID NO:1 or at a position corresponding to this position, is deleted or substituted with proline; and/or

(25) an amino acid residue at position 345 in the amino acid sequence shown in SEQ ID NO:1 or at a position corresponding to this position, is deleted or substituted with phenylalanine; and/or

(26) an amino acid residue at position 363 in the amino acid sequence shown in SEQ ID NO:1 or at a position corresponding to this position, is deleted or substituted with arginine; and/or

(27) an amino acid residue at position 394 in the amino acid sequence shown in SEQ ID NO:1 or at a position corresponding to this position, is deleted or substituted with serine; and/or

(28) an amino acid residue at position 396 in the amino acid sequence shown in SEQ ID NO:1 or at a position corresponding to this position, is deleted or substituted with asparagine; and/or

(29) an amino acid residue at position 457 in the amino acid sequence shown in SEQ ID NO:1 or at a position corresponding to this position, is deleted or substituted with cysteine; and/or

(30) an amino acid residue at position 462 in the amino acid sequence shown in SEQ ID NO:1 or at a position corresponding to this position, is deleted or substituted with tyrosine; and/or

(31) an amino acid residue at position 473 in the amino acid sequence shown in SEQ ID NO:1 or at a position corresponding to this position, is deleted or substituted with aspartic acid or glycine; and/or

(32) an amino acid residue at position 475 in the amino acid sequence shown in SEQ ID NO:1 or at a position corresponding to this position, is deleted or substituted with arginine; and/or

(33) an amino acid residue at position 480 in the amino acid sequence shown in SEQ ID NO:1 or at a position corresponding to this position, is deleted or substituted with cysteine; and/or

(34) an amino acid residue at position 481 in the amino acid sequence shown in SEQ ID NO:1 or at a position corresponding to this position, is deleted or substituted with serine; and/or

(35) an amino acid residue at position 486 in the amino acid sequence shown in SEQ ID NO:1 or at a position corresponding to this position, is deleted or substituted with arginine; and/or

(36) an amino acid residue at position 490 in the amino acid sequence shown in SEQ ID NO:1 or at a position corresponding to this position, is deleted or substituted with asparagine; and/or

(37) an amino acid residue at position 491 in the amino acid sequence shown in SEQ ID NO:1 or at a position corresponding to this position, is deleted or substituted with alanine; and/or

(38) an amino acid residue at position 500 in the amino acid sequence shown in SEQ ID NO:1 or at a position corresponding to this position, is deleted or substituted with serine; and/or

(39) an amino acid residue at position 514 in the amino acid sequence shown in SEQ ID NO:1 or at a position corresponding to this position, is deleted or substituted with arginine, glycine or serine; and/or

(40) an amino acid residue at position 516 in the amino acid sequence shown in SEQ ID NO:1 or at a position corresponding to this position, is deleted or substituted with asparagine; and/or
(41) an amino acid residue at position 519 in the amino acid sequence shown in SEQ ID NO:1 or at a position corresponding to this position, is deleted or substituted with aspartic acid; and/or
(42) an amino acid residue at position 520 in the amino acid sequence shown in SEQ ID NO:1 or at a position corresponding to this position, is deleted or substituted with serine.

The invention also relates to variants as defined in items (1) to (42) hereinabove, wherein the amino acid residue indicated as substituting the amino acid residue at the position in SEQ ID NO: 1 is not that particular amino acid residue but an amino acid residue which is conservative in relation to the indicated substituting amino acid.

Whether an amino acid is conservative with respect to another amino acid can be judged according to means and methods known in the art. One possibility is the PAM 250 matrix; alternatively, the Blosum Family Matrices can be used.

The present invention also relates to HIV synthase variants as described herein above which show an increased activity in converting acetone into HIV but which have lost the capacity of catalyzing the conversion of their natural substrate. As described above, an HIV synthase is preferably derived from an HMG CoA synthase. In such a case, it is possible to provide HIV synthases which are capable of catalyzing the conversion of acetone into HIV but which have lost the capacity to catalyze the conversion of acetyl-CoA and acetoacetyl-CoA into 3-hydroxy-3-methylglutaryl-CoA (HMG-CoA). Examples for such variants are provided in the appended Example section.

As mentioned above, it has been shown that HMG CoA synthases can act to produce HIV enzymatically from acetone and a compound which provides an activated acetyl group. Thus, the present invention provides improved variants of such "HIV synthase" enzymes defined above which are capable of converting acetone and a compound which provides an activated acetyl group into HIV.

Moreover, it has been shown that some of these variants also exhibit an improved selectivity for the enzymatic conversion of acetone and a compound which provides an activated acetyl group into HIV over the HMG CoA synthase's original activity in condensing acetyl-CoA with acetoacetyl-CoA to form 3-hydroxy-3-methylglutaryl-CoA (HMG-CoA).

Thus, the present invention also relates to improved variants of enzymes which are capable of converting acetone and a compound which provides an activated acetyl group into HIV having an improved selectivity.

In the context of the present invention, "Improved selectivity" means that the ratio of 3-hydroxyisovalerate synthase activity vs. HMG CoA synthase activity is higher than that of the enzyme represented by SEQ ID NO:1. In other words, the ratio of the activity of condensing acetone and a compound which provides an activated acetyl group to form 3-hydroxyisovalerate vs. the activity of condensing acetyl-CoA with acetoacetyl-CoA to form 3-hydroxy-3-methylglutaryl-CoA (HMG-CoA) is higher than that of the enzyme represented by SEQ ID NO:1. This ratio can be calculated by measuring the activities of the enzymes on both substrates, as shown, for example, in Example 7.

Methods to determine the activity for the condensation of acetone and a compound which provides an activated acetyl group into 3-hydroxyisovalerate (HIV synthase activity) and the activity of the condensation of acetyl-CoA with acetoacetyl-CoA to form 3-hydroxy-3-methylglutaryl-CoA (HMG-CoA) (HMG-CoA synthesis activity), respectively, have been described above.

Thus, an improved selectivity of a variant can be determined once the HIV synthase activity and the HMG-CoA synthesis activity have been determined. A ratio of the activities for the measured amount of 3-hydroxyisovalerate and HMG-CoA produced in a given time under defined conditions is then determined, and the ratio of the activities is compared with the corresponding ratio for the parent enzyme. Accordingly, a variant having an improved selectivity for the production of 3-hydroxyisovalerate over the production of HMG-CoA can be determined.

An Improved ratio can result from a different Km value for at least one of the two substrates. It can also result from a difference in the turnover number, e.g., a different kcat value for at least one of the two reactions. It can also result from a different kcat/Km value for at least one of the two reactions. In the context of the present invention, an "improved selectivity" means that the above ratio is at least 1,5-fold higher, preferably at least 2-fold higher, more preferably at least 5-fold higher, even more preferably at least 10-fold higher and particularly preferred at least 10-fold higher than the ratio of the enzyme from which the variant is derived, preferably higher than the ratio of the enzyme represented by SEQ ID NO:1.

Thus, the present invention relates to a variant of a 3-hydroxyisovalerate (HIV) synthase showing an improved selectivity in converting acetone and a compound which provides an activated acetyl group characterized by the following formula (I):

$$\begin{array}{c} H \\ / \\ H - C^2 - H \\ \backslash \\ C^1 = O \\ / \\ X \end{array}$$

into 3-hydroxyisovalerate over the corresponding HIV synthase from which it is derived, wherein X is selected from the group consisting of S—CH2-CH2-NH—CO—CH2-CH2-NH—CO—CH(OH)—C(CH3)2-CH2-O—PO2H—O—PO2H—C10H13N5O7P (coenzyme A), S—CH2-CH2-NH—CO—CH2-CH2-NH—CO—CH(OH)—C(CH3)2-CH2-O—PO2H-polypeptide (acyl-carrier protein), S—CH2-CH2-NH—CO—CH2-CH2-NH—CO—CH(OH)—C(CH3)2-CH2-OH (pantetheine), S—$CH_2$—$CH_2$—NH—CO—$CH_3$ (N-acetyl-cysteamine), S—$CH_3$ (methane thiol), S—CH2-CH(NH2)-CO2H (cysteine), S—CH2-CH2-CH(NH2)-CO2H (homocysteine), S—CH2-CH(NH—C5H8NO3)-CO—NH—CH2-CO2H (glutathione), S—$CH_2$—$CH_2$—$SO_3H$ (coenzyme M) and OH (acetic acid).

Moreover, the present invention relates to a variant of a 3-hydroxyisovalerate (HIV) synthase showing an improved selectivity in converting acetone and a compound which provides an activated acetyl group characterized by the following formula (I):

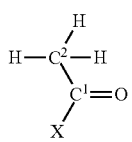

into 3-hydroxyisovalerate over the corresponding HIV synthase from which it is derived, wherein the HIV variant is characterized in that it shows one or more substitutions, deletions and/or insertions in comparison to the corresponding sequence from which it is derived and wherein these substitutions, deletions and/or insertions occur at one or more of the positions corresponding to positions 7, 13, 22, 75, 165, 201, 221, 222, 226, 246, 259, 296, 462, 473, 475, 480, 481 and 500 in the amino acid sequence shown in SEQ ID NO:1.

The present invention also relates to a HIV synthase variant of a variant of a 3-hydroxyisovalerate (HIV) synthase showing an improved selectivity in converting acetone and a compound which provides an activated acetyl group characterized by the following formula (I):

into 3-hydroxyisovalerate over the corresponding HIV synthase from which it is derived having an amino acid sequence as shown in SEQ ID NO:1 or an amino acid sequence having at least 60% sequence identity to SEQ ID NO:1, in which one or more amino acid residues at a position selected from the group consisting of positions 7, 13, 22, 75, 165, 201, 221, 222, 226, 246, 259, 296, 462, 473, 475, 480, 481 and 500 in the amino acid sequence shown in SEQ ID NO:1 or at a position corresponding to any of these positions, are substituted with another amino acid residue or deleted or wherein an insertion has been effected at one or more of these positions and wherein said HIV synthase has an improved selectivity in converting acetone and a compound which provides an activated acetyl group characterized by the following formula (I):

into 3-hydroxyisovalerate (HIV) over the corresponding HIV synthase from which it is derived, wherein X is selected from the group consisting of S—CH2-CH2-NH—CO—CH2-CH2-NH—CO—CH(OH)—C(CH3)2-CH2-O—PO2H—O—PO2H—C10H13N5O7P (coenzyme A), S—CH2-CH2-NH—CO—CH2-CH2-NH—CO—CH(OH)—C(CH3)2-CH2-O—PO2H-polypeptide (acyl-carrier protein), S—CH2-CH2-NH—CO—CH2-CH2-NH—CO—CH(OH)—C(CH3)2-CH2-OH (pantetheine), S—$CH_2$—$CH_2$—NH—CO—$CH_3$ (N-acetyl-cysteamine), S—$CH_3$ (methane thiol), S—CH2-CH(NH2)-CO2H (cysteine), S—CH2-CH2-CH(NH2)-CO2H (homocysteine), S—CH2-CH(NH—C5H8NO3)-CO—NH—CH2-CO2H (glutathione), S—CH2-$CH_2$—$SO_3H$ (coenzyme M) and OH (acetic acid). As regards the determination of the sequence identity, the same applies as has been set forth above.

According to one embodiment, the HIV synthase variant having an improved selectivity in converting acetone and a compound which provides an activated acetyl group characterized by the following formula (I):

into 3-hydroxyisovalerate over the corresponding HIV synthase from which it derived has an amino acid sequence as shown in SEQ ID NO:1 in which:

(1) an amino acid residue at position 7 in the amino acid sequence shown in SEQ ID NO:1 or at a position corresponding to this position, is deleted or substituted with isoleucine; and/or (2) an amino acid residue at position 13 in the amino acid sequence shown in SEQ ID NO:1 or at a position corresponding to this position, is deleted or substituted with arginine or leucine; and/or (3) an amino acid residue at position 22 in the amino acid sequence shown in SEQ ID NO:1 or at a position corresponding to this position, is deleted or substituted with methionine; and/or (4) an amino acid residue at position 75 in the amino acid sequence shown in SEQ ID NO:1 or at a position corresponding to this position, is deleted or substituted with asparagine; and/or (5) an amino acid residue at position 165 in the amino acid sequence shown in SEQ ID NO:1 or at a position corresponding to this position, is deleted or substituted with proline and glutamine; and/or (6) an amino acid residue at position 201 in the amino acid sequence shown in SEQ ID NO:1 or at a position corresponding to this position, is deleted or substituted with threonine; and/or (7) an amino acid residue at position 221 in the amino acid sequence shown in SEQ ID NO:1 or at a position corresponding to this position, is deleted or substituted with leucine; and/or (8) an amino acid residue at position 222 in the amino acid sequence shown in SEQ ID NO:1 or at a position corresponding to this position, is deleted or substituted with glutamine, lysine or histidine; and/or (9) an amino acid residue at position 226 in the amino acid sequence shown in SEQ ID NO:1 or at a position corresponding to this position, is deleted or substituted with methionine; and/or

(10) an amino acid residue at position 246 in the amino acid sequence shown in SEQ ID NO:1 or at a position corresponding to this position, is deleted or substituted with arginine; and/or

(11) an amino acid residue at position 259 in the amino acid sequence shown in SEQ ID NO:1 or at a position corresponding to this position, is deleted or substituted with aspartic acid; and/or

(12) an amino acid residue at position 296 in the amino acid sequence shown in SEQ ID NO:1 or at a position corresponding to this position, is deleted or substituted with glutamine; and/or

(13) an amino acid residue at position 462 in the amino acid sequence shown in SEQ ID NO:1 or at a position corresponding to this position, is deleted or substituted with tyrosine; and/or

(14) an amino acid residue at position 473 in the amino acid sequence shown in SEQ ID NO:1 or at a position corresponding to this position, is deleted or substituted with aspartic acid or glycine; and/or

(15) an amino acid residue at position 475 In the amino acid sequence shown in SEQ ID NO:1 or at a position corresponding to this position, is deleted or substituted with arginine; and/or

(16) an amino acid residue at position 480 in the amino acid sequence shown in SEQ ID NO:1 or at a position corresponding to this position, is deleted or substituted with cysteine; and/or

(17) an amino acid residue at position 481 in the amino acid sequence shown in SEQ ID NO:1 or at a position corresponding to this position, is deleted or substituted with serine; and/or

(18) an amino acid residue at position 500 in the amino acid sequence shown in SEQ ID NO:1 or at a position corresponding to this position, is deleted or substituted with serine; and/or The invention also relates to variants as defined in items (1) to (18) hereinabove, wherein the amino acid residue indicated as substituting the amino acid residue at the position in SEQ ID NO: 1 is not that particular amino acid residue but an amino acid residue which is conservative in relation to the indicated substituting amino acid as already described above.

In preferred embodiments, the variant according to the invention showing an improved selectivity in converting acetone and a compound which provides an activated acetyl group into 3-hydroxyisovalerate (HIV) is characterized in that it has multiple mutations. As it is exemplified in the examples further below, variants have been found bearing multiple mutations which exhibit an increase in the selectivity for the conversion of acetone into 3-hydroxyisovalerate (HIV). These variants bearing multiple mutations are summarized in the following. Accordingly, in a very preferred embodiment, the variant according to the invention is characterized in that it comprises deletions, substitutions and/or insertions wherein the deletions/insertions/substitutions are at positions 22, 201 and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T H462Y.

In another preferred embodiment, the variant according to the invention is characterized in that it comprises deletions, substitutions and/or insertions wherein the deletions/insertions/substitutions are at positions 22, 201, 221, 259 and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T S221L G259D H462Y.

In another preferred embodiment, the variant according to the invention is characterized in that it comprises deletions, substitutions and/or insertions wherein the deletions/insertions/substitutions are at positions 22, 165, 201, 221, 222, 259 and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M T165P A201T S221L I222Q G259D H462Y.

In another preferred embodiment, the variant according to the invention is characterized in that it comprises deletions, substitutions and/or insertions wherein the deletions/insertions/substitutions are at positions 22, 75, 165, 201, 221, 222, 259, 296, 462, 473 and 481 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165P A201T S221L I222K G259D S296Q H462Y N473G M481S.

In another preferred embodiment, the variant according to the invention is characterized in that it comprises deletions, substitutions and/or insertions wherein the deletions/insertions/substitutions are at positions 22, 201, 221, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T S221L H462Y.

In another preferred embodiment, the variant according to the invention is characterized in that it comprises deletions, substitutions and/or insertions wherein the deletions/insertions/substitutions are at positions 22, 165, 201, 221, 222, 226, 246, 259, 296, 462, 473, 475 and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M T165Q A201T S221L I222K L226M K246R G259D S296Q H462Y N473D H475R V500S.

In another preferred embodiment, the variant according to the invention is characterized in that it comprises deletions, substitutions and/or insertions wherein the deletions/insertions/substitutions are at positions 22, 75, 165, 201, 221, 222, 259, 296, 462 and 475 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165Q A201T S221L I222Q G259D S296Q H462Y H475R.

In another preferred embodiment, the variant according to the invention is characterized in that it comprises deletions, substitutions and/or insertions wherein the deletions/insertions/substitutions are at positions 22, 201, 221, 222 and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T S221L I222K H462Y.

In another preferred embodiment, the variant according to the invention is characterized in that it comprises deletions, substitutions and/or insertions wherein the deletions/insertions/substitutions are at positions 22, 75, 165, 201, 221, 222, 296, 462, 473, 475 and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165P A201T S221L I222K S296Q H462Y N473D H475R V500S.

In another preferred embodiment, the variant according to the invention is characterized in that it comprises deletions, substitutions and/or insertions wherein the deletions/insertions/substitutions are at positions 22, 201, 221, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T S221L H462Y.

In another preferred embodiment, the variant according to the invention is characterized in that it comprises deletions, substitutions and/or insertions wherein the deletions/insertions/substitutions are at positions 22, 75, 165, 201, 221, 222, 259, 296, 462 and 475 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165Q A201T S221L I222Q G259D S296Q H462Y H475R.

In another preferred embodiment, the variant according to the invention is characterized in that it comprises deletions, substitutions and/or insertions wherein the deletions/insertions/substitutions are at positions 22, 75, 165, 201, 221, 222, 296, 462, 473, 475 and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165P A201T S221L I222K S296Q H462Y N473D H475R V500S.

In another preferred embodiment, the variant according to the invention is characterized in that it comprises deletions, substitutions and/or insertions wherein the deletions/insertions/substitutions are at positions 22, 75, 165, 201, 221, 222, 259, 296, 462, 473, and 481 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165P A201T S221L I222K G259D S296Q H462Y N473G M481S.

In another preferred embodiment, the variant according to the invention is characterized in that it comprises deletions, substitutions and/or insertions wherein the deletions/insertions/substitutions are at positions 22, 75, 165, 201, 221, 222, 226, 246, 259, 462, 473 and 480 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M K75N T165P A201T S221L I222H L226M K246R G259D H462Y N473D G480C.

In another preferred embodiment, the variant according to the invention is characterized in that it comprises deletions, substitutions and/or insertions wherein the deletions/insertions/substitutions are at positions 22, 165, 201, 221, 222, 226, 246, 259, 296, 462, 473, 475 and 500 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M T165Q A201T S221L I222K L226M K246R G259D S296Q H462Y N473D H475R V500S.

In another preferred embodiment, the variant according to the invention is characterized in that it comprises deletions, substitutions and/or insertions wherein the deletions/insertions/substitutions are at positions 22, 201, 221, 462 and 222 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L22M A201T S221L H462Y I222K.

In another preferred embodiment, the variant according to the invention is characterized in that it comprises deletions, substitutions and/or insertions wherein the deletions/insertions/substitutions are at positions 7, 13, 22, 75, 165, 201, 221, 222, 259, and 462 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

L7I W13R L22M K75N T165P A201T S221L I222K G259D H462Y.

The present invention also relates to a method for providing a variant of an HIV synthase wherein said variant shows an improved activity of converting acetone into 3-hydroxyisovalerate, said method comprising the step of effecting one or more changes in the sequence of an HMG CoA synthase wherein said change(s) is/are effected at one or more amino acid positions selected from the group consisting of the amino acid positions corresponding to positions 7, 13, 22, 24, 33, 38, 41, 43, 54, 74, 75, 81, 100, 165, 167, 171, 201, 221, 222, 226, 246, 259, 270, 296, 325, 338, 345, 363, 394, 396, 457, 462, 473, 475, 480, 481, 486, 490, 491, 500, 514, 516, 519 and 520 in the amino acid sequence shown in SEQ ID NO:1.

As regards the preferred embodiments of an HMG CoA synthase to be mutated according to such a method, the same applies as has been set forth herein-above. In one preferred embodiment the HMG CoA synthase from which the variant is derived is an HMG CoA synthase which shows the amino acid sequence as shown in SEQ ID NO: 1 or an amino acid sequence having at least 60% sequence identity to SEQ ID NO:1 or any of the preferred degrees of sequence identity as specified herein-above.

Moreover, as regards preferred embodiments of the degree of improvement in activity and the changes to be effected, the same applies as described herein-above.

In particular, the present invention more preferably relates to such a method wherein the changes which are effected in an HMG CoA synthase at one or more positions corresponding to positions corresponding to positions 7, 13, 22, 24, 33, 38, 41, 43, 54, 74, 75, 81, 100, 165, 167, 171, 201, 221, 222, 226, 246, 259, 270, 296, 325, 338, 345, 363, 394, 396, 457, 462, 473, 475, 480, 481, 486, 490, 491, 500, 514, 516, 519 and 520 in the amino acid sequence shown in SEQ ID NO:1 are selected from the group consisting of those identified in items (1) to (40) as described above in the context of the variants having an improved activity.

The present invention also relates to a method for providing a variant of an HIV synthase wherein said variant shows an improved selectivity of converting acetone into 3-hydroxyisovalerate, said method comprising the step of effecting one or more changes in the sequence of an HMG CoA synthase wherein said change(s) is/are effected at one or more amino acid positions selected from the group consisting of the amino acid positions corresponding to positions 7, 13, 22, 75, 165, 201, 221, 222, 226, 246, 259, 296, 462, 473, 475, 480, 481 and 500 in the amino acid sequence shown in SEQ ID NO:1.

Moreover, as regards preferred embodiments of the degree of improvement in activity and the changes to be effected, the same applies as described herein-above.

In particular, the present invention more preferably relates to such a method wherein the changes which are effected in an HMG CoA synthase at one or more positions corresponding to positions corresponding to positions 7, 13, 22, 75, 165, 201, 221, 222, 226, 246, 259, 296, 462, 473, 475, 480, 481 and 500 in the amino acid sequence shown in SEQ ID NO:1 are selected from the group consisting of those identified in items (1) to (18) as described above in the context of the variants having an improved selectivity.

In a further embodiment, the present invention relates to a nucleic acid molecule encoding the HIV synthase variant of the invention. Moreover, the present invention relates in a further embodiment to a vector comprising said nucleic acid. Further, in yet another embodiment, the present invention relates to a host cell comprising said vector. The embodiments relating to the nucleic acid, the vector and the host cell of the present invention are further described in the following in more detail.

An HIV synthase of the present invention can be fused to a homologous or heterologous polypeptide or protein, an enzyme, a substrate or a tag to form a fusion protein. Fusion proteins in accordance with the present invention will have the same improved activity as the HIV synthase of the present invention. Polypeptides, enzymes, substrates or tags that can be added to another protein are known in the art. They may useful for purifying or detecting the proteins of the invention. For instance, tags that can be used for detection and/or purification are e.g. FLAG-tag, His6-tag or a Strep-tag. Alternatively, the protein of the invention can be fused to an enzyme e.g. luciferase, for the detection or localisation of said protein. Other fusion partners include, but are not limited to, bacterial β-galactosidase, trpE, Protein A, β-lactamase, alpha amylase, alcohol dehydrogenase or yeast alpha mating factor. It is also conceivable that the polypeptide, enzyme, substrate or tag is removed from the protein of the invention after e.g. purification. Fusion proteins can typically be made by either recombinant nucleic acid methods or by synthetic polypeptide methods known in art.

The present invention further relates to a nucleic acid molecule encoding an HIV synthase of the present invention and to a vector comprising said nucleic acid molecules. Vectors that can be used in accordance with the present invention are known in the art. The vectors can further comprise expression control sequences operably linked to the nucleic acid molecules of the present invention contained in the vectors. These expression control sequences may be suited to ensure transcription and synthesis of a translatable RNA in bacteria or fungi. Expression control sequences can for instance be promoters. Promoters for use in connection with the nucleic acid molecules of the present invention may be homologous or heterologous with regard to its origin and/or with regard to the gene to be expressed. Suitable promoters are for instance promoters which lend themselves to constitutive expression. However, promoters which are only activated at a point in time determined by external influences can also be used. Artificial and/or chemically inducible promoters may be used in this context.

Preferably, the vector of the present invention is an expression vector. Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence. The DNA sequence naturally controlling the transcription of the corresponding gene can be used as the promoter sequence, if it is active in the selected host organism. However, this sequence can also be exchanged for other promoter sequences. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance E. coli, S. cerevisiae) are sufficiently described in the literature. Promoters permitting a particularly high expression of a downstream sequence are for instance the T7 promoter (Studier et al., Methods in Enzymology 185 (1990), 60-89), lacUV5, trp, trp-lacUV5 (DeBoer et al., in Rodriguez and Chamberlin (Eds), Promoters, Structure and Function; Praeger, N.Y., (1982), 462-481; DeBoer et al., Proc. Natl. Acad. Sci. USA (1983), 21-25), Ip1, rac (Boros et al., Gene 42 (1986), 97-100). Inducible promoters are preferably used for the synthesis of polypeptides. These promoters often lead to higher polypeptide yields than do constitutive promoters. In order to obtain an optimum amount of polypeptide, a two-stage process is often used. First, the host cells are cultured under optimum conditions up to a relatively high cell density. In the second step, transcription is induced depending on the type of promoter used. In this regard, a tac promoter is particularly suitable which can be induced by lactose or IPTG (=isopropyl-β-D-thiogalactopyranoside) (deBoer et al., Proc. Natl. Acad. Sci. USA 80 (1983), 21-25). Termination signals for transcription are also described in the literature.

In addition, the present invention relates to a host cell comprising the vector of the present invention.

In a preferred embodiment, the host cell according to the presenting invention is a microorganism, in particular a bacterium or a fungus. In a more preferred embodiment, the host cell of the present invention is E. coli, a bacterium of the genus Clostridium or a yeast cell, such as S. cerevisiae. In another preferred embodiment the host cell is a plant cell or a non-human animal cell.

The transformation of the host cell with a vector according to the invention can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990. The host cell is cultured in nutrient media meeting the requirements of the particular host cell used, in particular in respect of the pH value, temperature, salt concentration, aeration, antibiotics, vitamins, trace elements etc.

As mentioned above, whenever reference is made to a "HIV phosphorylase" and a "PIV decarboxylase" (the latter is alternatively also referred to as "IBN synthetase") reference is made to enzymes which are capable of catalyzing the conversion of 3-hydroxyisovalerate (HIV) into 3-phosphonoxy-isovaleric acid (PIV) as defined further below and to enzymes which are capable of catalyzing the conversion of 3-phosphonoxy-isovaleric acid (PIV) into isobutene (IBN) as defined further below, respectively.

The present invention also relates to the use of an HIV synthase variant of the present invention as described above or of a host cell comprising such an HIV synthase variant for the conversion of acetone as described above into 3-hydroxyisovalerate.

Thus, the present invention relates to the use of the HIV synthase variant of the present invention or the host cell of the present invention for the conversion of acetone and a compound which provides an activated acetyl group characterized by the following formula (I):

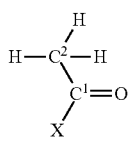

into 3-hydroxyisovalerate (HIV), wherein X is selected from the group consisting of S—CH2-CH2-NH—CO—CH2-CH2-NH—CO—CH(OH)—C(CH3)2-CH2-O—PO2H—O—PO2H—C10H13N5O7P (coenzyme A), S—CH2-CH2-NH—CO—CH2-CH2-NH—CO—CH(OH)—C(CH3)2-CH2-O—PO2H-polypeptide (acyl-carrier protein), S—CH2-CH2-NH—CO—CH2-CH2-NH—CO—CH(OH)—C(CH3)2-CH2-OH (pantetheine), S—CH$_2$—CH$_2$—NH—CO—CH$_3$ (N-acetyl-cysteamine), S—CH$_3$ (methane thiol), S—CH2-CH(NH2)-CO2H (cysteine), S—CH2-CH2-CH(NH2)-CO2H (homocysteine), S—CH2-CH(NH—C5H8NO3)-CO—NH—CH2-CO2H (glutathione), S—CH$_2$—CH$_2$—SO$_3$H (coenzyme M) and OH (acetic acid). Preferably. In the above use, X is S—CH2-CH2-NH—CO—CH2-CH2-NH—CO—CH(OH)—C(CH3)2-CH2-O—PO2H—O—PO2H—C10H13N5O7P (coenzyme A). Preferably, X is coenzyme A.

As described above, a HIV variant of the present invention is capable of converting acetone into HIV while HIV may only be an intermediate for the production of isobutene.

Accordingly, the present invention also relates to a method for the production of 3-hydroxyisovalerate (HIV), comprising the step of converting acetone into 3-hydroxyisovalerate by making use of an HIV synthase of the invention as defined above. Such a method is preferably carried out by making use of a host cell as defined above which expresses an HIV synthase of the present invention.

The method according to the present invention may be carried out in vitro or in vivo. An in vitro reaction is understood to be a reaction in which no cells are employed, i.e. an acellular reaction.

For carrying out the method in vitro the substrates for the reaction and the enzyme/enzymes are incubated under conditions (buffer, temperature, cofactors etc.) allowing the enzyme/enzymes to be active and the enzymatic conversion to occur. The reaction is allowed to proceed for a time sufficient to produce 3-hydroxyisovalerate (HIV).

The enzyme/enzymes may be in any suitable form allowing the enzymatic reaction to take place. It/they may be purified or partially purified or in the form of crude cellular extracts or partially purified extracts. It is also possible that the enzyme/enzymes is immobilized on a suitable carrier.

For carrying out the method in vivo use is made of a suitable organism/microorganism(s) which express an HIV synthase variant of the present invention as defined above.

Thus, in the case of this embodiment the method according to the invention is characterised in that the conversion of acetone and a compound which provides an activated acetyl group is realized in the presence of an organism expressing an HIV synthase variant of the present invention.

The substrates, i.e., acetone and a compound which provides an activated acetyl group as defined above, preferably coenzyme A, can be provided externally or can be produced by the organism itself. In one preferred embodiment, the organism is at least capable of producing a compound providing an activated acetyl group, preferably coenzyme A. In such a case, acetone is externally, e.g., by adding it to the culture medium. In a preferred embodiment, the organism expressing an HIV synthase variant according to the present invention is capable of producing acetone. The term "which is capable of producing acetone" in the context of the present invention means that the organism/microorganism has the capacity to produce acetone within the cell due to the presence of enzymes providing enzymatic activities allowing the production of acetone from metabolic precursors.

Acetone is produced by certain microorganisms, such as *Clostridium acetobutylicum*, *Clostridium beijerinckii*, *Clostridium cellulolyticum*, *Bacillus polymyxa* and *Pseudomonas putida*. The synthesis of acetone is best characterized in *Clostridium acetobutylicum*. It starts out with a reaction (reaction step 1) in which two molecules of acetyl-CoA are condensed into acetoacetyl-CoA. This reaction is catalyzed by acetyl-CoA acetyltransferase (EC 2.3.1.9). Acetoacetyl-CoA is then converted into acetoacetate by a reaction with acetic acid or butyric acid resulting also in the production of acetyl-CoA or butyryl-CoA (reaction step 2). This reaction is catalyzed e.g. by acetoacetylCoA transferase (EC 2.8.3.8). AcetoacetylCoA transferase is known from various organisms, e.g. from *E. coli* in which it is encoded by the atoAD gene or from *Clostridium acetobutylicum* in which it is encoded by the ctfAB gene. However, also other enzymes can catalyze this reaction, e.g. 3-oxoacid CoA transferase (EC 2.8.3.5) or succinate CoA ligase (EC 6.2.1.5).

Finally, acetoacetate is converted into acetone by a decarboxylation step (reaction step 3 catalyzed by acetoacetate decarboxylase (EC 4.1.1.4).

The above described reaction steps 1 and 2 and the enzymes catalyzing them are not characteristic for the acetone synthesis and can be found in various organism. In contrast, reaction step 3 which is catalyzed by acetoacetate decarboxylase (EC 4.1.1.4) is only found in those organisms which are capable of producing acetone.

In one preferred embodiment, the organism according to the present invention which can be employed in the method according to the Invention is an organism, preferably a microorganism, which naturally has the capacity to produce acetone.

Thus, preferably the microorganism belongs to the genus *Clostridium*, *Bacillus* or *Pseudomonas*, more preferably to the species *Clostridium acetobutylicum*, *Clostridium beijerinckii*, *Clostridium cellulolyticum*, *Bacillus polymyxa* or *Pseudomonas putida*.

In such an embodiment, the organism according to the invention is an organism, preferably a microorganism, which naturally has the capacity to produce acetone and which is recombinant in the sense that it has further been genetically modified so as to express an HIV synthase according to the present invention. Thus, the term "recombinant" means that the organism is genetically modified so as to contain a foreign nucleic acid molecule encoding an HIV synthase variant enzyme of the present invention as defined above. The term "foreign" in this context means that the nucleic acid molecule does not naturally occur in said organism/microorganism. This means that it does not occur in the same structure or at the same location in the organism/microorganism. In one preferred embodiment, the foreign nucleic acid molecule is a recombinant molecule comprising a promoter and a coding sequence encoding the HIV synthase variant, in which the promoter driving expression of the coding sequence is heterologous with respect to the coding sequence. Heterologous in this context means that the promoter is not the promoter naturally driving the expression of said coding sequence but is a promoter naturally driving expression of a different coding sequence, i.e., it is derived from another gene, or is a synthetic promoter or a chimeric promoter. Preferably, the promoter is a promoter heterologous to the organism/microorganism, i.e. a promoter which does not naturally occur in the respective organism/microorganism. Even more preferably, the promoter is an inducible promoter. Promoters for driving expression in different types of organisms, in particular in microorganisms, are well known to the person skilled in the art.

In another preferred embodiment the nucleic acid molecule is foreign to the organism/microorganism in that the encoded HIV synthase variant, is/are not endogenous to the organism/microorganism, i.e. are naturally not expressed by the organism/microorganism when it is not genetically modified.

The term "recombinant" in another embodiment means that the organism is genetically modified in the regulatory region controlling the expression of an enzyme as defined above which naturally occurs in the organism so as to lead to an increase in expression of the respective enzyme in comparison to a corresponding non-genetically modified organism.

Such a modification of a regulatory region can be achieved by methods known to the person skilled in the art. One example is to exchange the naturally occurring promoter by a promoter which allows for a higher expression or to modify the naturally occurring promoter so as to show a higher expression. Thus, in this embodiment the organism contains in the regulatory region of the gene encoding an enzyme as defined above a foreign nucleic acid molecule which naturally does not occur in the organism and which leads to a higher expression of the enzyme in comparison to a corresponding non-genetically modified organism.

The foreign nucleic acid molecule may be present in the organism/microorganism in extrachromosomal form, e.g. as plasmid, or stably integrated in the chromosome. A stable integration is preferred.

In another preferred embodiment, the organism according to the invention is a genetically modified organism, preferably a microorganism, derived from an organism/microorganism which naturally does not produce acetone but which has been genetically modified so as to produce acetone, i.e. by introducing the gene(s) necessary for allowing the production of acetone in the organism/microorganism. In principle any microorganism can be genetically modified in this way. The enzymes responsible for the synthesis of acetone have been described above. Genes encoding corresponding enzymes are known in the art and can be used to genetically modify a given microorganism so as to produce acetone. As described above, the reaction steps 1 and 2 of the acetone synthesis occur naturally in most organisms. However, reaction step 3 is characteristic and crucial for acetone synthesis. Thus, in a preferred embodiment, a genetically modified organism/microorganism derived from an organism/microorganism which naturally does not produce acetone is modified so as to contain a nucleotide sequence encoding an enzyme catalyzing the conversion of acetoacetate into acetone by decarboxylation, e.g. an acetoacetate decarboxylase (EC 4.1.1.4). Nucleotide sequences from several organisms encoding this enzyme are known in the art, e.g. the adc gene from *Clostridium acetobutylicum* (Uniprot accession numbers P23670 and P23673), *Clostridium beijerinckii* (*Clostridium* MP; Q9RPK1), *Clostridium pasteurianum* (Uniprot accession number P81336), *Bradyrhizobium* sp. (strain BTAi1/ATCC BAA-1182; Uniprot accession number A5EBU7), *Burkholderia mallei* (ATCC 10399 A9LBS0), *Burkholderia mallei* (Uniprot accession number A3MAE3), *Burkholderia mallei* FMH A5XJB2, *Burkholderia cenocepacia* (Uniprot accession number A0B471), *Burkholderia ambifaria* (Uniprot accession number Q0b5P1), *Burkholderia phytofirmans* (Uniprot accession number B2T319), *Burkholderia* sp. (Uniprot accession number Q38ZU0), *Clostridium botulinum* (Uniprot accession number B2TLN8), *Ralstonia pickettii* (Uniprot accession number B2UIG7), *Streptomyces nogalater* (Uniprot accession number Q9EYI7), *Streptomyces avermitills* (Uniprot accession number Q82NF4), *Legionella pneumophila* (Uniprot accession number Q5ZXQ9), *Lactobacillus salivarius* (Uniprot accession number QIWVG5), *Rhodococcus* spec. (Uniprot accession number QOS7W4), *Lactobacillus plantarum, Rhizobium leguminosarum* (Uniprot accession number Q1M911), *Lactobacillus casei* (Uniprot accession number Q03B66), *Saccharopolyspora erythreae* (Uniprot accession number A4FKR9), *Korarchaeum cryptofilum* (Uniprot accession number B1L3N6), *Bacillus amyloliquefaciens* (Uniprot accession number A7Z8K8), *Cochliobolus heterostrophus* (Uniprot accession number Q8NJQ3), *Sulfolobus islandicus* (Uniprot accession number C3ML22) and *Francisella tularensis* subsp. *holarctica* (strain QOBLC9).

More preferably, the organism, preferably microorganism, is genetically modified so as to be transformed with a nucleic acid molecule encoding an enzyme capable of catalyzing the above mentioned reaction step 2 of the acetone synthesis, i.e. the conversion of acetoacetyl CoA into acetoacetate.

Even more preferably, the organism, preferably microorganism, is genetically modified so as to be transformed with a nucleic acid molecule encoding an enzyme capable of catalyzing the above mentioned reaction step 1 of the acetone synthesis, i.e. the condensation of two molecules of acetyl CoA into acetoacetatyl CoA.

In a particularly preferred embodiment the organism/microorganism is genetically modified so as to be transformed with a nucleic acid molecule encoding an enzyme capable of catalyzing the above mentioned reaction step 1 of the acetone synthesis and with a nucleic acid molecule encoding an enzyme capable of catalyzing the above mentioned reaction step 2 of the acetone synthesis or with a nucleic acid molecule encoding an enzyme capable of catalyzing the above mentioned reaction step 1 of the acetone synthesis and with a nucleic acid molecule encoding an enzyme capable of catalyzing the above mentioned reaction step 3 of the acetone synthesis or with a nucleic acid molecule encoding an enzyme capable of catalyzing the above mentioned reaction step 2 of the acetone synthesis and with a nucleic acid molecule encoding an enzyme capable of catalyzing the above mentioned reaction step 3 of the acetone synthesis or with a nucleic acid molecule encoding an enzyme capable of catalyzing the above mentioned reaction step 1 of the acetone synthesis and with a nucleic acid molecule encoding an enzyme capable of catalyzing the above mentioned reaction step 2 of the acetone synthesis and with a nucleic acid molecule encoding an enzyme capable of catalyzing the above mentioned reaction step 3 of the acetone synthesis.

Methods for preparing the above mentioned genetically modified organism, preferably microorganisms, are well known in the art. Thus, generally, the organism/microorganism is transformed with a DNA construct allowing expression of the respective enzyme in the microorganism. Such a construct normally comprises the coding sequence in question linked to regulatory sequences allowing transcription and translation in the respective host cell, e.g. a promoter and/enhancer and/or transcription terminator and/or ribosome binding sites etc. The prior art already describes microorganisms which have been genetically modified so as to be able to produce acetone. In particular genes from, e.g., *Clostridium acetobutylicum* have been introduced into *E. coli* thereby allowing the synthesis of acetone in *E. coli*, a bacterium which naturally does not produce acetone (Bermejo et al., Appl. Environ. Microbiol. 64 (1998); 1079-1085; Hanai et al., Appl. Environ. Microbiol. 73 (2007), 7814-7818). In particular Hanai et al. (loc. cit.) shows that it is sufficient to introduce a nucleic acid sequence encoding an acetoacetate decarboxylase (such as that from *Clostridium acetobutylicum*) in order to achieve acetone production in *E. coli* indicating that the endogenous enzymes in *E. coli* catalyzing the above-mentioned reaction steps 1 and 2 (i.e. the expression products of the *E. coli* atoB and atoAD genes) are sufficient to provide substrate for the acetone production.

Moreover, in accordance with the foregoing, the present invention relates to a method for producing isobutene from acetone comprising a method for the production of 3-hydroxyisovalerate (HIV), comprising the step of converting acetone into 3-hydroxyisovalerate by making use of an HIV synthase variant of the invention as defined above, wherein this method is preferably carried out by making use of a host cell as defined above which expresses an HIV synthase of the present invention, and further comprising the step of converting the produced 3-hydroxyisovalerate into isobutene.

Accordingly, the above described use of the HIV synthase variant of the present invention or the host cell of the present invention for the conversion of acetone into 3-hydroxyisovalerate (HIV) as well as the method for the production of 3-hydroxyisovalerate (HIV) comprising the step of converting acetone into 3-hydroxyisovalerate by making use of an HIV synthase of the present invention may be supplemented with subsequent steps utilizing corresponding enzymes in order to produce isobutene since, as described above, HIV may only be an intermediate for the production of isobutene.

Thus, as outlined above, in the claimed use and method, the produced HIV can subsequently further be converted into isobutene via an enzymatically catalyzed phosphorylation/decarboxylation reaction (as it is, e.g., described in WO 2010/001078 and WO 2012/052427) via 3-phosphonoxy-isovalerate (PIV). More specifically, the synthesis of isobutene (IBN) is achieved by first enzymatically converting acetone and a compound which provides an activated acetyl group into 3-hydroxyisovalerate (HIV) in line with the above utilizing a HIV synthase variant of the present invention and then further converting the intermediate HIV into isobutene. The latter reaction comprises two steps, i.e., the activation of HIV with ATP to form 3-phosphonoxy-isovaleric acid (also referred to as PIV or 3-methyl-3-phosphonoxy-butyric acid) which is, e.g., achieved by an enzymatically catalysed phosphorylation reaction as described in WO 2012/052427, and the subsequent conversion of PIV into isobutene (also referred to as IBN) is, e.g., achieved by an enzymatically catalyzed decarboxylation reaction as described, e.g., in WO 2010/001078 and WO 2012/052427. Enzymes which can be used for said conversion of HIV into isobutene are in particular mevalonate diphosphoate decarboxylases.

The claimed method and use according to the present invention comprising the subsequent steps of converting HIV (via PIV) into isobutene may be carried out in vitro or in vivo. An in vitro reaction is understood to be a reaction in which no cells are employed, i.e. an acellular reaction. For carrying out the method in vitro the substrates for the reaction and the below further described enzyme/enzymes (in addition to the HIV synthase variant of the present invention) are incubated under conditions (buffer, temperature, cofactors etc.) allowing the enzyme/enzymes to be active and the enzymatic conversion to occur. The reaction is allowed to proceed for a time sufficient to produce isobutene (IBN). The enzyme/enzymes may be in any suitable form allowing the enzymatic reaction to take place. It/they may be purified or partially purified or in the form of crude cellular extracts or partially purified extracts. It is also possible that the enzyme/enzymes is immobilized on a suitable carrier. Thus, the method according to the invention can be carried out in vitro, e.g. in the presence of isolated enzyme or of cell lysates comprising the enzyme or partially purified enzyme preparations comprising the HIV synthase variant of the present invention and, optionally, enzymes that are required for desired subsequent reactions. In vitro preferably means in a cell-free system.

Enzymes which can catalyze the desired subsequent reactions, i.e. the conversion of the 3-hydroxyisovalerate (HIV) into 3-phosphonoxy-isovaleric acid (PIV) PIV and/or for the conversion of PIV into isobutene (IBN), are described in the prior art and include, e.g., the enzymes described in WO 2010/001078 and WO 2012/052427. Preferably, enzyme(s) for the conversion of the 3-hydroxyisovalerate (HIV) into 3-phosphonoxy-isovaleric acid (PIV) PIV and/or for the conversion of PIV into isobutene (IBN) is/are mevalonate diphosphate decarboxylase.

In one embodiment, the enzyme employed in the in vitro use or in the method is used in purified form. However, such a method may be costly, since enzyme and substrate production and purification costs are high. Thus, in another preferred embodiment, the enzymes employed in the in vitro use or in the method are present in the reaction as a non-purified extract, or else in the form of non-lysed bacteria, so as to economize on protein purification costs. In an in vitro reaction the enzymes, native or recombinant, purified or not, are incubated in the presence of the substrate in physicochemical conditions allowing the enzymes to be active, and the incubation is allowed to proceed for a sufficient period of time allowing production of the desired product as described above. At the end of the incubation, one optionally measures the presence of the desired compound by using any detection system known to one of skill in the art such as gas chromatography or colorimetric tests for measuring the formation such compounds. In a particularly preferred embodiment of the invention the method is carried out in vitro and the enzyme is immobilized. Means and methods for immobilizing enzymes on different supports are well-known to the person skilled in the art.

For carrying out the above use or method for producing isobutene in vivo, use is made of a suitable organism/microorganism(s) which is/are capable of expressing a HIV synthase variant of the present invention as defined above and which is, optionally, also capable of producing acetone and/or a compound which provides an activated acyl group.

Accordingly, in a preferred embodiment, the present invention relates to methods and uses for producing isobutene utilizing a host cell of the present invention wherein such a host cell is a recombinant organism in the sense that it is genetically modified due to the introduction of at least one nucleic acid molecule encoding an HIV variant as described above wherein such an organism also expresses an enzyme capable of converting HIV into isobutene as described herein above, preferably a mevalonate diphosphate decarboxylase. In a preferred embodiment, the host cell is genetically modified by the introduction of at least one nucleic acid encoding (an) enzyme(s) which (is) are required for the conversion of the 3-hydroxyisovalerate (HIV) into 3-phosphonoxy-isovaleric acid (PIV) PIV and/or for the conversion of PIV into isobutene (IBN), preferably a mevalonate diphosphate decarboxylase. Preferably, such a nucleic acid molecule is heterologous with regard to the organism which means that it does not naturally occur in said host cell.

Thus, in another preferred embodiment the method according to the invention is carried out in culture, in the presence of an organism, preferably a microorganism, producing an enzyme variant of the present invention as well as the enzyme(s) which (is) are required for desired subsequent reactions, i.e., for the conversion of the 3-hydroxyisovalerate (HIV) into 3-phosphonoxy-isovaleric acid (PIV) PIV and/or for the conversion of PIV into isobutene (IBN). Thus, in such an embodiment of the invention, an organism, preferably a microorganism, that produces an enzyme of the present invention and (an) enzyme(s) which (is) are required for desired subsequent reactions, i.e., for the conversion of the 3-hydroxyisovalerate (HIV) into 3-phosphonoxy-isovaleric acid (PIV) PIV and/or for the conversion of PIV into isobutene (IBN) is used. In a preferred embodiment, the (micro)organism is recombinant in that the enzymes produced by the host are heterologous relative to the production host. The method or use can thus be carried out directly in the culture medium, without the need to separate or purify the enzymes. In an especially advantageous manner, a (micro)organism is used having the natural or artificial property of endogenously producing acetone, so as to produce the product directly from the substrate already present in the culture in solution.

In connection with the above described methods and uses, the organisms/microorganisms are cultivated under suitable culture conditions allowing the occurrence of the enzymatic reaction of the HIV synthase variants of the present invention and the subsequent conversion of HIV into isobutene. The specific culture conditions depend on the specific microorganism employed but are well known to the person skilled in the art. The culture conditions are generally chosen in such a manner that they allow the expression of the genes encoding the HIV synthases of the present invention and the enzyme(s) which (is) are required for the conversion of the 3-hydroxyisovalerate (HIV) into 3-phosphonoxy-isovaleric acid (PIV) and/or for the conversion of PIV into isobutene (IBN). Various methods are known to the person skilled in the art in order to improve and fine-tune the expression of certain genes at certain stages of the culture such as induction of gene expression by chemical inducers or by a temperature shift.

The method according to the invention furthermore comprises the step of collecting gaseous products, e.g. isobutene, degassing out of the reaction, i.e. recovering the products which degas, e.g., out of the culture. Thus in a preferred embodiment, the method is carried out in the presence of a system for collecting isobutene and acetone under gaseous form during the reaction while isobutene is separated from acetone which may also be part of the gaseous phase.

As a matter of fact, short alkenes such as isobutene adopt the gaseous state at room temperature and atmospheric pressure. Moreover, isoprene also adopts the gaseous state under culture conditions at 37° C. The method according to the invention therefore does not require extraction of the product from the liquid culture medium, a step which is always very costly when performed at industrial scale. The evacuation and storage of the gaseous hydrocarbons and their possible subsequent physical separation and chemical conversion can be performed according to any method known to one of skill in the art.

Other aspects and advantages of the invention will be described in the following examples, which are given for purposes of illustration and not by way of limitation.

FIG. 1: Isobutene metabolic pathway. The "HIV phosphorylase" and "IBN synthetase" (herein, the latter is also termed "PIV decarboxylase") referred to in FIG. 1 refers to enzymes which are capable of catalyzing the conversion of 3-hydroxyisovalerate (HIV) into 3-phosphonoxy-isovaleric acid (PIV) as defined above and to enzymes which are capable of catalyzing the conversion of 3-phosphonoxy-isovaleric acid (PIV) into isobutene (IBN) as defined above, respectively.

FIG. 2: Schematic representation of a directed evolution approach.

FIG. 3: Sample results from the primary screen of the directed evolution approach of Hmg-CoA synthase with respect to HIV production by screening in vitro.

FIG. 4.: Relative activity of 4 variants identified displaying increased activity over the WT HIV synthase activity.

FIG. 5: Analysis of mutants harbouring 1 to 4 recombined mutations.

FIG. 6: Sample results from the primary screen of the directed evolution approach of Hmg-CoA synthase with respect to HIV production by screening in vitro.

FIG. 7: Results of in vivo screening of an HIV synthase variants library. Relative activity is expressed as an IBN peak array from twelve replicates for one given mutant over the mean IBN peak area from twelve replicates for the template sequence.

FIG. 8: Relative activity of mutant variants having mutations at position 221 with respect to the production of HIV.

FIG. 9: Determination of kinetic constants for HIV synthases: indicated is the IBN peak area for wild type HIV synthase of SEQ ID NO:1 versus the IBN peak area of mutants [L22M; A201T; H462Y] and [L22M; A201T; S221L; H462Y] assayed for the production of HIV using acetone and acetyl-CoA as a substrate in a combined enzymatic test.

FIG. 10: Results from variants exhibiting a acetate-production-reducing/HIV-production-improving mutation.

FIG. 11: Characterization of HIV synthase variants in a whole cell assay demonstrating that all three variants tested produce an increased amount of isobutene compared to the wild type enzyme.

Other aspects and advantages of the invention will be described in the following examples, which are given for purposes of illustration and not by way of limitation.

EXAMPLES

General Outline of the Screening for HIV Synthase Variants Showing Improved Activity in Converting Acetone and a Compound which Provides an Activated Acetyl Group into HIV

Figure 2:
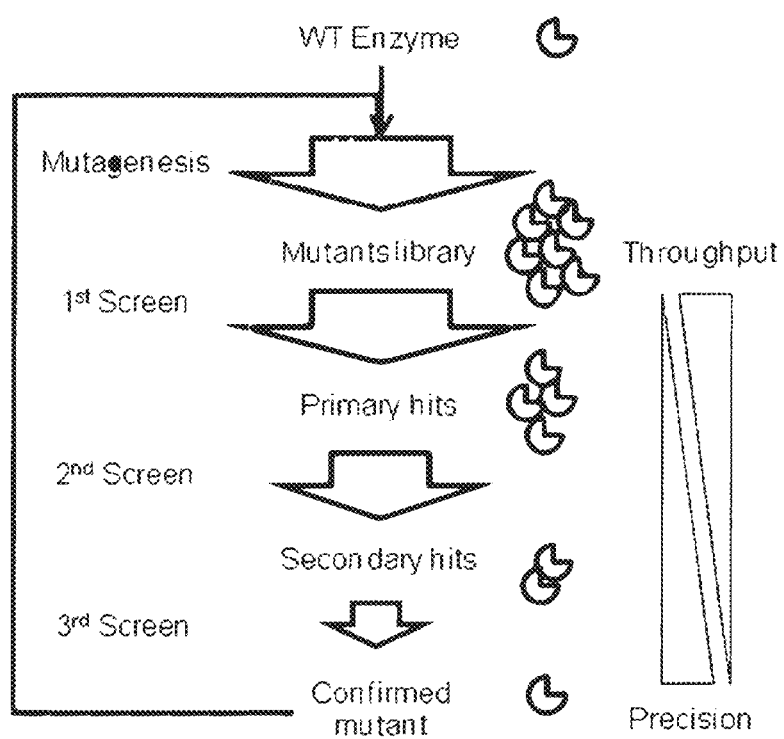

The screening was based on a directed evolution approach which consisted in (1) the generation of a DNA library coding for single or multiple point mutants of the HMG CoA synthase enzyme, (2) the design and validation of an assay to test the activity of these enzyme variants, (3) the use of the activity assay to screen the collection of mutants in order to identify mutants with improved activity compared to the wild type HMG CoA synthase. A schematic diagram of this approach is presented in FIG. 2. The screening method consists generally of several steps (up to 4) in order to eliminate false negatives or assay artefacts amongst the initial positive hits and thus allows to only retain true leads.

The screening aimed at identifying enzyme variants with higher rates of conversion of acetone into 3-hydroxyisovalerate (HIV).

A list summarizing the mutations identified which exhibit higher rates of conversion of acetone into 3-hydroxyisovalerate (HIV) is provided in the following Table 6.

TABLE 6

| WT sequence | Position | Improving mutations |
|---|---|---|
| L | 7 | I; G |
| W | 13 | L; R |
| L | 22 | M |
| I | 24 | M |
| Q | 33 | E |
| K | 38 | G |
| G | 41 | S |
| D | 43 | V |
| A | 54 | G |
| Q | 74 | E |
| K | 75 | N |
| S | 81 | R |
| K | 100 | L |
| T | 165 | P; Q |
| N | 167 | A |
| T | 171 | A; G |
| A | 201 | T |
| S | 221 | L; V; I; T |

TABLE 6-continued

| WT sequence | Position | Improving mutations |
|---|---|---|
| I | 222 | Q; K; H; R |
| L | 226 | M |
| K | 246 | R |
| G | 259 | D |
| L | 270 | I; M |
| S | 296 | Q |
| E | 325 | A; L: V |
| S | 338 | P |
| Y | 345 | F |
| Q | 363 | R |
| P | 394 | S |
| S | 396 | N |
| R | 457 | C |
| H | 462 | Y |
| N | 473 | G; D |
| H | 475 | R |
| G | 480 | C |
| M | 481 | S |
| S | 486 | R |
| T | 490 | N |
| E | 491 | A |
| V | 500 | S |
| V | 514 | G; S; R |
| S | 516 | N |
| E | 519 | D |
| H | 520 | S |

Moreover, variants obtained from the above described screening experiments bearing one or more mutations that confer increased HIV synthesis activity compared to the wild type sequence SEQ ID NO:1 are described in the following Table 7 where they have been organized according to their range of activities. Indicated in Table 7 is the mean relative activity, i.e., the ratio of Gas chromatography signal obtained for the mutant enzyme over Gas chromatography signal obtained for wild type enzyme. The fold increase was determined for one acetone concentration (125 mM or 700 mM in vitro and 500 mM in vivo). The enzyme quantity was normalized for in vitro measurements using purified enzymes but not for in vivo experiments.

TABLE 7

| Sequence | Mean relative Activity | Screening Assay |
|---|---|---|
| L22M T165P A201T S221L I222Q G259D S296Q H462Y M481S V500S S516N | 34.90 | IN VIVO |
| T165P I222Q S296Q M481S V500S S516N | 34.90 | IN VIVO |
| L22M T165P A201T S221L I222Q G259D S296Q H462Y N473G T490N | 34.20 | IN VIVO |
| L22M T165P A201T S221L I222Q G259D S296Q H462Y V500S | 33.82 | IN VIVO |
| T165P I222Q S296Q V500S | 33.81 | IN VIVO |
| L22M T165P A201T S221L I222Q G259D S296Q H462Y N473G M481S V500S | 33.04 | IN VIVO |
| T165P I222Q S296Q N473G M481S V500S | 33.04 | IN VIVO |
| L22M K75N T165Q A201T S221L I222Q G259D S296Q H462Y H475R | 31.54 | IN VIVO |
| L22M I24M K75N K100L T165P A201T S221L I222Q L226M K246R G259D L270I H462Y N473D G480C V500S | 31.15 | IN VIVO |
| L22M T165P A201T S221L I222Q G259D S296Q H462Y N473G V500S | 31.10 | IN VIVO |
| T165P I222Q S296Q N473G V500S | 31.10 | IN VIVO |
| L22M D43V T165P A201T S221L I222Q G259D H462Y M481S V500S | 30.56 | IN VIVO |
| D43V T165P I222Q M481S V500S | 30.55 | IN VIVO |
| L22M D43V S81R T165P A201T S221L I222Q G259D S296Q H462Y V500S V514S | 30.48 | IN VIVO |
| L22M K75N T165Q A201T S221L I222Q L226M G259D L270M S296Q H462Y N473D G480C V500S | 29.47 | IN VIVO |

TABLE 7-continued

| Sequence | Mean relative Activity | Screening Assay |
|---|---|---|
| L22M I24M T165P A201T S221L I222K L226M G259D L270M S296Q H462Y H475R | 29.42 | IN VIVO |
| L22M K75N T165P A201T S221L I222K G259D S296Q H462Y N473G M481S | 29.37 | IN VIVO |
| L22M D43V T165P A201T S221L I222Q G259D S296Q P394S R457C H462Y M481S V500S V514S | 27.69 | IN VIVO |
| D43V T165P I222Q S296Q P394S R457C M481S V500S V514S | 27.69 | IN VIVO |
| L22M K75N T165P A201T S221L I222H L226M K246R G259D H462Y N473D G480C | 27.36 | IN VIVO |
| L22M T165P A201T S221L I222Q G259D H462Y | 27.00 | IN VIVO |
| L22M T165P A201T S221L I222Q G259D S296Q S396N H462Y | 26.91 | IN VIVO |
| T165P I222Q S296Q S396N | 26.91 | IN VIVO |
| L22M K75N A201T S221L I222H G259D S296Q H462Y N473G G480C V500S | 26.65 | IN VIVO |
| L22M K75N T165P A201T S221L I222K S296Q H462Y N473D H475R V500S | 26.49 | IN VIVO |
| I222Q S296Q Y345F Q363R N473G M481S V500S V514S | 26.21 | IN VIVO |
| L22M A201T S221L I222Q G259D S296Q Y345F Q363R H462Y N473G M481S V500S V514S | 26.21 | IN VIVO |
| L22M D43V T165P A201T S221L I222Q G259D S296Q H462Y M481S V514S | 26.06 | IN VIVO |
| D43V T165P I222Q S296Q M481S V514S | 26.06 | IN VIVO |
| L22M A201T S221L I222Q G259D S296Q H462Y N473G M481S | 25.75 | IN VIVO |
| I222Q S296Q N473G M481S | 25.75 | IN VIVO |
| L22M A201T S221L I222Q G259D S296Q H462Y S486R | 25.52 | IN VIVO |
|

TABLE 7-continued

| Sequence | Mean relative Activity | Screening Assay |
|---|---|---|
| L22M K75N T165P A201T S221L I222Q G259D L270I S296Q H462Y H475R V500S | 18.77 | IN VIVO |
| L22M I24M K75N K100L T165P A201T S221L I222H L226M K246R G259D L270M S296Q H462Y N473D H475R | 18.19 | IN VIVO |
| L22M I24M K75N A201T S221L I222H G259D L270I S296Q H462Y H475R | 18.17 | IN VIVO |
| L22M I24M K75N K100L T165P A201T S221L I222K L226M K246R G259D L270M H462Y N473D V500S | 18.13 | IN VIVO |
| L22M I24M K75N T165Q A201T S221L L226M K246R G259D L270I S296Q H462Y H475R V500S V514S | 17.87 | IN VIVO |
| L22M K75N T165Q A201T S221L I222Q G259D S296Q H462Y H475R | 17.84 | IN VIVO |
| L22M I24M K75N T165Q A201T S221L I222K L226M G259D H462Y N473G | 17.69 | IN VIVO |
| L22M K75N T165P A201T S221L I222K S296Q H462Y N473D H475R V500S | 17.45 | IN VIVO |
| L22M I24M K75N T165Q A201T S221L I222Q L226M K246R G259D L270M S296Q H462Y N473D G480C | 17.38 | IN VIVO |
| L22M K75N A201T S221L G259D S296Q H462Y N473G G480C | 17.20 | IN VIVO |
| L22M K75N T165P A201T S221L I222K G259D S296Q H462Y N473G M481S | 17.06 | IN VIVO |
| L22M I24M K75N T165P A201T S221L I222K L226M K246R L270M S296Q H462Y N473G G480C M481S V500S | 16.99 | IN VIVO |
| L22M K75N T165Q A201T S221L I222H K246R G259D L270I S296Q H462Y N473G G480C M481S | 16.93 | IN VIVO |
| L22M I24M K75N T165Q A201T S221L I222R K246R G259D H462Y N473D G480C V500S E519D | 16.62 | IN VIVO |
| L22M K75N T165P A201T S221L I222H L226M K246R G259D H462Y N473D G480C | 15.60 | IN VIVO |
| L22M T165Q A201T S221L I222K L226M K246R G259D S296Q H462Y N473D H475R V500S | 15.55 | IN VIVO |
| L22M A201T S221L G259D H462Y | 15.51 | IN VIVO |
| L22M I24M K75N T165P A201T S221L I222K L226M S296Q H462Y | 15.49 | IN VIVO |
| L22M I24M K75N K100L T165P A201T S221L I222H K246R G259D L270M H462Y N473G G480C V500S | 15.36 | IN VIVO |
| L22M K75N T165Q A201T S221L H462Y | 15.05 | IN VIVO |
| L22M I24M K75N T165Q A201T S221L I222Q K246R G259D L270M H462Y N473G V514S | 14.73 | IN VIVO |
| L22M I24M K75N K100L T165P A201T S221L I222K K246R G259D L270M S296Q H462Y N473G M481S | 14.71 | IN VIVO |
| L22M A201T S221L I222Q H462Y | 14.57 | IN VIVO |
| L22M K75N T165Q A201T S221L L226M G259D L270I H462Y N473D V500S | 14.42 | IN VIVO |
| L22M K75N A201T S221L I222Q L226M K246R S296Q H462Y G480C V500S | 13.93 | IN VIVO |
| L22M I24M A201T S221L I222Q H462Y | 13.74 | IN VIVO |
| L22M A201T S221L I222K H462Y | 13.54 | IN VIVO |
| L22M I24M K75N T165Q A201T S221L I222H L226M L270M H462Y H475R | 12.90 | IN VIVO |
| L22M I24M K75N T165Q A201T S221L I222Q L226M K246R G259D L270M S296Q H462Y H475R V500S | 12.54 | IN VIVO |
| L22M I24M K75N T165Q A201T S221L L226M K246R G259D S296Q H462Y G480C V500S | 12.50 | IN VIVO |
| L22M K75N T165P A201T S221L I222K L226M K246R G259D L270M H462Y N473D H475R | 11.71 | IN VIVO |
| L22M I24M K75N A201T S221L I222H L270M S296Q H462Y V500S | 11.70 | IN VIVO |
| L22M A201T S221L I222H H462Y | 11.48 | IN VIVO |
| L22M A201T S221L H462Y V500S | 11.14 | IN VIVO |
| L22M A201T S221L S296Q H462Y | 11.06 | IN VIVO |
| L22M A201T S221L H462Y E491A | 10.11 | IN VIVO |
| L22M A201T S221L H462Y H475R | 9.68 | IN VIVO |
| L22M A201T S221L L226M H462Y | 9.43 | IN VIVO |
| L22M A201T S221L H462Y | 8.57 | IN VIVO |
| L22M A201T L270I H462Y | 3.72 | IN VITRO |
| L22M A201T L270M H462Y | 3.31 | IN VITRO |
| L22M K100L A201T H462Y | 2.81 | IN VITRO |
| L22M A201T K246R H462Y | 2.76 | IN VITRO |
| L22M A201T H462Y H520S | 2.74 | IN VITRO |
| L22M A201T H462Y E519D | 2.61 | IN VITRO |
| L22M A201T E325A H462Y | 2.50 | IN VITRO |
| L22M G41S A201T H462Y | 2.47 | IN VITRO |

TABLE 7-continued

| Sequence | Mean relative Activity | Screening Assay |
|---|---|---|
| L22M H462Y | 2.30 | IN VITRO |
| L22M H462Y E519D | 2.23 | IN VITRO |
| L22M A201T E519D | 2.07 | IN VITRO |
| L22M A201T H462Y | 2.04 | IN VITRO |
| L22M A201T | 1.91 | IN VITRO |
| A201T H462Y E519D | 1.87 | IN VITRO |
| L22M E519D | 1.66 | IN VITRO |
| H462Y E519D | 1.53 | IN VITRO |
| H462Y | 1.40 | IN VITRO |
| A201T | 1.28 | IN VITRO |
| L22M | 1.24 | IN VITRO |
| E519D | 1.19 | IN VITRO |
| A201T H462Y | 1.12 | IN VITRO |
| A201T E519D | 1.03 | IN VITRO |

I. Example 1: Directed Evolution of Hmg-CoA Synthase for HIV Production by in Vitro Screening 1. Library Construction A cDNA library coding for single residue mutants of HIV synthase was constructed using standard mutagenesis techniques. The full length coding sequence of the *Mus musculus* HIV synthase enzyme with N-term His6 tag was subcloned into commercial peT-25b+ expression vector and used as a template for the mutagenic PCR. The quality control of the library construction consisted of two steps: (1) the amplified DNA fragments obtained were analyzed and quantified against a range of control reactions and (2) DNA sequencing was carried out on 200 randomly-selected clones. The profiles of the DNA fragments were as expected.

2. Screening Assay

Plasmid DNA generated as described above and plasmid DNA containing the sequence coding for the *Mus musculus* wild type HIV synthase were transformed into BL21(DE3) competent cells and plated out onto LB-agar plates supplemented with the appropriate antibiotic. Cells were grown overnight at 30° C. until individual colonies reach the desired size.

Colonies were then picked and individually transferred into 1 mL of liquid LB medium supplemented with the appropriate antibiotic. Cell growth is carried out with agitation for 20 hours at 30° C. LB cultures were used to inoculate 1 ml of autoinduction medium (ZYM medium, Studier F. W; Protein Expr. Purif. 41 (2005), 207-234) supplemented with the appropriate antibiotic. Cultures were grown overnight at 30° C. for 20-22 hours in shacking incubator set at 700 rpm and 85% humidity. Cells were finally pelleted and stored at −80° C. overnight.

Frozen cell pellets were thawed on ice and resuspended in 200 μl Bugbuster (Merck Novagen) and incubated for 10 minutes at room temperature followed by 20 minutes on ice to allow cell lysis to proceed. Raw lysates were then clarified by centrifugation.

In parallel, 96 wells purification plates (Macherey Nagel) were prepared as follows. Purification matrices are wetted and equilibrated with 500 μl of wash buffer (10 mM Tris, 300 mM NaCl, 10 mM Imidazole, pH7.5). Clarified lysates (200 μl) were then transferred onto purification columns and allowed to flow through by gravity. Columns were washed with 1.2 ml of wash buffer and 200 μl of elution buffer (50 mM Tris, 250 mM Imidazole pH7.5). Elution of purified enzyme variants was finally performed with 110 μl of elution buffer.

After purification enzyme preparations were desalted using Zeba Spin Desalting plates (Perbio Sciences). Plates were centrifuged to remove storage buffer (1000 g, 2 min, 19C). Enzyme preparations from the previous step were transferred onto desalting resin and collected as effluent by centrifugation (100 g, 5 minutes, 19° C.). Thus prepared enzyme variants were then ready for use in the screening assay.

Screening assay consist in the in vitro coupled enzymatic conversion of acetone and acetyl-CoA into isobutene (IBN) via 3-hydroxyisovalerate (HIV) and 3-phosphonoxy-isovaleric acid (PIV) using the HIV synthase variant to be screened and purified HIV phosphorylase and PV decarboxylase enzymes prepared. As an "HIV phosphorylase", i.e., an enzyme capable of catalyzing the conversion of the 3-hydroxyisovalerate (HIV) into 3-phosphonoxy-isovaleric acid (PIV), a mevalonate diphosphate decarboxylase (EC 4.1.1.33) isolated from Thermoplasma *acidophilum* may be used (Uniprot entry for the wildtype sequence Q9H1N1-THEAC) having an amino acid substitution at position 200 (L200E) including a N terminal His6-tag wherein the HIV phosphorylase has the amino acid sequence as shown in SEQ ID NO:2. As an "PIV decarboxylase", i.e., an enzyme capable of catalyzing the conversion of PIV into isobutene (IBN), a mevalonate diphosphate decarboxylase (EC 4.1.1.33) isolated from *Streptococcus mitis* strain B6 may be used (Uniprot entry for the wildtype sequence D3HAT7-STRM6) having amino acid substitutions at positions 24, 118, 121, 159, 173, 177, 282, 291, and 297 (K24R C118L Y121R E159L M173C E177C K282C E291D F297L) including a N terminal His6-tag wherein the PIV decarboxylase has the amino acid sequence as shown in SEQ ID NO:3. The HIP phosphorylase and PIV decarboxylase may be produced as follows: the coding sequences of both the above described genes are sub-cloned into peT25b(+) (Merck-Novagen) and the resulting expression vectors are transformed into BL21(DE3) according to standard procedures. Single transformants are used to inoculate 1 liter of ZYM-5052 autodinduction medium (Studier F W, Prot. Exp. Pur. 41, (2005), 207-234). Cells are grown in a shaking incubator for 20-22 hours at 30° C. for the above *S. mitis* MDP and 8 hours at 37° C. followed by a 16 hours incubation at 28° C. for the above *T. acidophilum* MDP. Cells are pelleted and stored at −80° C. until further processed. For the cell lysis, cells pellets are resuspended in 40 ml of Bugbuster reagent (Merck-Novagen) supplemented with 100 μl of lysonase 10 minutes at room temperature followed by a further 20-minutes incubation at 4° C. Cell lysates are clarified by centrifugation (30-40 minutes at 10,000 g) and filtered through at 0.22 µm filter. Purification of the N-term His-tagged proteins of Interest from these cell lysates is carried out by IMAC (Immobilized Metal ion Affinity Chromatography) on a 5 ml HisTrap HP column using a ÄKTA Purifier UPC 100 (GE Healthcare) according to the manufacturer's recommendations. The eluted proteins are concentrated and desalted by ultrafiltration using Millipore Amicon Ultra-15 concentrated.

70 µl of enzymes preparations were mixed with 30 µl of reaction buffer (final concentrations in reaction are as follows: 50 mM Tris, 10 mM MgCl2, 20 mM KCl, 4 mM Ac-CoA, 125 mM acetone, 5 mM ATP, 0.5 mM DTT, 5 µg HIV phosphorylase and 85 µg PIV decarboxylase as produced and purified as described above) in 2 ml crimp top glass vials. Glass vials were sealed using crimp caps and incubated for 8 hours at 37° C. to allow enzymatic conversion of substrates into isobutene (IBN) to proceed. Enzymatic reactions were finally stopped by heat shock denaturation of enzymes at 80° c. for 5 minutes.

The isobutene (IBN) produced spontaneously volatilizes and can be quantified by gas chromatography (GC) analysis of reactions head space. Downstream enzymes (i.e. the HIV phosphorylase and PIV decarboxylase as produced and purified as described above) being in excess, the quantity of isobutene (IBN) produced is directly proportional with the quantity of HIV produced and therefore correlates with HIV synthase activity. It provides an indirect readout for the reaction of interest.

For GC headspace analysis, 100 µl of headspace gases from each enzymatic reaction were injected (Injection parameters: 250° C.; split=10) in a Brucker GC-450 system equipped with a Flame ionization detector (FID) (250° C.; 28 ml·min$^{-1}$ H$_2$; 30 ml·min$^{-1}$ N$_2$; 300 ml·min$^{-1}$ synthetic air). Compounds present in samples were separated by chromatography using a RTX-1 column (15m x 0.32 mm; Restek, France) at 100° C. with a 1 ml·min$^{-1}$ constant flow of carrier gaz (nitrogen 5.0, Messer, France). Upon injection, peak area of isobutene was calculated for samples and standards.

Figure 3:
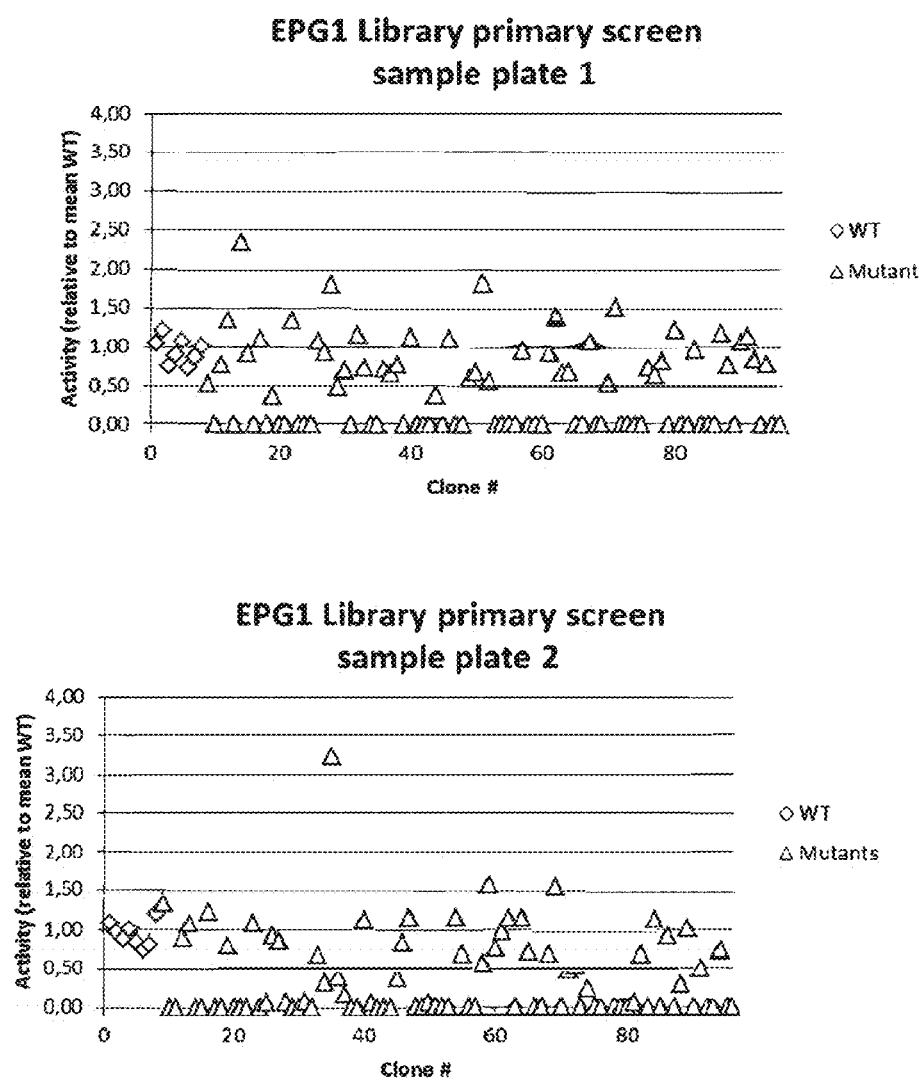

Variants displaying improved activity over that of parental enzyme were identified based on increased IBN peak area as quantified by GC. An example of results as obtained from the primary screen is presented in FIG. 3.

3. Identification of Enzyme Variants with Increased Activity

Figure 4:
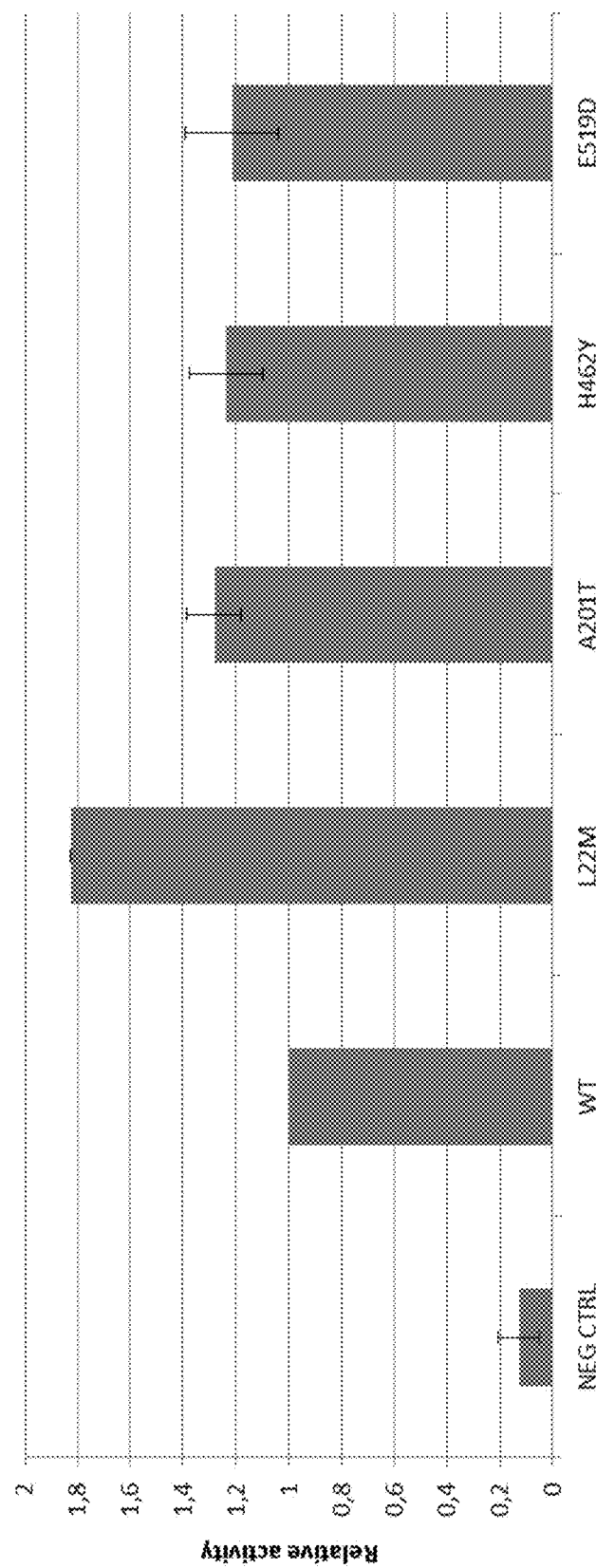

Of the initial HIV synthase variants library 7,392 variants were assayed as described above. Alongside the HIV synthase variants, control reactions were setup including reference controls using wild type HIV synthase enzyme. Altogether 8,064 clones were screened. Out of 7,392 HIV synthase variants, 147 positive hits were identified and represent 1.98% of the population screened. Out of the 147 variants isolated in the primary screen, 4 variants remained after two additional rounds of screening. These variants were tested in multiple replicates and in a range of conditions to ensure that the increase of activity is reproducible and not due to an artifact of the assay. Finally, each clone was subjected to DNA sequencing in order to identify the mutation responsible for the change in enzyme activity. Final results are presented in FIG. 4.

II. Example 2: Recombination of Improving Mutation by Direct Mutagenesis

1. Production of Exhaustive Recombinants Library

Previously identified improving mutations (identified as described in Example 1) were recombined by single or successive standard directed mutagenesis reactions to obtain mutants containing more than one mutation.

2. Production and Screening of Purified Enzyme Variants

Variants were produced and purified as follows. Plasmid DNA generated as described above and plasmid DNA containing the sequence coding for the wild type HIV synthase were transformed into BL21(DE3) competent cells and plated out onto LB-agar plates supplemented with the appropriate antibiotic. Cells were grown overnight at 30° C. until individual colonies reach the desired size.

Single transformants were used to inoculate 50 ml of autoinduction medium in order to produce recombinant enzyme in bacteria. Cell pellets containing the overexpressed recombinant HIV synthase variants were stored at −80° C. overnight before being resuspended in lysis buffer (BugBuster, Merck Novagen). The suspension was incubated 10 minutes at room temperature followed by 20 minutes on ice. Cell lysates were clarified by centrifugation and His6 tagged enzymes were purified from clarified lysates by affinity chromatography (Macherey Nagel), concentrated by centrifugation on ultrafiltration membranes (Amicon ultra, Millipore) and desalted by size exclusion chromatography (Zeba spin columns, Perbio Science).

Purified enzymes were characterized in vitro in a coupled, multi-step enzymatic conversion of acetone and acetyl-CoA into IBN (IBN) via 3-hydroxyisovalerate (HIV) and 3-phosphonoxy-isovaleric acid (PIV) using the HIV synthase variants and controls to be assessed and purified HIV phosphorylase and PIV decarboxylase enzymes prepared as outlined above. 40 µg of pure enzyme preparations were incubated in HIV/IBN production buffer (50 mM Tris, 10 mM MgCl2, 20 mM KCl, 0.5 mM DTT, 700 mM acetone, 4 mM acetyl-CoA, 5 mM ATP, 0.5 mM DTT, 5 µg HIV phosphorylase and 85 µg PIV decarboxylase) in 2 ml crimp top glass vials. Glass vials were sealed using crimp caps and incubated for 8 hours at 37° C. to allow enzymatic conversion of substrates into isobutene (IBN). Enzymatic reactions were finally stopped by heat shock denaturation of enzymes at 80° c. for 5 minutes.

Figure 5:
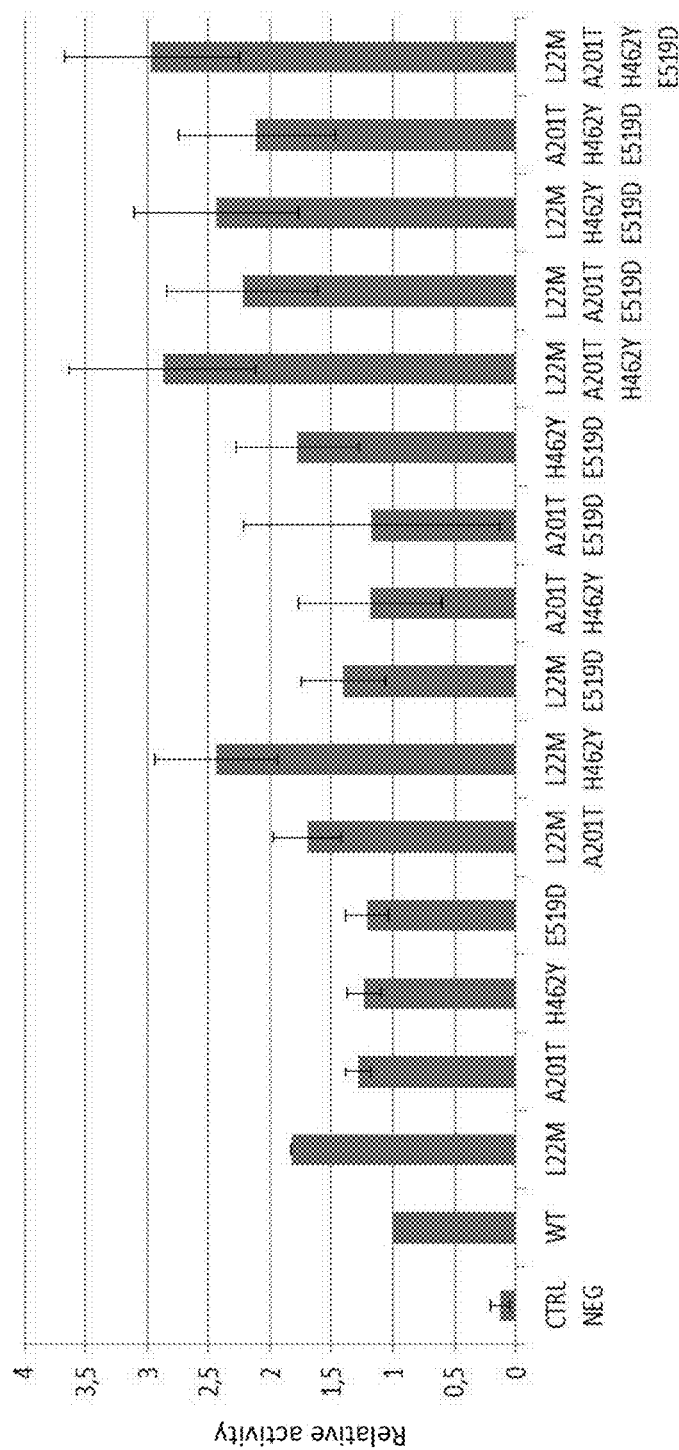

Isobutene (IBN) production was analyzed by gas chromatography for controls and variants as described earlier and results are shown in FIG. 5.

III. Example 3: Directed Evolution of Hmg-CoA Synthase for HIV Production by in Vivo Screening 1. Library Construction A cDNA library coding for single residue mutants of HIV synthase was constructed using standard mutagenesis techniques. The full length coding sequence of a mutated HIV synthase enzyme (previously identified as described in Examples 1 and 2 and bearing mutations L22M, A201T, S221L, H462Y on a SEQ ID NO:1 backbone) with N-term His6 tag was subcloned into commercial peT-25b+ expression vector and used as a template for the mutagenic PCR. The quality control of the library construction consisted of two steps: (1) the amplified DNA fragments obtained were analyzed and quantified against a range of control reactions and (2) DNA sequencing was carried out on 200 randomly-selected clones. The profiles of the DNA fragments were as expected. In term of the DNA sequence analysis of the gene coding for the HIV synthase, approximately 75% of the clones presented single residue mutations while the rest were found wild type.

2. Screening Assay

Plasmid DNA generated as described above and plasmid DNA containing the sequence coding for the wild type HIV synthase were transformed into BL21(DE3) competent cells and plated out onto LB-agar plates supplemented with the appropriate antibiotic. Cells were grown overnight at 30° C. until individual colonies reach the desired size.

Colonies were then picked and individually transferred into 1 mL of liquid LB medium supplemented with the appropriate antibiotic. Cell growth is carried out with agitation for 20 hours at 30° C. LB cultures were used to inoculate 1 ml of autoinduction medium (ZYM medium, Studier F. W; Protein Expr. Purif. 41 (2005), 207-234) supplemented with the appropriate antibiotic. Cultures were grown overnight at 30° C. for 20-22 hours in shacking incubator set at 700 rpm and 85% humidity. The cells were then pelleted by centrifugation and clarified medium was discarded.

Bacterial pellets were resuspended in HIV production medium (Potassium phosphate 200 mM, Citric acid 4 mM, Ammonium chloride 20 mM, NTA mix 1×, glucose 45 g/L and acetone 500 mM) at OD600=10 and transferred to sealed culture vessels and incubated at 37° C. for 16 hours. Bacterial cultures were then deactivated by 5 minutes incubation at 80° C. and allowed to cool at room temperature.

We have previously observed that 3-hydroxyisovalerate (HIV) can be detected in the culture medium of producing cells but that some remains intracellular. Cell lysis at high temperature therefore ensures that production is stopped and that intracellular HIV is released into the culture medium for accurate quantification. 3-hydroxyisovalerate (HIV) produced by bacterial cultures was therefore enzymatically converted to isobutene (IBN) for analysis by GC. 75 µL of 3-hydroxyisovalerate (HIV) containing preparations were, therefore, supplemented with 25 µL HIV revelation buffer (final concentration in reaction are as follows: KCl 20 mM, ATP 20 mM, HIV phosphorylase 5 µg, PIV decarboxylase 85 µg) (the production and purification of the HIV phosphorylase and PIV decarboxylase is described above) in 2 ml crimp top glass vials. Glass vials were sealed using crimp caps and incubated for 24 hours at 37° C. Enzymatic reactions were finally stopped by heat shock denaturation of enzymes at 80° C. for 5 minutes.

The isobutene (IBN) produced spontaneously volatilizes and can be quantified by gas chromatography (GC) analysis of reactions head space. The quantity of IBN produced is directly proportional with the quantity of HIV in reactions and therefore with in vivo HIV synthase activity. It provides an indirect readout of the reaction of interest.

For GC headspace analysis, 100 µl of headspace gases from each enzymatic reaction are injected (Injection parameters: 250° C.; split=10) in a Brucker GC-450 system equipped with a Flame ionization detector (FID) (250° C.; 28 ml·min$^{-1}$ H$_2$; 30 ml·min$^{-1}$ N$_2$; 300 ml·min$^{-1}$ synthetic air). Compounds present in samples were separated by chromatography using a RTX-1 column (15m x 0.32 mm; Restek, France) at 100° C. with a 1 ml·min$^{-1}$ constant flow of carrier gaz (nitrogen 5.0, Messer, France). Upon injection, peak area of isobutene was calculated for samples and standards.

Figure 6:
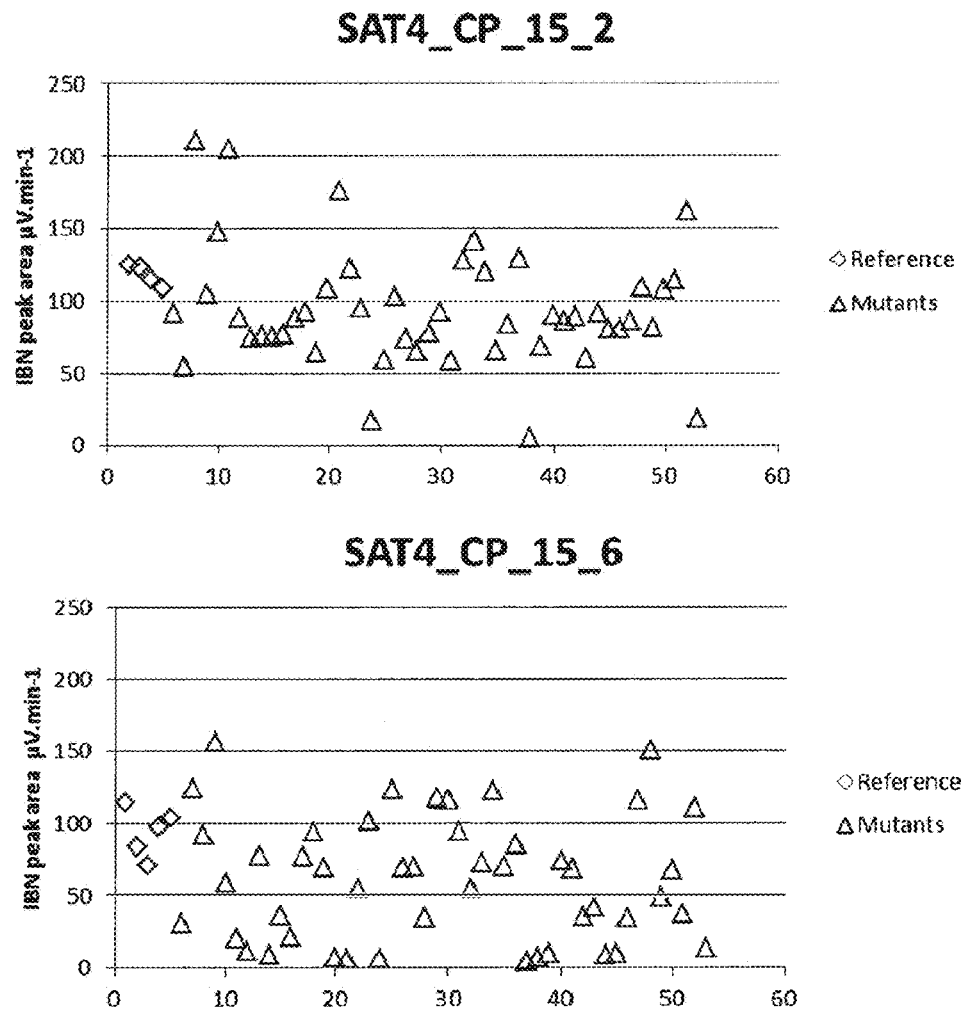

Variants displaying improved activity over that of parental enzyme were identified based on Increased isobutene (IBN) peak area as quantified by GC. An example of screening results is presented in FIG. 6.

3. Identification of Enzyme Variants with Increased Activity

Figure 7:
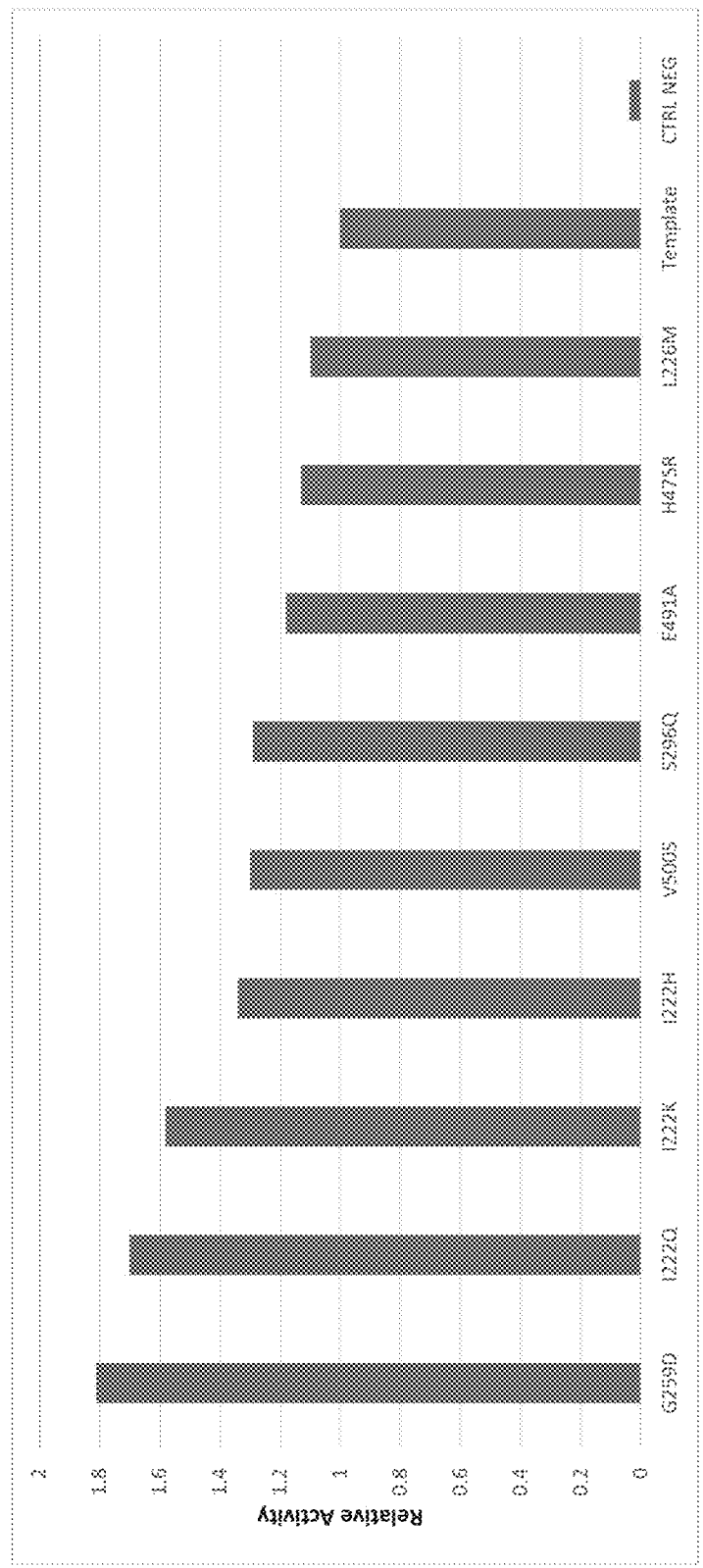

Of the initial HIV synthase variants library 24,960 variants were assayed as described above. Alongside the HIV synthase variants, control reactions were setup including reference controls using wild type HIV synthase enzyme. Altogether 27,560 clones were screened. Out of 24,960 HIV synthase variants, 219 positive hits were identified and represent 0.87% of the population screened. Out of the 219 variants isolated in the primary screen, 11 variants remained after two additional rounds of screening. These variants were tested in multiple replicates and in a range of conditions to ensure that the increase of activity is reproducible and not due to an artifact of the assay. Finally each clone was subjected to DNA sequencing in order to identify the mutation responsible for the change in enzyme activity. Final results are presented in FIG. 7.

Figure 8:
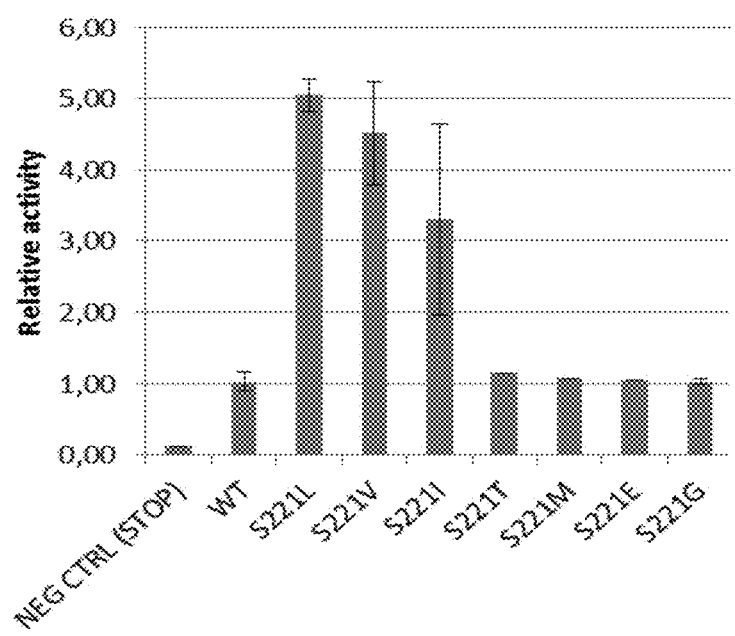
Figure 9:
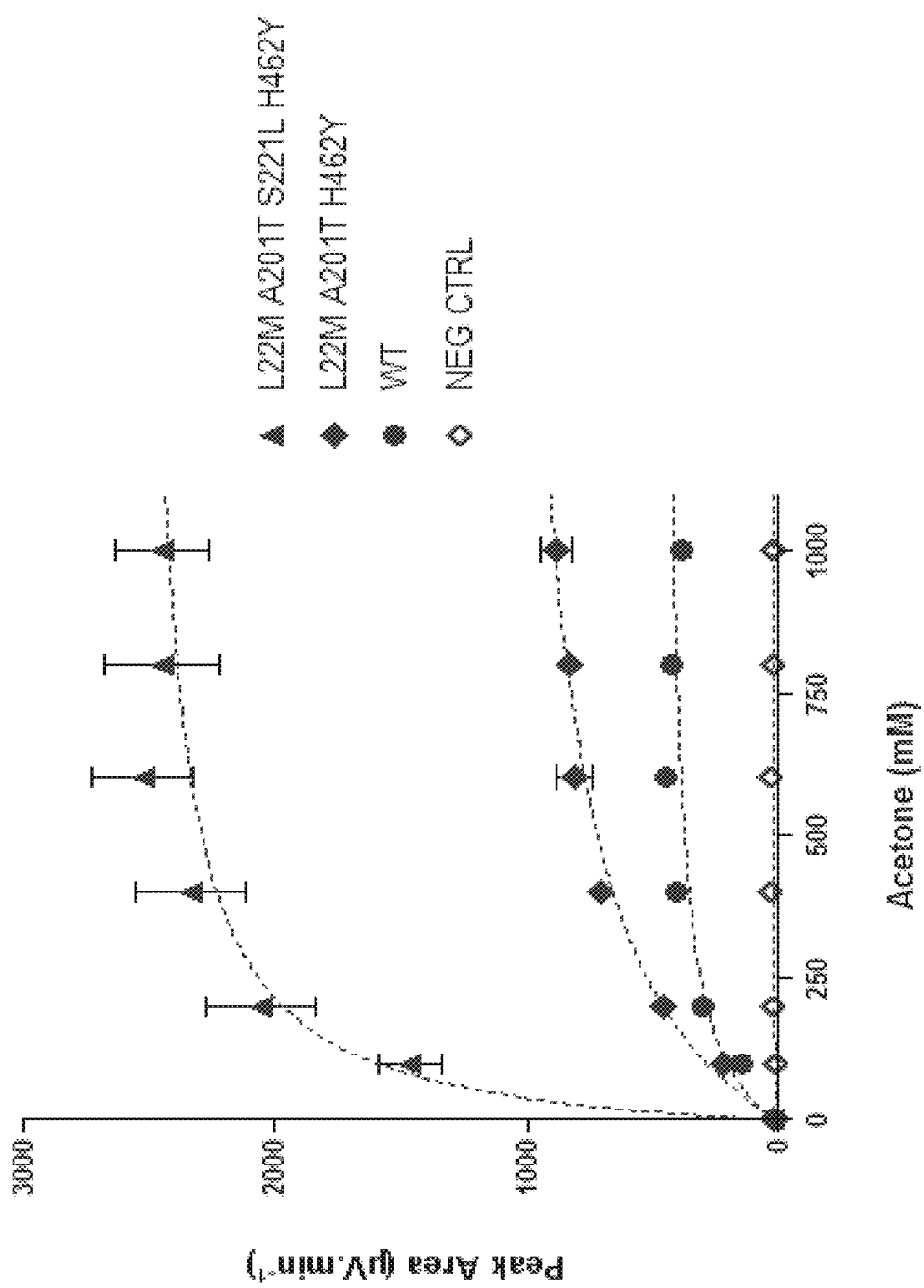
Figure 10:
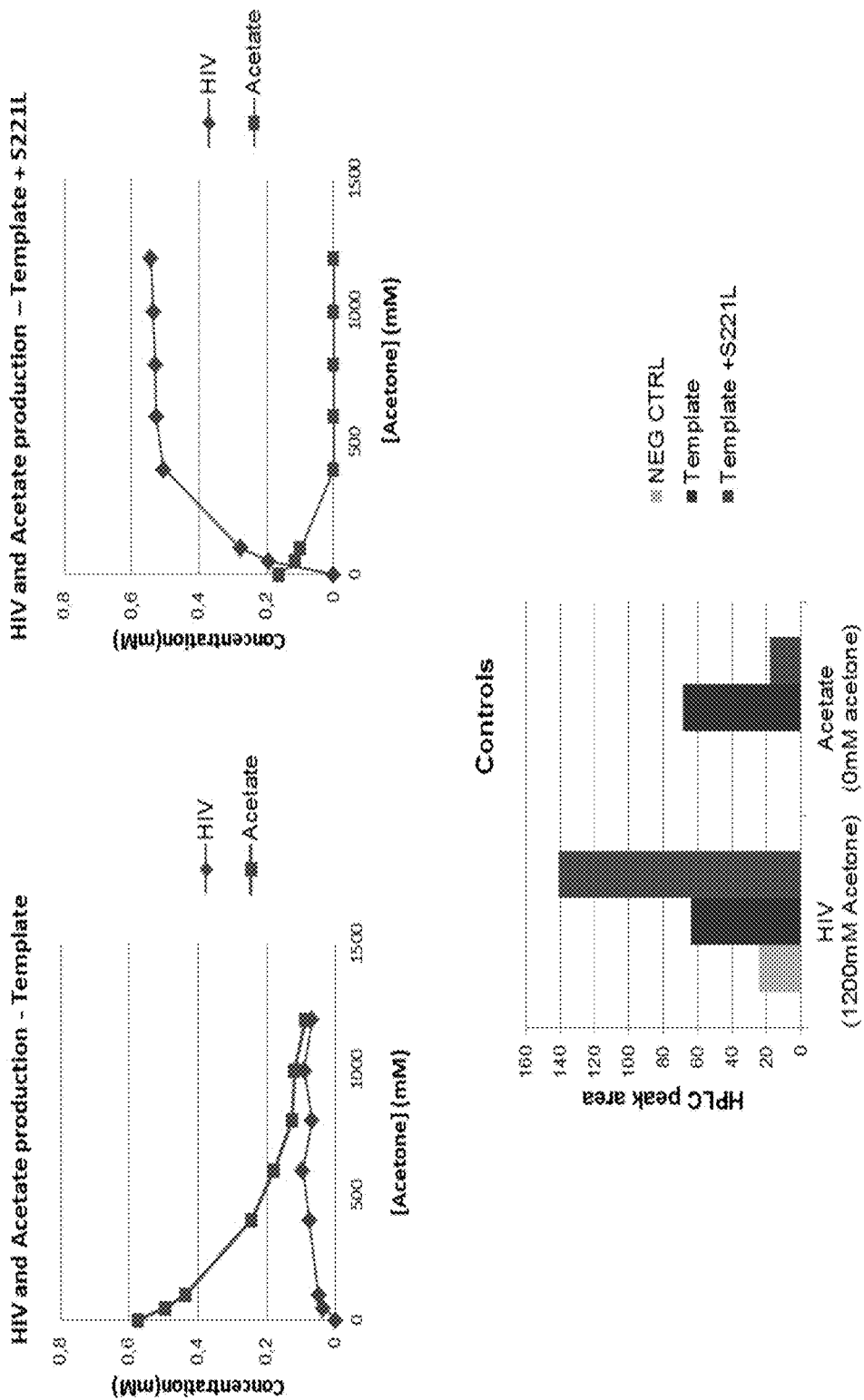

IV. Example 4: Identification of Mutations of Residue 221 of the HIV Synthase that Lead to an Increase in the Activity of HIV Production from Acetone and Acetyl-CoA Mutations S221L and S221V were identified by screening of a mutants library. An exhaustive and systematic test of all possible substitutions at position S221 was carried out in order to assess whether other substitutions could, similarly to S221L and S221V, enhance the activity of the enzyme. 48 clones were randomly selected out of a cDNA library mutagenized at position S221 and subjected to DNA sequencing in order to select as many substitutions out of the 19 amino acids possible other than WT sequence. The plasmid DNA for all expression vectors encoding these variants were transformed into BL21(DE3) and single transformants were used to inoculate 1 ml of autoinduction medium in order to produce recombinant enzyme in bacteria. Cell pellets containing the overexpressed recombinant HIV synthase variants were stored at −80° C. overnight before being resuspended in 200 µl lysis buffer (BugBuster, Merck Novagen). The suspension was incubated 10 minutes at room temperature followed by 20 minutes on ice. Cell lysates were clarified by centrifugation and His6 tagged enzymes were purified from clarified by lysates by affinity chromatography (Macherey Nagel), concentrated by centrifugation over ultrafiltration membranes (Amicon ultra, Millipore) and desalted by size exclusion chromatography (Zeba spin columns, Perbio Science). Enzymatic reactions were setup in 2 ml glass vials using 70 µl of enzyme preparation and 30 µl of reaction mix (final concentrations are 50 mM Tris pH 7.5, 10 mM MgCl$_2$, 20 mM KCl, 4 mM acetyl-CoA, 125 mM acetone, 5 mM ATP, 0.5 mM DTT, 5 µg HIV phosphorylase and 85 µg P/V decarboxylase; the production and purification of the HIV phosphorylase and PIV decarboxylase is described above). Vials were sealed and incubated at 37° C. for 8 hours followed by 5 min at 80° C. to stop the enzymatic reactions. The isobutene produced was previously shown to be directly proportional to 3-hydroxyisovalerate (HIV) production and was, therefore, quantified by gas chromatography as readout of HIV synthase activity as follows. 100 µl of headspace gases from each enzymatic reaction are injected (Injection parameters: 250° C.; split=10) in a Brucker GC-450 system equipped with a Flame ionization detector (FID) (250° C.; 28 ml·min$^{-1}$ H$_2$; 30 ml·min$^{-1}$ N2; 300 ml·min$^{-1}$ synthetic air). Compounds present in samples were separated by chromatography using a RTX-1 column (15m x 0.32 mm; Restek, France) at 100° C. with a 1 ml·min$^-$ constant flow of carrier gas (nitrogen 5.0, Messer, France). Upon injection, peak area of isobutene was calculated for samples and standards; see FIG. 8.

V. Example 5: Determination of Kinetic Constants for HIV Synthases

Michaelis-Menten apparent steady state kinetics constants for the overall reaction of HIV production from acetone and acetyl-CoA—$K_{cat}^{app}$ and $K_m^{app}$—were determined using the following protocol.

Plasmid DNA containing the sequence coding for the wild type HIV synthase and variants showing increased HIV synthesis activity were transformed into BL21(DE3) competent cells and plated out onto LB agar petri dishes supplemented with the appropriate antibiotic.

Cells were grown overnight at 30° C. and isolated transformants were picked and used to inoculate autoinduction medium (ZYM medium, Studier F. W; Protein Expr. Purif. 41 (2005), 207-234). The cultures were then grown overnight at 30° C. for 20-22 hours in shaking incubator. The cells were pelleted and stored at −80° C. overnight.

Frozen cell pellets were thawed on ice and resuspended in adequate amounts of Bugbuster (Merck Novagen) and incubated for 10 minutes at room temperature followed by 20 minutes on ice to allow cell lysis to proceed. Raw lysates were then clarified by centrifugation and His6 tagged enzymes were purified by affinity chromatography (Macherey Nagel).

40 μg of purified enzymes were then mixed with HIV production buffer (50 mM Tris, 10 mM MgCl2, 20 mM KCl, 0.5 mM DTT, 4 mM Ac-CoA) supplemented with a range of acetone concentrations (0 to 1200 mM). Enzymatic reactions were thus setup in 2 ml sealed glass vials and were incubated for 2 hours at 37° C. followed by a 5 minutes deactivation at 80° C. to spot the reaction. Reactions were clarified by centrifugation and supernatant was transferred to a fresh tube to which IBN production reagents were added (50 mM Tris pH 7.5, 5 mM ATP, 20 mM KCl, 5 μg HIV phosphorylase and 85 μg PIV decarboxylase; the production and purification of the HIV phosphorylase and PIV decarboxylase used is described above). 3-hydroxyisovalerate (HIV) to isobutene (IBN) conversion for reactions and standards was performed for 24 hours at 37° C. 100 μl of headspace gases from each enzymatic reaction were then injected (Injection parameters: 250° C.; split=10) in a Brucker GC-450 system equipped with a Flame ionization detector (FID) (250° C.; 28 ml·min$^{-1}$ $H_2$; 30 ml·min$^{-}$ $N_2$; 300 ml·min$^{-1}$ synthetic air). Compounds present in samples were separated by chromatography using a RTX-1 column (15m x 0.32 mm; Restek, France) at 100° C. with a 1 ml·min$^{-}$ constant flow of carrier gas (nitrogen 5.0, Messer, France) and peak area of isobutene was calculated for samples and standards as shown in FIG. 9.

In order to quantify absolute amounts of isobutene (IBN) and 3-hydroxyisovalerate (HIV) produced a range of concentrations of HIV (0.25 to 2 mM) were subjected to enzymatic conversion to IBN as applied to samples and a range of concentrations of pure IBN (1 to 100,000 ppm) were used to calibrate the gas chromatograph. Both calibrations curves showed the response to be linear within the selected range. The production rates of HIV (moles of HIV/mole enzyme/sec) were plotted as a function of the concentration of acetone and the curve was fitted using Michaelis Menten equation:

$$V = \frac{(Vmax \times [\text{substrate}])}{(Km + [\text{substrate}])}$$

TABLE 8

Kinetic data for wild type and improved mutants

| Enzyme | Kcat ($s^{-1}$) | Kcat fold increase | Km (mM) | Kcat/Km ($10^{-2}$ $s^{-1}$/mM) | Kcat/Km fold increase |
|---|---|---|---|---|---|
| Wild type enzyme | $0.93 \times 10^{-2}$ | — | 158 | 0.0059 | — |
| Template | $2.19 \times 10^{-2}$ | 2.44 | 331 | 0.0066 | 1.12 |
| Template + S221L | $4.97 \times 10^{-2}$ | 5.44 | 77 | 0.0645 | 10.93 |

VI. Example 6: Characterization of Reaction Modifying Mutation at Position S221

It is of interest to note that in the presence of acetyl-CoA but in absence of the secondary substrate acetone, the enzyme effectively performs reaction (1) followed by (2') instead of (1) followed by (2).

Enzyme-S+Acetyl-CoA→Enzyme-S-Ac+CoA-SH (1)

Enzyme-S-Acetyl+Acetone+$H_2O$→Enzyme-SH+HIV (2)

Enzyme-S-Acetyl+$H_2O$→Enzyme-SH+Acetate (2')

It is therefore of importance to monitor both HIV and Acetate production in WT and mutant enzymes to assess the relative efficiency of acetate production in the absence or at low acetone concentrations. Mutations have been shown to specifically suppress reaction (2') while enhancing the successive reactions (1) and (2) leading to increased HIV production when both substrates (Acetyl-CoA and Acetone) are present. Such results are shown in FIG. 10 for one mutation at position 221.

Enzymatic reactions are setup as described in Example 5 but stopped before conversion of 3-hydroxyisovalerate (HIV) to isobutene (IBN). HIV and Acetate production are monitored by HPLC for each assay, control and production calibration samples in triplicate to quantify product formation (Hi Plex H 30com column set at 30° C. and 0.4 ml/min mobile phase (5.5 mM $H_2SO_4$ solution).

VII. Example 7: Characterization of HMG CoA Synthesis Activity of Variants Displaying Improved HIV Synthesis Activity Variants were produced and purified in the laboratory as follows. Plasmid DNA generated as described above and plasmid DNA containing the sequence coding for the wild type HIV synthase were transformed into BL21(DE3) competent cells and plated out onto LB-agar plates supplemented with the appropriate antibiotic. Cells were grown overnight at 30° C. until individual colonies reach the desired size.

Single transformants were used to inoculate 50 ml of autoinduction medium in order to produce recombinant enzyme in bacteria. Cell pellets containing the overexpressed recombinant HIV synthase variants were stored at −80° C. overnight before being resuspended in lysis buffer (BugBuster, Merck Novagen). The suspension was incubated 10 minutes at room temperature followed by 20 minutes on ice. Cell lysates were clarified by centrifugation and His6 tagged enzymes were purified from clarified lysates by affinity chromatography (Macherey Nagel), concentrated by centrifugation on ultrafiltration membranes (Amicon ultra, Millipore) and desalted by size exclusion chromatography (Zeba spin columns, Perbio Science).

HMG CoA synthase activity can be measured by methods well known in the art. One possible and preferably used assay is described, e.g. in Clinkenbeard et al. (J. Biol. Chem 250 (1975), 3108-3116). In this assay HMG-CoA synthase activity is measured by monitoring the decrease in the absorbance at 303 nm that accompanies the acetyl-CoA-dependent disappearance of the enolate form of acetoacetyl-CoA.

The following three items were prepared individually on ice:

Purified enzymes to be tested were diluted (1.6 mg/ml in 50 mM Tris pH 7.5 buffer)

Reaction buffer (50 mM Tris pH 7.5, 20 mM $MgCl_2$, 0.5 mM DTT, 0.2 mM AcCoA)

Substrate (1 mM AcAcCoA in 50 mM Tris pH 7.5)

Reagents were then mixed together on ice and immediately transferred to a spectrophotometer chamber set at 30° C. with shaking. Decrease in absorbency at 303 nm is monitored for 30 minutes for assay reactions and appropriate controls in the absence of enzymes or substrates. Enzyme activity (in µmole/mg of enzyme/minute) is calculated from the slope of the curve obtained from the change in Abs(303 nm) in time. Results for WT HIV synthase (SEQ ID NO:1) and 11 variants are shown in Table 9 and expressed as the ratio of the specific HMG CoA synthase activity of each variant over the specific HMG CoA synthase activity of the WT enzyme. Corresponding HIV synthase activity for each variant also expressed relatively to that of the WT enzyme is also presented alongside.

TABLE 9

HMG CoA synthesis activity of variants displaying improved HIV synthesis activity. Corresponding HMG CoA- and HIV synthase activities of HIV synthase variants displaying concomitantly increased HIV synthase activity and decreased HMG CoA synthase activity.

| Sequence | Relative HMG CoA synthesis activity | Relative HIV synthesis activity |
|---|---|---|
| WT | 1 | 1 |
| L22M A201T H462Y | 0.76 | 2.04 |
| L22M A201T S221L G259D H462Y | 0.54 | 15.51 |
| L22M T165P A201T S221L I222Q G259D H462Y | 0.46 | 23.91 |
| L22M K75N T165P A201T S221L I222K G259D S296Q H462Y N473G M481S | 0.23 | 16.82 |
| L22M A201T S221L H462Y | 0.19 | 8.57 |
| L22M T165Q A201T S221L I222K L226M K246R G259D S296Q H462Y N473D H475R V500S | 0.125 | 15.295 |
| L22M K75N T165Q A201T S221L I222Q G259D S296Q H462Y H475R | 0.1 | 18.55 |
| L22M A201T S221L I222K H462Y | 0 | 13.54 |
| L22M K75N T165P A201T S221L I222K S296Q H462Y N473D H475R V500S | 0 | 19.75 |
| WT | 1 | 1 |
| L22M A201T H462Y | 0.76 | 2.04 |

VIII. Example 8: Characterization of HMG CoA Synthesis Activity of Variants Displaying Improved HIV Synthesis Activity 1. Identification of HIV Synthase Variants with Improved HIV Synthesis Activity A combinatorial library was constructed in order to recombine a collection of amino acids mutations that had been identified in previous screens. The combinatorial library was constructed using the HIV synthase L22M A201T S221L H462Y variant as a template. This sequence was randomized at 19 positions in order to introduce 26 distinct mutations as detailed in Table 10. The construction of the combinatorial library used standard techniques of gene synthesis based on the assembly of overlapping sense and antisense oligonucleotides designed to match the targeted gene sequence (Czar et al, 2009 Trends in Biotechnology 27:63-72; Kodumal et al, 2004, Proc. Natl. Acad. Sci. USA 101:15573-15578; Smith et al 2003, Proc. Natl. Acad. Sci. USA 101:15440-15445; Xiong et al, 2008, FEMS Microbiol. Rev. 32:552-540). Briefly, a mixture of 69 34-35-mer oligonucleotides representing the HIV synthase L22M A201T S221L H462Y variant backbone was prepared at a final concentration of 50 μM and spiked with oligonucleotides mutated at the targeted amino acid positions (0.05 to 0.4 μM). PCR like reactions, without DNA template, were set up using 3 μl of the oligonucleotide mixtures and 0.5 μl of Pfx polymerase (LifeTechnologies) in order to assemble the gene from the oligonucleotides. The rate of mutations per clone was controlled by the ratio of backbone oligonucleotides to mutated oligonucleotides. A further cycle of PCR amplification of the reassembled gene was performed using primers situated at the 5' and 3' end of the gene was carried out. Finally, the amplified fragment was sub-cloned into the commercial peT-300/NT-DEST (LifeTechnologies).

The combinatorial library was screened using the in vivo screening assay as follows. Plasmid DNA generated as described above and plasmid DNA containing the sequence coding for the reference HIV synthase L22M A201T S221L H462Y were transformed into BL21(DE3) competent cells and plated out onto LB-agar plates supplemented with the appropriate antibiotic. Cells were grown overnight at 30° C. until individual colonies reach the desired size. Single colonies were then picked and individually transferred into 75 μL of liquid LB medium supplemented with the appropriate antibiotic. Cell growth is carried out with shaking for 20 hours at 30° C. The LB cultures were used to inoculate 300 μl of Terrific broth supplemented with the appropriate antibiotic. Cultures were grown overnight at 30° C. for 20 hours in shaking incubator set at 700 rpm and 90% humidity. Cells were finally pelleted and the supernatant discarded. Bacterial pellets were resuspended in HIV production medium (Potassium phosphate 200 mM, Citric acid 4 mM, Ammonium chloride 20 mM, NTA mix 1×, glucose 45 g/L and acetone 250 mM) at final OD600=10 and transferred to sealed culture vessels and incubated at 37° C. for 6 hours. Bacterial cultures were then deactivated by 5 minutes incubation at 80° C. and allowed to cool at room temperature. HIV produced by bacterial cultures was enzymatically converted to IBN for analysis by GC. The HIV containing preparations were therefore supplemented with 5 μL HIV revelation buffer (final concentrations in reaction are as follows: KCl 20 mM, ATP 20 mM, HIV phosphorylase 2 μg, PIV decarboxylase 50 μg; HIV phosphorylase and PIV decarboxylase as produced and purified as described above). The enzymatic reactions were sealed and incubated for 24 hours at 37° C. Enzymatic reactions were finally stopped by heat shock denaturation of enzymes at 80° C. for 5 minutes. The isobutene (IBN) produced was quantified by gas chromatography (GC) according to the method described in Example 3. Table 11 presents a list of variants identified in this screen and their corresponding improvement factor compared to the control variant.

TABLE 10

List of mutations recombined in the combinatorial library

| Wild type sequence | Position | Mutations of interest |
|---|---|---|
| L | 22 | M |
| I | 24 | M |
| K | 75 | N |
| K | 100 | L |
| T | 165 | P/Q |
| A | 201 | T |

TABLE 10-continued

List of mutations recombined in the combinatorial library

| Wild type sequence | Position | Mutations of interest |
|---|---|---|
| I | 222 | Q/K/H/R |
| L | 226 | M |
| G | 259 | D |
| L | 270 | I/M/H |
| S | 296 | Q |
| H | 462 | Y |
| N | 473 | G/D |
| H | 475 | R |
| G | 480 | C |
| M | 481 | S |
| V | 500 | S |
| V | 514 | S |
| E | 519 | D |

TABLE 11

List of variants with increased HIV synthesis activity compared to L22M A201T S221L H462Y variant

| Variant sequence | HIV production relative to template (L22M A201T S221L H462Y) |
|---|---|
| L22M K75N T165Q A201T S221L I222Q G259D S296Q H462Y H475R | 3.7 |
| L22M I24M K75N K100L T165P A201T S221L I222Q L226M K246R G259D L270I H462Y N473D G480C V500S | 3.6 |
| L22M K75N T165Q A201T S221L I222Q L226M G259D L270M S296Q H462Y N473D G480C V500S | 3.4 |
| L22M I24M T165P A201T S221L I222K L226M G259D L270M S296Q H462Y H475R | 3.4 |
| L22M K75N T165P A201T S221L I222K G259D S296Q H462Y N473G M481S | 3.4 |
| L22M K75N T165P A201T S221L I222H L226M K246R G259D H462Y N473D G480C | 3.2 |
| L22M K75N A201T S221L I222H G259D S296Q H462Y N473G G480C V500S | 3.1 |
| L22M K75N T165P A201T S221L I222K S296Q H462Y N473D H475R V500S | 3.1 |
| L22M I24M K75N T165Q A201T S221L I222Q L226M K246R G259D S296Q H462Y N473D G480C V500S | 2.9 |
| L22M T165Q A201T S221L I222K L226M K246R G259D S296Q H462Y N473D H475R V500S | 2.9 |
| L22M A201T I24M K75N T165P S221L I222K L226M H462Y | 2.9 |
| L22M I24M K75N T165Q A201T S221L I222Q L226M K246R G259D L270I S296Q H462Y N473D G480C M481S V500S | 2.7 |
| L22M K75N T165Q A201T S221L H462Y I222K S296Q G480C V500S | 2.7 |
| L22M K75N T165P A201T S221L I222K K246R G259D H462Y V500S | 2.7 |
| L22M I24M T165Q A201T S221L I222K L226M G259D H462Y H475R V500S | 2.6 |
| L22M I24M K75N A201T S221L I222Q L226M G259D H462Y N473D M481S | 2.6 |
| L22M I24M K75N K100L T165P A201T S221L I222K K246R G259D S296Q H462Y N473G M481S V500S | 2.6 |
| L22M K75N A201T S221L I222Q L226M H462Y N473D V500S | 2.5 |
| L22M I24M K75N T165Q A201T S221L I222H G259D H462Y G480C | 2.5 |
| L22M I24M K75N A201T S221L I222Q K246R S296Q H462Y N473G H475R | 2.3 |
| L22M A201T S221L H462Y T165Q I222H G259D S296Q N473G G480C | 2.3 |
| L22M I24M K75N T165P A201T S221L I222K L226M K246R G259D H462Y H475R V500S | 2.2 |
| L22M I24M K75N T165Q A201T S221L I222H K246R S296Q H462Y N473G G480C V500S | 2.2 |
| L22M K75N T165QA201T S221L H462Y I222Q S296Q H475R G480C M481S | 2.2 |

TABLE 11-continued

List of variants with increased HIV synthesis activity compared to L22M A201T S221L H462Y variant

| Variant sequence | HIV production relative to template (L22M A201T S221L H462Y) |
|---|---|
| L22M K75N T165P A201T S221L I222Q G259D L270I S296Q H462Y H475R V500S | 2.2 |
| L22M I24M K75N K100L T165P A201T S221L I222H L226M K246R G259D L270M S296Q H462Y N473D H475R | 2.1 |
| L22M I24M K75N A201T S221L I222H G259D L270I S296Q H462Y H475R | 2.1 |
| L22M I24M K75N K100L T165P A201T S221L I222K L226M K246R G259D L270M H462Y N473D V500S | 2.1 |
| L22M I24M K75N T165Q A201T S221L L226M K246R G259D L270I S296Q H462Y H475R V500S V514S | 2.1 |
| L22M I24M K75N T165Q A201T S221L I222K L226M G259D H462Y N473G | 2.1 |
| L22M I24M K75N T165Q A201T S221L I222Q L226M K246R G259D L270M S296Q H462Y N473D G480C | 2.0 |
| L22M K75N A201T S221L G259D S296Q H462Y N473G G480C | 2.0 |
| L22M I24M K75N T165P A201T S221L I222K L226M K246R L270M S296Q H462Y N473G G480C M481S V500S | 2.0 |
| L22M K75N T165Q A201T S221L I222H K246R G259D L270I S296Q H462Y N473G G480C M481S | 2.0 |
| L22M I24M K75N T165Q A201T S221L I222R K246R G259D H462Y N473D G480C V500S E519D | 1.9 |
| L22M I24M K75N T165P A201T S221L I222K L226M S296Q H462Y | 1.8 |
| L22M I24M K75N K100L T165P A201T S221L I222H K246R G259D L270M H462Y N473G G480C V500S | 1.8 |
| L22M K75N T165Q A201T S221L H462Y | 1.8 |
| L22M I24M K75N T165Q A201T S221L I222Q K246R G259D L270M H462Y N473G V514S | 1.7 |
| L22M I24M K75N K100L T165P A201T S221L I222K K246R G259D L270M S296Q H462Y N473G M481S | 1.7 |
| L22M K75N T165Q A201T S221L L226M G259D L270I H462Y N473D V500S | 1.7 |
| L22M K75N A201T S221L I222Q L226M K246R S296Q H462Y G480C V500S | 1.6 |
| L22M I24M A201T S221L I222Q H462Y | 1.6 |
| L22M I24M K75N T165Q A201T S221L I222H L226M L270M H462Y H475R | 1.5 |
| L22M I24M K75N T165Q A201T S221L I222Q L226M K246R G259D L270M S296Q H462Y H475R V500S | 1.5 |
| L22M I24M K75N T165Q A201T S221L L226M K246R G259D S296Q H462Y G480C V500S | 1.5 |
| L22M K75N T165P A201T S221L I222K L226M K246R G259D L270M H462Y N473D H475R | 1.4 |
| L22M I24M K75N A201T S221L I222H L270M S296Q H462Y V500S | 1.4 |
| L22M A201T S221L H462Y | 1.0 |

2. Analysis of the HMG CoA Synthesis Activity of Variants with Improved HIV Synthesis Activity A collection of 5 variants was selected out of Table 11 and their HMG CoA synthesis activity was assessed according to the assay described in Example 7. Results obtained for the 5 variants are shown in Table 12 and presented as the ratio of the specific HMG coA synthesis activity of each variant over the specific activity of the library template (L22M A201T S221L H462Y) and one of the best performing variant L22M A201T S221L H462Y G259D T165P I222Q L71 W13L K75N (variant constructed based on mutations isolated in a range of screens). Of particular interest are the variants L22M K75N T165P A201T S221L I222K S296Q H462Y N473D H475R V500S and L22M T165Q A201T S221L I222K L226M K246R G259D S296Q H462Y N473D H475R V500S that are characterized by an activity of HIV synthesis high compared to the two controls while their HMG-CoA synthesis activity is significantly decreased compared to the two controls.

TABLE 12

| | HIV synthesis relative activity compared to L7I W13L L22M K75N T165P A201T S221L I222Q G259D H462Y variant | HMG CoA synthesis relative activity compared to L7I W13L L22M K75N T165P A201T S221L I222Q G259D H462Y variant |
|---|---|---|
| L7I W13L L22M K75N T165P A201T S221L I222Q G259D H462Y | 1.00 | 1.00 |
| L22M A201T S221L H462Y | 0.40 | 0.23 |
| L22M K75N T165Q A201T S221L I222Q G259D S296Q H462Y H475R | 0.83 | 0.30 |
| L22M K75N T165P A201T S221L I222K | 0.81 | 0.00 |

TABLE 12-continued

| | HIV synthesis relative activity compared to L7I W13L L22M K75N T165P A201T S221L I222Q G259D H462Y variant | HMG CoA synthesis relative activity compared to L7I W13L L22M K75N T165P A201T S221L I222Q G259D H462Y variant |
|---|---|---|
| S296Q H462Y N473D H475R V500S | | |
| L22M K75N T165P A201T S221L I222K G259D S296Q H462Y N473G M481S | 0.79 | 0.36 |
| L22M K75N T165P A201T S221L I222H L226M K246R G259D H462Y N473D G480C | 0.73 | 0.91 |
| L22M T165Q A201T S221L I222K L226M K246R G259D S296Q H462Y N473D H475R V500S | 0.72 | 0.00 |

IX. Example 9: Mutation I222K Confers a Loss of HMG CoA Synthesis Activity

The mutation I222K was of particular interest since (1) it lies in proximity with position S221 which is described as suppressing the production of acetate while enhancing the HIV production (see Example 6); (2) it is found in variants characterized with low HMGCoA synthesis ability (see Example 8). The importance of this mutation for both reactions was further tested.

The coding sequences for variant L22M A201T S221L H462Y and variant L22M A201T S221L H462Y I222K were subcloned in pET25b+ bacterial expression vector (Merck-Novagen). These enzyme variants were produced and purified as described in Example 2. The HMGCoA synthesis activity and the HIV synthesis activity were measured as described in Example 7 and 2 respectively. Results are presented in Table 13 and indicate that the I222K mutation is critical to HMGCoA synthesis.

TABLE 13

| | HIV synthesis relative activity compared to L22M A201T S221L H462Y variant | HMG CoA synthesis relative activity compared to L22M A201T S221L H462Y variant |
|---|---|---|
| L22M A201T S221L H462Y | 1.0 | 1.0 |
| L22M A201T S221L H462Y I222K | 1.6 | 0.0 |

Figure 11:
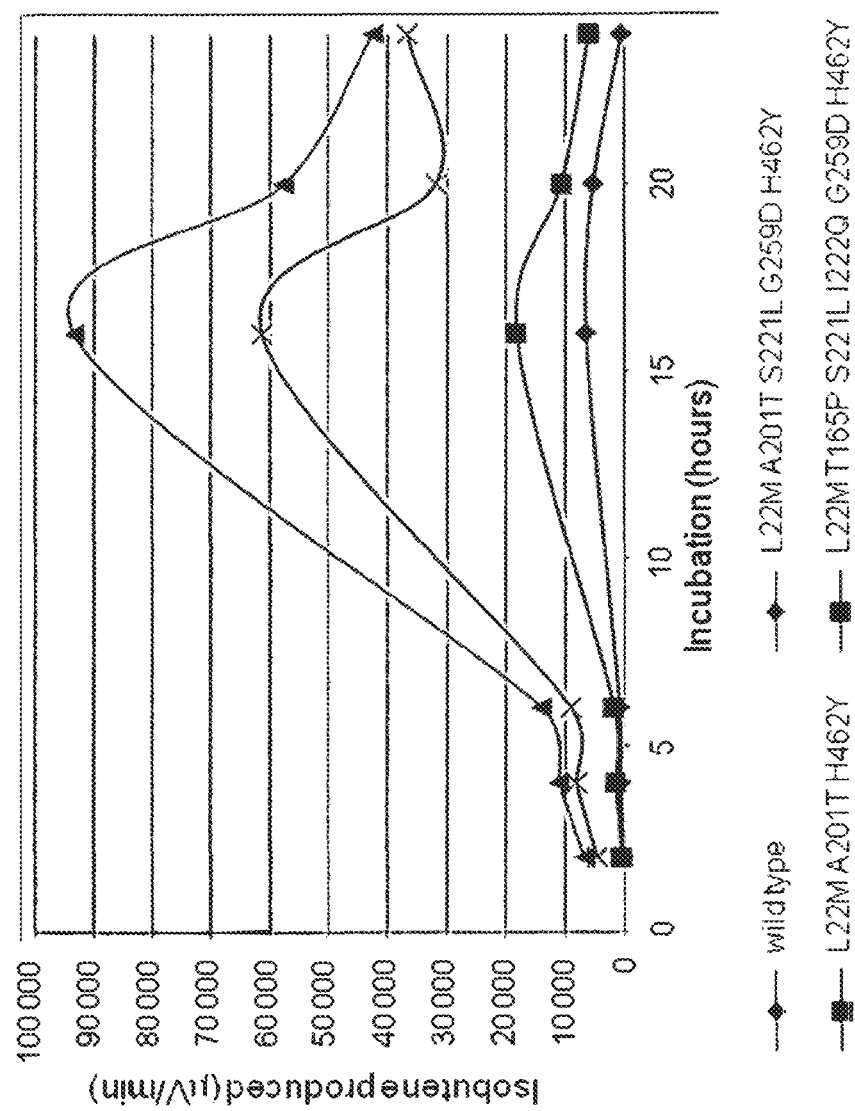

X. Example 10: Characterization of HIV Synthase Variants in a Whole Cell Assay A selection of best performing HIV synthase variants obtained from sequential rounds of evolution were further characterized in a whole cell assay. This assay is based on the use of bacterial strain transformed with an expression vector (Merck-Novagen peT25b(+)) that contains the coding sequences and lead to the production of the 3 enzymes involved in the metabolic pathway converting acetone to isobutene; namely the HIV synthase for the production of HIV; the HIV phosphorylase for the production of PIV and the PIV decarboxylase for the conversion of PIV into isobutene (See FIG. 1); the production and purification of the HIV phosphorylase and the PIV decarboxylase is described above. The wild type HIV synthase, variant L22M A201T H462Y; variant L22M A201T S221L G259D H462Y and variant L22M T165P A201T S221L I222Q G259D H462Y were subcloned in the expression vector containing the HIV phosphorylase and PIV decarboxylase coding sequences. BL21(DE3) competent cells were transformed with these vectors and the cells were plated out and grown 24 hours at 30° C. on LB plates supplemented with the appropriate antibiotic. Single transformants were then used to inoculate 1 ml of LB culture medium and grown at 30° C. for 20 hours in a shaking incubator set at 700 rpm and 85% humidity. These starter cultures were used to inoculate 1 ml of auto-induction medium (Studier F. W; Protein Expr. Purif. 41 (2005), 207-234) and grown for a further 24 hours at 30° C. in a shaking incubator set at 700 rpm and 85% humidity. The cultures were centrifuged for 10 minutes at 4000 rpm and the supernatant discarded. The cell pellets containing the three overexpressed recombinant enzymes was then resuspended in 500 µl of minimum medium supplemented with acetone and glucose (Potassium phosphate 200 mM, Citric acid 4 mM, Ammonium chloride 20 mM, NTA mix 1×, glucose 45 g/L and acetone 500 mM). The cell suspensions, in sealed containers, were incubated at 37° C. for 2-4-6-16-20-24 hours in a shaking incubator. The Isobutene produced was then quantified by GC according to the method described in the previous examples. Results presented in FIG. 11 show that all 3 variants produce increased amount of isobutene compared to the wild type enzyme throughout the assay time course.

XI. Example 11: Improving HIV Synthesis Activity and Reducing HMG-CoA Synthesis Activity by Transfer of Mutation The mutation I222K has been shown in Example 9 as being beneficial for reducing the HMG-CoA synthesis activity.

By transferring the mutation I222K and mutating one of the best performing variant L22M A201T S221L H462Y G259D T165P I222Q L71 W13L K75N, a new variant L22M A201T S221L I222K H462Y G259D T165P L71 W13R K75N was produced presenting both an increase in HIV synthesis and a decrease in HMG-CoA synthesis.

The variants were subcloned in pET25b+ bacterial expression vector (Merck-Novagen). These enzyme variants were produced and purified as described in Example 2. The HMGCoA synthesis activities were measured as described in Example 7. The HIV synthesis activities were measured as followed. Plasmid DNA were transformed into BL21 (DE3) competent cells and plated out onto LB-agar plates supplemented with the appropriate antibiotic. Cells were grown overnight at 30° C. until individual colonies reach the desired size. Single colonies were then picked and individually transferred into 1 mL of liquid LB medium supplemented with the appropriate antibiotic. Cell growth is carried out with shaking for 20 hours at 30° C. The LB cultures were used to inoculate 300 µL of of auto-induction medium (Studier et al) supplemented with the appropriate antibiotic and grown for a further 24 hours at 30° C. in a shaking incubator set at 900 rpm and 85% humidity. Cells were finally pelleted and the supernatant discarded. Bacterial pellets were resuspended in 30 µL HIV production medium (Potassium phosphate 200 mM, Citric acid 4 mM, Ammonium chloride 20 mM, NTA mix 1×, glucose 45 g/L, magnesium sulfate 1 mM and acetone 25 mM) supplemented with the appropriate antibiotic and incubated at 30° C. for 4 hours. Bacterial cultures were then deactivated by 5 minutes incubation at 80° C. and allowed to cool at 4° C. overnight. HIV produced by bacterial cultures was enzymatically converted to IBN for analysis by GC. The HIV containing preparations were therefore supplemented with 5 µL lysis buffer (Tris/HCl pH 7.5 50 mM, Lysonase 0.25% (Merck-Novagen)) and 10 μL of revelation buffer prepared as followed. A plasmid vector containing the HIV phosphorylase and PIV decarboxylase was transformed into BL21 (DE3) competent cells and plated out onto LB-agar plates supplemented with the appropriate antibiotic. Cells were grown overnight at 30° C. until individual colonies reach the desired size. Single colonies were then picked and individually transferred into 20 mL of liquid LB medium supplemented with the appropriate antibiotic. Cell growth is carried out with shaking for 20 hours at 30° C. The LB cultures were used to inoculate 500 mL of auto-induction medium (Studier et al) supplemented with the appropriate antibiotic and grown for a further 24 hours at 30° C. in a shaking incubator set at 900 rpm and 85% humidity. Cells were finally pelleted and the supernatant discarded. Following a 30 min freezing at −80° C., cells were resuspended in 50 mL of lysis buffer (Tris/HCl pH 7.5 50 mM, magnesium chloride 2 mM, potassium chloride 20 mM, ATP 15 mM, Lysonase 0.25% (Merck-Novagen)). The enzymatic reactions were sealed and incubated for 7 hours at 37° C. Enzymatic reactions were finally stopped by heat shock denaturation of enzymes at 80° C. for 5 minutes. The IBN produced was quantified by gas chromatography (GC) according to the method described in Example 3. Results are presented in Table 14.

TABLE 14

| | HIV synthesis relative activity compared to L22M A201T S221L H462Y G259D T165P I222Q L7I W13L K75N variant | HMG CoA synthesis relative activity compared to L22M A201T S221L H462Y G259D T165P I222Q L7I W13L K75N variant |
|---|---|---|
| L22M A201T S221L H462Y G259D T165P I222Q L7I W13L K75N | 1.0 | 1.0 |
| L22M A201T S221L I222K H462Y G259D T165P L7I W13R K75N | 1.29 | 0.25 |

XII. Example 12: Directed Evolution of HMG-CoA Synthase for in Vivo HIV Production by in Vitro Screening Plasmid DNA containing one of the best performing variant L22M A201T S221L I222K H462Y G259D T165P L71 W13R K75N was subjected to standard mutagenesis protocols to generate a library of single or double residues mutations variants. This library was screened as described in Example 11. The best described variants are shown in Table 15.

TABLE 15

| Mutations | HIV synthesis relative activity compared to L22M A201T S221L I222K H462Y G259D T165P L7I W13R K75N variant |
|---|---|
| T171A-S338P | 1.92 |
| T171A-E325L | 1.51 |
| N167A-T171A | 1.51 |
| Q33E | 1.51 |
| T171A | 1.44 |
| S338P | 1.25 |
| T171G-E325V | 1.16 |
| A54G | 1.14 |

The invention claimed is:

1. A 3-hydroxyisovalerate (HIV) synthase variant showing an improved activity in converting acetone and a compound which provides an activated acetyl group characterized by the following formula (I):

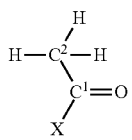

into 3-hydroxyisovalerate over the corresponding HIV synthase from which it is derived, wherein X is selected from the group consisting of S—CH2-CH2-NH—CO—CH2-CH2-NH—CO—CH(OH)—C(CH3)2-CH2-O—PO2H—O—PO2H—C10H13N5O7P (coenzyme A), S—CH2-CH2-NH—CO—CH2-CH2-NH—CO—CH(OH)—C(CH3)2-CH2-O—PO2H-polypeptide (acyl-carrier protein), S—CH2-CH2-NH—CO—CH2-CH2-NH—CO—CH(OH)—C(CH3)2-CH2-OH (pantetheine), S—$CH_2$-$CH_2$-NH—CO—$CH_3$ (N-acetyl-cysteamine), S—$CH_3$ (methane thiol), S—CH2-CH(NH2)-CO2H (cysteine), S—CH2-CH2-CH(NH2)-CO2H (homocysteine), S—CH2-CH(NH—C5H8NO3)-CO—NH—CH2-CO2H (glutathione), S—$CH_2$-$CH_2$-$SO_3$H (coenzyme M) and OH (acetic acid), and wherein the HIV synthase variant is derived from the amino acid sequence as shown in SEQ ID NO:1 or an amino acid sequence having at least 80% sequence identity to SEQ ID NO:1, and in which the HIV synthase variant comprises one or more amino acid residues at a position selected from the group consisting of:
  (1) an amino acid residue at position 33 in the amino acid sequence shown in SEQ ID NO:1 or at a position corresponding to this position in the sequence from which the HIV synthase variant is derived, is substituted; and/or
  (2) an amino acid residue at position 74 in the amino acid sequence shown in SEQ ID NO:1 or at a position corresponding to this position in the sequence from which the HIV synthase variant is derived, is deleted or substituted; and/or
  (3) an amino acid residue at position 171 in the amino acid sequence shown in SEQ ID NO:1 or at a position corresponding to this position in the sequence from which the HIV synthase variant is derived, is substituted; and/or
  (4) an amino acid residue at position 221 in the amino acid sequence shown in SEQ ID NO:1 or at a position corresponding to this position in the sequence from which the HIV synthase variant is derived, is deleted or substituted; and/or
  (5) an amino acid residue at position 222 in the amino acid sequence shown in SEQ ID NO:1 or at a position corresponding to this position in the sequence from which the HIV synthase variant is derived, is deleted or substituted; and/or
  (6) an amino acid residue at position 338 in the amino acid sequence shown in SEQ ID NO:1 or at a position corresponding to this position in the sequence from which the HIV synthase variant is derived, is deleted or substituted; and/or
  (7) an amino acid residue at position 345 in the amino acid sequence shown in SEQ ID NO:1 or at a position corresponding to this position in the sequence from which the HIV synthase variant is derived, is deleted or substituted; and/or
  (8) an amino acid residue at position 394 in the amino acid sequence shown in SEQ ID NO:1 or at a position corresponding to this position in the sequence from which the HIV synthase variant is derived, is deleted or substituted; and/or
  (9) an amino acid residue at position 396 in the amino acid sequence shown in SEQ ID NO:1 or at a position corresponding to this position in the sequence from which the HIV synthase variant is derived, is substituted.

2. The HIV synthase variant of claim 1, wherein the HIV synthase variant is derived from the amino acid sequence shown in SEQ ID NO:1.

3. The HIV synthase variant of claim 1, wherein the HIV synthase variant is derived from a sequence having at least 90% sequence identity to SEQ ID NO:1.

4. The HIV synthase variant of claim 1 comprising an amino acid sequence at least 95% sequence identity to SEQ ID NO:1.

5. The HIV synthase variant of claim 1, wherein the HIV synthase variant further comprises one or more amino acid residues at a position selected from the group consisting of:
  (1) an amino acid residue at position 7 in the amino acid sequence shown in SEQ ID NO:1 or at a position corresponding to this position in the sequence from which the HIV synthase variant is derived, is deleted or substituted; and/or
  (2) an amino acid residue at position 13 in the amino acid sequence shown in SEQ ID NO:1 or at a position corresponding to this position in the sequence from which the HIV synthase variant is derived, is deleted or substituted; and/or
  (3) an amino acid residue at position 22 in the amino acid sequence shown in SEQ ID NO:1 or at a position corresponding to this position in the sequence from which the HIV synthase variant is derived, is deleted or substituted; and/or
  (4) an amino acid residue at position 24 in the amino acid sequence shown in SEQ ID NO:1 or at a position corresponding to this position in the sequence from which the HIV synthase variant is derived, is deleted or substituted; and/or
  (5) an amino acid residue at position 38 in the amino acid sequence shown in SEQ ID NO:1 or at a position corresponding to this position in the sequence from which the HIV synthase variant is derived, is deleted or substituted; and/or
  (6) an amino acid residue at position 41 in the amino acid sequence shown in SEQ ID NO:1 or at a position corresponding to this position in the sequence from which the HIV synthase variant is derived, is deleted or substituted; and/or
  (7) an amino acid residue at position 43 in the amino acid sequence shown in SEQ ID NO:1 or at a position corresponding to this position in the sequence from which the HIV synthase variant is derived, is deleted or substituted; and/or
  (8) an amino acid residue at position 54 in the amino acid sequence shown in SEQ ID NO:1 or at a position corresponding to this position in the sequence from which the HIV synthase variant is derived, is deleted or substituted; and/or (9) an amino acid residue at position 75 in the amino acid sequence shown in SEQ ID NO:1 or at a position corresponding to this position in the sequence from which the HIV synthase variant is derived, is deleted or substituted; and/or
(10) an amino acid residue at position 81 in the amino acid sequence shown in SEQ ID NO:1 or at a position corresponding to this position in the sequence from which the HIV synthase variant is derived, is deleted or substituted; and/or

(11) an amino acid residue at position 165 in the amino acid sequence shown in SEQ ID NO:1 or at a position corresponding to this position in the sequence from which the HIV synthase variant is derived, is deleted or substituted; and/or

(12) an amino acid residue at position 167 in the amino acid sequence shown in SEQ ID NO:1 or at a position corresponding to this position in the sequence from which the HIV synthase variant is derived, is deleted or substituted; and/or

(13) an amino acid residue at position 201 in the amino acid sequence shown in SEQ ID NO:1 or at a position corresponding to this position in the sequence from which the HIV synthase variant is derived, is deleted or substituted; and/or

(14) an amino acid residue at position 226 in the amino acid sequence shown in SEQ ID NO:1 or at a position corresponding to this position in the sequence from which the HIV synthase variant is derived, is deleted or substituted; and/or

(15) an amino acid residue at position 246 in the amino acid sequence shown in SEQ ID NO:1 or at a position corresponding to this position in the sequence from which the HIV synthase variant is derived, is deleted or substituted; and/or

(16) an amino acid residue at position 259 in the amino acid sequence shown in SEQ ID NO:1 or at a position corresponding to this position in the sequence from which the HIV synthase variant is derived, is deleted or substituted; and/or

(17) an amino acid residue at position 296 in the amino acid sequence shown in SEQ ID NO:1 or at a position corresponding to this position in the sequence from which the HIV synthase variant is derived, is deleted or substituted; and/or

(18) an amino acid residue at position 325 in the amino acid sequence shown in SEQ ID NO:1 or at a position corresponding to this position in the sequence from which the HIV synthase variant is derived, is deleted or substituted; and/or

(19) an amino acid residue at position 363 in the amino acid sequence shown in SEQ ID NO:1 or at a position corresponding to this position in the sequence from which the HIV synthase variant is derived, is deleted or substituted; and/or

(20) an amino acid residue at position 457 in the amino acid sequence shown in SEQ ID NO:1 or at a position corresponding to this position in the sequence from which the HIV synthase variant is derived, is deleted or substituted; and/or

(21) an amino acid residue at position 462 in the amino acid sequence shown in SEQ ID NO:1 or at a position corresponding to this position in the sequence from which the HIV synthase variant is derived, is deleted or substituted; and/or

(22) an amino acid residue at position 473 in the amino acid sequence shown in SEQ ID NO:1 or at a position corresponding to this position in the sequence from which the HIV synthase variant is derived, is deleted or substituted; and/or

(23) an amino acid residue at position 475 in the amino acid sequence shown in SEQ ID NO:1 or at a position corresponding to this position in the sequence from which the HIV synthase variant is derived, is deleted or substituted; and/or

(24) an amino acid residue at position 480 in the amino acid sequence shown in SEQ ID NO:1 or at a position corresponding to this position in the sequence from which the HIV synthase variant is derived, is deleted or substituted; and/or

(25) an amino acid residue at position 481 in the amino acid sequence shown in SEQ ID NO:1 or at a position corresponding to this position in the sequence from which the HIV synthase variant is derived, is deleted or substituted; and/or

(26) an amino acid residue at position 486 in the amino acid sequence shown in SEQ ID NO:1 or at a position corresponding to this position in the sequence from which the HIV synthase variant is derived, is deleted or substituted; and/or

(27) an amino acid residue at position 490 in the amino acid sequence shown in SEQ ID NO:1 or at a position corresponding to this position in the sequence from which the HIV synthase variant is derived, is deleted or substituted; and/or

(28) an amino acid residue at position 491 in the amino acid sequence shown in SEQ ID NO:1 or at a position corresponding to this position in the sequence from which the HIV synthase variant is derived, is deleted or substituted; and/or

(29) an amino acid residue at position 500 in the amino acid sequence shown in SEQ ID NO:1 or at a position corresponding to this position in the sequence from which the HIV synthase variant is derived, is deleted or substituted; and/or

(30) an amino acid residue at position 514 in the amino acid sequence shown in SEQ ID NO:1 or at a position corresponding to this position in the sequence from which the HIV synthase variant is derived, is deleted or substituted; and/or

(31) an amino acid residue at position 516 in the amino acid sequence shown in SEQ ID NO:1 or at a position corresponding to this position in the sequence from which the HIV synthase variant is derived, is deleted or substituted; and/or

(32) an amino acid residue at position 519 in the amino acid sequence shown in SEQ ID NO:1 or at a position corresponding to this position in the sequence from which the HIV synthase variant is derived, is deleted or substituted; and/or

(33) an amino acid residue at position 520 in the amino acid sequence shown in SEQ ID NO:1 or at a position corresponding to this position in the sequence from which the HIV synthase variant is derived, is deleted or substituted.

6. The HIV synthase variant of claim 5, wherein:

(1) the amino acid residue at position 7 in the amino acid sequence shown in SEQ ID NO:1 or at a position corresponding to this position in the sequence from which the HIV synthase variant is derived, is deleted or substituted with isoleucine or glycine; and/or (2) the amino acid residue at position 13 in the amino acid sequence shown in SEQ ID NO:1 or at a position corresponding to this position in the sequence from which the HIV synthase variant is derived, is deleted or substituted with arginine or leucine; and/or
(3) the amino acid residue at position 22 in the amino acid sequence shown in SEQ ID NO:1 or at a position corresponding to this position in the sequence from which the HIV synthase variant is derived, is deleted or substituted with methionine; and/or
(4) the amino acid residue at position 24 in the amino acid sequence shown in SEQ ID NO:1 or at a position corresponding to this position in the sequence from which the HIV synthase variant is derived, is deleted or substituted with methionine; and/or
(5) the amino acid residue at position 33 in the amino acid sequence shown in SEQ ID NO:1 or at a position corresponding to this position in the sequence from which the HIV synthase variant is derived, is substituted with glutamic acid; and/or
(6) the amino acid residue at position 38 in the amino acid sequence shown in SEQ ID NO:1 or at a position corresponding to this position in the sequence from which the HIV synthase variant is derived, is deleted or substituted with glycine; and/or
(7) the amino acid residue at position 41 in the amino acid sequence shown in SEQ ID NO:1 or at a position corresponding to this position in the sequence from which the HIV synthase variant is derived, is deleted or substituted with serine; and/or
(8) the amino acid residue at position 43 in the amino acid sequence shown in SEQ ID NO:1 or at a position corresponding to this position in the sequence from which the HIV synthase variant is derived, is deleted or substituted with valine; and/or
(9) the amino acid residue at position 54 in the amino acid sequence shown in SEQ ID NO:1 or at a position corresponding to this position in the sequence from which the HIV synthase variant is derived, is deleted or substituted with glycine; and/or
(10) the amino acid residue at position 74 in the amino acid sequence shown in SEQ ID NO:1 or at a position corresponding to this position in the sequence from which the HIV synthase variant is derived, is deleted or substituted with glutamic acid; and/or
(11) the amino acid residue at position 81 in the amino acid sequence shown in SEQ ID NO:1 or at a position corresponding to this position in the sequence from which the HIV synthase variant is derived, is deleted or substituted with arginine; and/or
(12) the amino acid residue at position 165 in the amino acid sequence shown in SEQ ID NO:1 or at a position corresponding to this position in the sequence from which the HIV synthase variant is derived, is deleted or substituted with proline armor glutamine; and/or
(13) the amino acid residue at position 167 in the amino acid sequence shown in SEQ ID NO:1 or at a position corresponding to this position in the sequence from which the HIV synthase variant is derived, is deleted or substituted with alanine; and/or
(14) the amino acid residue at position 171 in the amino acid sequence shown in SEQ ID NO:1 or at a position corresponding to this position in the sequence from which the HIV synthase variant is derived, is deleted or substituted with alanine or glycine; and/or
(15) the amino acid residue at position 201 in the amino acid sequence shown in SEQ ID NO:1 or at a position corresponding to this position in the sequence from which the HIV synthase variant is derived, is deleted or substituted with threonine; and/or
(16) the amino acid residue at position 221 in the amino acid sequence shown in SEQ ID NO:1 or at a position corresponding to this position in the sequence from which the HIV synthase variant is derived, is deleted or substituted with leucine, valine, isoleucine or threonine; and/or
(17) the amino acid residue at position 222 in the amino acid sequence shown in SEQ ID NO:1 or at a position corresponding to this position in the sequence from which the HIV synthase variant is derived, is deleted or substituted with arginine, glutamine, lysine or histidine; and/or
(18) the amino acid residue at position 226 in the amino acid sequence shown in SEQ ID NO:1 or at a position corresponding to this position in the sequence from which the HIV synthase variant is derived, is deleted or substituted with methionine; and/or
(19) the amino acid residue at position 246 in the amino acid sequence shown in SEQ ID NO:1 or at a position corresponding to this position in the sequence from which the HIV synthase variant is derived, is deleted or substituted with arginine; and/or
(20) the amino acid residue at position 259 in the amino acid sequence shown in SEQ ID NO:1 or at a position corresponding to this position in the sequence from which the HIV synthase variant is derived, is deleted or substituted with aspartic acid; and/or
(21) the amino acid residue at position 296 in the amino acid sequence shown in SEQ ID NO:1 or at a position corresponding to this position in the sequence from which the HIV synthase variant is derived, is deleted or substituted with glutamine; and/or
(22) the amino acid residue at position 325 in the amino acid sequence shown in SEQ ID NO:1 or at a position corresponding to this position in the sequence from which the HIV synthase variant is derived, is deleted or substituted with alanine, leucine or valine; and/or
(23) the amino acid residue at position 338 in the amino acid sequence shown in SEQ ID NO:1 or at a position corresponding to this position in the sequence from which the HIV synthase variant is derived, is deleted or substituted with proline; and/or
(24) the amino acid residue at position 345 in the amino acid sequence shown in SEQ ID NO:1 or at a position corresponding to this position in the sequence from which the HIV synthase variant is derived, is deleted or substituted with phenylalanine; and/or
(25) the amino acid residue at position 363 in the amino acid sequence shown in SEQ ID NO:1 or at a position corresponding to this position in the sequence from which the HIV synthase variant is derived, is deleted or substituted with arginine; and/or
(26) the amino acid residue at position 394 in the amino acid sequence shown in SEQ ID NO:1 or at a position corresponding to this position in the sequence from which the HIV synthase variant is derived, is substituted with serine; and/or
(27) the amino acid residue at position 396 in the amino acid sequence shown in SEQ ID NO:1 or at a position corresponding to this position in the sequence from which the HIV synthase variant is derived, is deleted or substituted with asparagine; and/or
(28) the amino acid residue at position 457 in the amino acid sequence shown in SEQ ID NO:1 or at a position corresponding to this position in the sequence from which the HIV synthase variant is derived, is deleted or substituted with cysteine; and/or

(29) the amino acid residue at position 462 in the amino acid sequence shown in SEQ ID NO:1 or at a position corresponding to this position in the sequence from which the HIV synthase variant is derived, is deleted or substituted with tyrosine; and/or
(30) the amino acid residue at position 473 in the amino acid sequence shown in SEQ ID NO:1 or at a position corresponding to this position in the sequence from which the HIV synthase variant is derived, is deleted or substituted with aspartic acid or glycine; and/or
(31) the amino acid residue at position 475 in the amino acid sequence shown in SEQ ID NO:1 or at a position corresponding to this position in the sequence from which the HIV synthase variant is derived, is deleted or substituted with arginine; and/or
(32) the amino acid residue at position 480 in the amino acid sequence shown in SEQ ID NO:1 or at a position corresponding to this position in the sequence from which the HIV synthase variant is derived, is deleted or substituted with cysteine; and/or
(33) the amino acid residue at position 481 in the amino acid sequence shown in SEQ ID NO:1 or at a position corresponding to this position in the sequence from which the HIV synthase variant is derived, is deleted or substituted with serine; and/or
(34) the amino acid residue at position 486 in the amino acid sequence shown in SEQ ID NO:1 or at a position corresponding to this position in the sequence from which the HIV synthase variant is derived, is deleted or substituted with arginine; and/or
(35) the amino acid residue at position 490 in the amino acid sequence shown in SEQ ID NO:1 or at a position corresponding to this position in the sequence from which the HIV synthase variant is derived, is deleted or substituted with asparagine; and/or
(36) the amino acid residue at position 491 in the amino acid sequence shown in SEQ ID NO:1 or at a position corresponding to this position in the sequence from which the HIV synthase variant is derived, is deleted or substituted with alanine; and/or
(37) the amino acid residue at position 500 in the amino acid sequence shown in SEQ ID NO:1 or at a position corresponding to this position in the sequence from which the HIV synthase variant is derived, is deleted or substituted with serine; and/or
(38) the amino acid residue at position 514 in the amino acid sequence shown in SEQ ID NO:1 or at a position corresponding to this position in the sequence from which the HIV synthase variant is derived, is deleted or substituted with arginine, glycine or serine; and/or
(39) the amino acid residue at position 516 in the amino acid sequence shown in SEQ ID NO:1 or at a position corresponding to this position in the sequence from which the HIV synthase variant is derived, is deleted or substituted with asparagine; and/or
(40) the amino acid residue at position 519 in the amino acid sequence shown in SEQ ID NO:1 or at a position corresponding to this position in the sequence from which the HIV synthase variant is derived, is deleted or substituted with aspartic acid; and/or
(41) the amino acid residue at position 520 in the amino acid sequence shown in SEQ ID NO:1 or at a position corresponding to this position in the sequence from which the HIV synthase variant is derived, is deleted or substituted with serine.

7. The HIV synthase variant of claim 1, wherein said HIV synthase variant further comprises an amino acid residue at position 75 in the amino acid sequence shown in SEQ ID NO:1 or at a position corresponding to this position in the sequence from which the HIV synthase variant is derived, is deleted or substituted with asparagine.

8. The HIV synthase variant of claim 1, wherein X is S—CH2-CH2-NH—CO—CH2-CH2-NH—CO—CH(OH)—C(CH3)2-CH2-O—PO2H—O—PO2H—C10H13N5O7P (coenzyme A).

9. The HIV synthase variant of claim 1, wherein the HIV synthase variant is capable of converting acetone and the compound into 3-hydroxyisovalerate (HIV) at a turnover rate of at least $0.93\times10^{-2}$ $s^{-1}$.

10. A nucleic acid molecule encoding the HIV synthase variant of claim 1.

11. A vector comprising the nucleic acid of claim 10.

12. A host cell comprising the vector of claim 11.

13. An in vitro or in vivo method of producing 3-hydroxyisovalerate (HIV), comprising enzymatically converting by the HIV synthase variant of claim 1 acetone and a compound which provides an activated acetyl group characterized by the following formula (I):

into 3-hydroxyisovalerate (HIV), wherein X is selected from the group consisting of S—CH2-CH2-NH—CO—CH2-CH2-NH—CO—CH(OH)—C(CH3)2-CH2-O—PO2H—O—PO2H—C10H13N5O7P (coenzyme A), S—CH2-CH2-NH—CO—CH2-CH2-NH—CO—CH(OH)—C(CH3)2-CH2-O—PO2H-polypeptide (acyl-carrier protein), S—CH2-CH2-NH—CO—CH2-CH2-NH—CO—CH(OH)—C(CH3)2-CH2-OH (pantetheine), S—CH2-CH2-NH—CO—$CH_3$ (N-acetyl-cysteamine), S—$CH_3$ (methane thiol), S—CH2-CH(NH2)-CO2H (cysteine), S—CH2-CH2-CH(NH2)-CO2H (homocysteine), S—CH2-CH(NH—C5H8NO3)-CO—NH—CH2-CO2H (glutathione), S—$CH_2$—$CH_2$—$SO_3H$ (coenzyme M) and OH (acetic acid) to produce HIV.

14. The method of claim 13, wherein the HIV synthase variant is derived from the amino acid sequence shown in SEQ ID NO:1.

15. The method of claim 13, wherein the HIV synthase variant is derived from a sequence having at least 90% sequence identity to SEQ ID NO:1.

16. The method of claim 15, wherein the HIV synthase variant comprises an amino acid sequence at least 95% sequence identity to SEQ ID NO:1.

17. The method of claim 13, the HIV synthase variant further comprises one or more amino acid residues at a position selected from the group consisting of:

(1) an amino acid residue at position 7 in the amino acid sequence shown in SEQ ID NO:1 or at a position corresponding to this position in the sequence from which the HIV synthase variant is derived, is deleted or substituted; and/or (2) an amino acid residue at position 13 in the amino acid sequence shown in SEQ ID NO:1 or at a position corresponding to this position in the sequence from which the HIV synthase variant is derived, is deleted or substituted; and/or (3) an amino acid residue at position 22 in the amino acid sequence shown in SEQ ID NO:1 or at a position corresponding to this position in the sequence from which the HIV synthase variant is derived, is deleted or substituted; and/or (4) an amino acid residue at position 24 in the amino acid sequence shown in SEQ ID NO:1 or at a position corresponding to this position in the sequence from which the HIV synthase variant is derived, is deleted or substituted; and/or (5) an amino acid residue at position 38 in the amino acid sequence shown in SEQ ID NO:1 or at a position corresponding to this position in the sequence from which the HIV synthase variant is derived, is deleted or substituted; and/or (6) an amino acid residue at position 41 in the amino acid sequence shown in SEQ ID NO:1 or at a position corresponding to this position in the sequence from which the HIV synthase variant is derived, is deleted or substituted; and/or (7) an amino acid residue at position 43 in the amino acid sequence shown in SEQ ID NO:1 or at a position corresponding to this position in the sequence from which the HIV synthase variant is derived, is deleted or substituted; and/or (8) an amino acid residue at position 54 in the amino acid sequence shown in SEQ ID NO:1 or at a position corresponding to this position in the sequence from which the HIV synthase variant is derived, is deleted or substituted; and/or (9) an amino acid residue at position 75 in the amino acid sequence shown in SEQ ID NO:1 or at a position corresponding to this position in the sequence from which the HIV synthase variant is derived, is deleted or substituted; and/or

(10) an amino acid residue at position 81 in the amino acid sequence shown in SEQ ID NO:1 or at a position corresponding to this position in the sequence from which the HIV synthase variant is derived, is deleted or substituted; and/or

(11) an amino acid residue at position 165 in the amino acid sequence shown in SEQ ID NO:1 or at a position corresponding to this position in the sequence from which the HIV synthase variant is derived, is deleted or substituted; and/or

(12) an amino acid residue at position 167 in the amino acid sequence shown in SEQ ID NO:1 or at a position corresponding to this position in the sequence from which the HIV synthase variant is derived, is deleted or substituted; and/or

(13) an amino acid residue at position 201 in the amino acid sequence shown in SEQ ID NO:1 or at a position corresponding to this position in the sequence from which the HIV synthase variant is derived, is deleted or substituted; and/or

(14) an amino acid residue at position 226 in the amino acid sequence shown in SEQ ID NO:1 or at a position corresponding to this position in the sequence from which the HIV synthase variant is derived, is deleted or substituted; and/or

(15) an amino acid residue at position 246 in the amino acid sequence shown in SEQ ID NO:1 or at a position corresponding to this position in the sequence from which the HIV synthase variant is derived, is deleted or substituted; and/or

(16) an amino acid residue at position 259 in the amino acid sequence shown in SEQ ID NO:1 or at a position corresponding to this position in the sequence from which the HIV synthase variant is derived, is deleted or substituted; and/or

(17) an amino acid residue at position 296 in the amino acid sequence shown in SEQ ID NO:1 or at a position corresponding to this position in the sequence from which the HIV synthase variant is derived, is deleted or substituted; and/or

(18) an amino acid residue at position 325 in the amino acid sequence shown in SEQ ID NO:1 or at a position corresponding to this position in the sequence from which the HIV synthase variant is derived, is deleted or substituted; and/or

(19) an amino acid residue at position 363 in the amino acid sequence shown in SEQ ID NO:1 or at a position corresponding to this position in the sequence from which the HIV synthase variant is derived, is deleted or substituted; and/or

(20) an amino acid residue at position 457 in the amino acid sequence shown in SEQ ID NO:1 or at a position corresponding to this position in the sequence from which the HIV synthase variant is derived, is deleted or substituted; and/or

(21) an amino acid residue at position 462 in the amino acid sequence shown in SEQ ID NO:1 or at a position corresponding to this position in the sequence from which the HIV synthase variant is derived, is deleted or substituted; and/or

(22) an amino acid residue at position 473 in the amino acid sequence shown in SEQ ID NO:1 or at a position corresponding to this position in the sequence from which the HIV synthase variant is derived, is deleted or substituted; and/or

(23) an amino acid residue at position 475 in the amino acid sequence shown in SEQ ID NO:1 or at a position corresponding to this position in the sequence from which the HIV synthase variant is derived, is deleted or substituted; and/or

(24) an amino acid residue at position 480 in the amino acid sequence shown in SEQ ID NO:1 or at a position corresponding to this position in the sequence from which the HIV synthase variant is derived, is deleted or substituted; and/or

(25) an amino acid residue at position 481 in the amino acid sequence shown in SEQ ID NO:1 or at a position corresponding to this position in the sequence from which the HIV synthase variant is derived, is deleted or substituted; and/or

(26) an amino acid residue at position 486 in the amino acid sequence shown in SEQ ID NO:1 or at a position corresponding to this position in the sequence from which the HIV synthase variant is derived, is deleted or substituted; and/or

(27) an amino acid residue at position 490 in the amino acid sequence shown in SEQ ID NO:1 or at a position corresponding to this position in the sequence from which the HIV synthase variant is derived, is deleted or substituted; and/or

(28) an amino acid residue at position 491 in the amino acid sequence shown in SEQ ID NO:1 or at a position corresponding to this position in the sequence from which the HIV synthase variant is derived, is deleted or substituted; and/or

(29) an amino acid residue at position 500 in the amino acid sequence shown in SEQ ID NO:1 or at a position corresponding to this position in the sequence from which the HIV synthase variant is derived, is deleted or substituted; and/or
(30) an amino acid residue at position 514 in the amino acid sequence shown in SEQ ID NO:1 or at a position corresponding to this position in the sequence from which the HIV synthase variant is derived, is deleted or substituted; and/or
(31) an amino acid residue at position 516 in the amino acid sequence shown in SEQ ID NO:1 or at a position corresponding to this position in the sequence from which the HIV synthase variant is derived, is deleted or substituted; and/or
(32) an amino acid residue at position 519 in the amino acid sequence shown in SEQ ID NO:1 or at a position corresponding to this position in the sequence from which the HIV synthase variant is derived, is deleted or substituted; and/or
(33) an amino acid residue at position 520 in the amino acid sequence shown in SEQ ID NO:1 or at a position corresponding to this position in the sequence from which the HIV synthase variant is derived, is deleted or substituted.

18. The method of claim 17, wherein:
(1) the amino acid residue at position 7 in the amino acid sequence shown in SEQ ID NO:1 or at a position corresponding to this position in the sequence from which the HIV synthase variant is derived, is deleted or substituted with isoleucine or glycine; and/or
(2) the amino acid residue at position 13 in the amino acid sequence shown in SEQ ID NO:1 or at a position corresponding to this position in the sequence from which the HIV synthase variant is derived, is deleted or substituted with arginine or leucine; and/or
(3) the amino acid residue at position 22 in the amino acid sequence shown in SEQ ID NO:1 or at a position corresponding to this position in the sequence from which the HIV synthase variant is derived, is deleted or substituted with methionine; and/or
(4) the amino acid residue at position 24 in the amino acid sequence shown in SEQ ID NO:1 or at a position corresponding to this position in the sequence from which the HIV synthase variant is derived, is deleted or substituted with methionine; and/or
(5) the amino acid residue at position 33 in the amino acid sequence shown in SEQ ID NO:1 or at a position corresponding to this position in the sequence from which the HIV synthase variant is derived, is substituted with glutamic acid; and/or
(6) the amino acid residue at position 38 in the amino acid sequence shown in SEQ ID NO:1 or at a position corresponding to this position in the sequence from which the HIV synthase variant is derived, is deleted or substituted with glycine; and/or
(7) the amino acid residue at position 41 in the amino acid sequence shown in SEQ ID NO:1 or at a position corresponding to this position in the sequence from which the HIV synthase variant is derived, is deleted or substituted with serine; and/or
(8) the amino acid residue at position 43 in the amino acid sequence shown in SEQ ID NO:1 or at a position corresponding to this position in the sequence from which the HIV synthase variant is derived, is deleted or substituted with valine; and/or
(9) the amino acid residue at position 54 in the amino acid sequence shown in SEQ ID NO:1 or at a position corresponding to this position in the sequence from which the HIV synthase variant is derived, is deleted or substituted with glycine; and/or
(10) the amino acid residue at position 74 in the amino acid sequence shown in SEQ ID NO:1 or at a position corresponding to this position in the sequence from which the HIV synthase variant is derived, is deleted or substituted with glutamic acid; and/or
(11) the amino acid residue at position 81 in the amino acid sequence shown in SEQ ID NO:1 or at a position corresponding to this position in the sequence from which the HIV synthase variant is derived, is deleted or substituted with arginine; and/or
(12) the amino acid residue at position 165 in the amino acid sequence shown in SEQ ID NO:1 or at a position corresponding to this position in the sequence from which the HIV synthase variant is derived, is deleted or substituted with proline or glutamine; and/or
(13) the amino acid residue at position 167 in the amino acid sequence shown in SEQ ID NO:1 or at a position corresponding to this position in the sequence from which the HIV synthase variant is derived, is deleted or substituted with alanine; and/or
(14) the amino acid residue at position 171 in the amino acid sequence shown in SEQ ID NO:1 or at a position corresponding to this position in the sequence from which the HIV synthase variant is derived, is substituted with alanine or glycine; and/or
(15) the amino acid residue at position 201 in the amino acid sequence shown in SEQ ID NO:1 or at a position corresponding to this position in the sequence from which the HIV synthase variant is derived, is deleted or substituted with threonine; and/or
(16) the amino acid residue at position 221 in the amino acid sequence shown in SEQ ID NO:1 or at a position corresponding to this position in the sequence from which the HIV synthase variant is derived, is deleted or substituted with leucine, valine, isoleucine or threonine; and/or
(17) the amino acid residue at position 222 in the amino acid sequence shown in SEQ ID NO:1 or at a position corresponding to this position in the sequence from which the HIV synthase variant is derived, is deleted or substituted with arginine, glutamine, lysine or histidine; and/or
(18) the amino acid residue at position 226 in the amino acid sequence shown in SEQ ID NO:1 or at a position corresponding to this position in the sequence from which the HIV synthase variant is derived, is deleted or substituted with methionine; and/or
(19) the amino acid residue at position 246 in the amino acid sequence shown in SEQ ID NO:1 or at a position corresponding to this position in the sequence from which the HIV synthase variant is derived, is deleted or substituted with arginine; and/or
(20) the amino acid residue at position 259 in the amino acid sequence shown in SEQ ID NO:1 or at a position corresponding to this position in the sequence from which the HIV synthase variant is derived, is deleted or substituted with aspartic acid; and/or
(21) the amino acid residue at position 296 in the amino acid sequence shown in SEQ ID NO:1 or at a position corresponding to this position in the sequence from which the HIV synthase variant is derived, is deleted or substituted with glutamine; and/or
(22) the amino acid residue at position 325 in the amino acid sequence shown in SEQ ID NO:1 or at a position corresponding to this position in the sequence from which the HIV synthase variant is derived, is deleted or substituted with alanine, leucine or valine; and/or

(23) the amino acid residue at position 338 in the amino acid sequence shown in SEQ ID NO:1 or at a position corresponding to this position in the sequence from which the HIV synthase variant is derived, is deleted or substituted with proline; and/or

(24) the amino acid residue at position 345 in the amino acid sequence shown in SEQ ID NO:1 or at a position corresponding to this position in the sequence from which the HIV synthase variant is derived, is deleted or substituted with phenylalanine; and/or

(25) the amino acid residue at position 363 in the amino acid sequence shown in SEQ ID NO:1 or at a position corresponding to this position in the sequence from which the HIV synthase variant is derived, is deleted or substituted with arginine; and/or

(26) the amino acid residue at position 394 in the amino acid sequence shown in SEQ ID NO:1 or at a position corresponding to this position in the sequence from which the HIV synthase variant is derived, is deleted or substituted with serine; and/or

(27) the amino acid residue at position 396 in the amino acid sequence shown in SEQ ID NO:1 or at a position corresponding to this position in the sequence from which the HIV synthase variant is derived, is deleted or substituted with asparagine; and/or

(28) the amino acid residue at position 457 in the amino acid sequence shown in SEQ ID NO:1 or at a position corresponding to this position in the sequence from which the HIV synthase variant is derived, is deleted or substituted with cysteine; and/or

(29) the amino acid residue at position 462 in the amino acid sequence shown in SEQ ID NO:1 or at a position corresponding to this position in the sequence from which the HIV synthase variant is derived, is deleted or substituted with tyrosine; and/or

(30) the amino acid residue at position 473 in the amino acid sequence shown in SEQ ID NO:1 or at a position corresponding to this position in the sequence from which the HIV synthase variant is derived, is deleted or substituted with aspartic acid or glycine; and/or

(31) the amino acid residue at position 475 in the amino acid sequence shown in SEQ ID NO:1 or at a position corresponding to this position in the sequence from which the HIV synthase variant is derived, is deleted or substituted with arginine; and/or

(32) the amino acid residue at position 480 in the amino acid sequence shown in SEQ ID NO:1 or at a position corresponding to this position in the sequence from which the HIV synthase variant is derived, is deleted or substituted with cysteine; and/or

(33) the amino acid residue at position 481 in the amino acid sequence shown in SEQ ID NO:1 or at a position corresponding to this position in the sequence from which the HIV synthase variant is derived, is deleted or substituted with serine; and/or

(34) the amino acid residue at position 486 in the amino acid sequence shown in SEQ ID NO:1 or at a position corresponding to this position in the sequence from which the HIV synthase variant is derived, is deleted or substituted with arginine; and/or

(35) the amino acid residue at position 490 in the amino acid sequence shown in SEQ ID NO:1 or at a position corresponding to this position in the sequence from which the HIV synthase variant is derived, is deleted or substituted with asparagine; and/or

(36) the amino acid residue at position 491 in the amino acid sequence shown in SEQ ID NO:1 or at a position corresponding to this position in the sequence from which the HIV synthase variant is derived, is deleted or substituted with alanine; and/or

(37) the amino acid residue at position 500 in the amino acid sequence shown in SEQ ID NO:1 or at a position corresponding to this position in the sequence from which the HIV synthase variant is derived, is deleted or substituted with serine; and/or

(38) the amino acid residue at position 514 in the amino acid sequence shown in SEQ ID NO:1 or at a position corresponding to this position in the sequence from which the HIV synthase variant is derived, is deleted or substituted with arginine, glycine or serine; and/or

(39) the amino acid residue at position 516 in the amino acid sequence shown in SEQ ID NO:1 or at a position corresponding to this position in the sequence from which the HIV synthase variant is derived, is deleted or substituted with asparagine; and/or

(40) the amino acid residue at position 519 in the amino acid sequence shown in SEQ ID NO:1 or at a position corresponding to this position in the sequence from which the HIV synthase variant is derived, is deleted or substituted with aspartic acid; and/or

(41) the amino acid residue at position 520 in the amino acid sequence shown in SEQ ID NO:1 or at a position corresponding to this position in the sequence from which the HIV synthase variant is derived, is deleted or substituted with serine.

19. The method of claim 13, wherein said HIV synthase variant further comprises an amino acid residue at position 75 in the amino acid sequence shown in SEQ ID NO:1 or at a position corresponding to this position in the sequence from which the HIV synthase variant is derived, is deleted or substituted with asparagine.

20. The method of claim 13, wherein X is S—CH2-CH2-NH—CO—CH2-CH2-NH—CO—CH(OH)—C(CH3)2-CH2-O—PO2H—O—PO2H—C10H13N5O7P (coenzyme A).

21. The method of claim 13, wherein the method is carried out by culturing a host cell to express the HIV synthase variant to produce HIV.

22. The method of claim 13 wherein the method further comprises the step of converting the produced HIV into isobutene.

* * * * *

UNITED STATES PATENT AND TRADEMARK OFFICE
CERTIFICATE OF CORRECTION

| | | |
|---|---|---|
| PATENT NO. | : 10,364,418 B2 | Page 1 of 1 |
| APPLICATION NO. | : 15/108917 | |
| DATED | : July 30, 2019 | |
| INVENTOR(S) | : Philippe Marlière et al. | |

It is certified that error appears in the above-identified patent and that said Letters Patent is hereby corrected as shown below:

Column 109, Line 48 Claim 6(12), should read:
--the amino acid residue at position 165 in the amino acid sequence shown in SEQ ID NO: 1 or at a position corresponding to this position in the sequence from which the HIV synthase variant is derived, is deleted or substituted with proline or glutamine; and/or--

Column 109, Line 58 Claim 6(14), should read:
--the amino acid residue at position 171 in the amino acid sequence shown in SEQ ID NO: 1 or at a position corresponding to this position in the sequence from which the HIV synthase variant is derived, is substituted with alanine or glycine; and/or--

Column 110, Line 58 Claim 6(27), should read:
--the amino acid residue at position 396 in the amino acid sequence shown in SEQ ID NO: 1 or at a position corresponding to this position in the sequence from which the HIV synthase variant is derived, is substituted with asparagine; and/or--

Column 117, Line 23 Claim 18(27), should read:
--the amino acid residue at position 396 in the amino acid sequence shown in SEQ ID NO: 1 or at a position corresponding to this position in the sequence from which the HIV synthase variant is derived, is substituted with asparagine; and/or--

Signed and Sealed this
Fourteenth Day of April, 2020

Andrei Iancu
*Director of the United States Patent and Trademark Office*